US008940891B2

United States Patent
Tran et al.

(10) Patent No.: US 8,940,891 B2
(45) Date of Patent: Jan. 27, 2015

(54) MODULATORS OF THE PROSTACYCLIN (PGI2) RECEPTOR USEFUL FOR THE TREATMENT OF DISORDERS RELATED THERETO

(75) Inventors: Thuy-Anh Tran, San Diego, CA (US); Rena Hayashi, Hacienda Heights, CA (US); Jason B. Ibarra, Las Vegas, NV (US); Brett Ullman, San Diego, CA (US); Ning Zou, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 387 days.

(21) Appl. No.: 13/133,036

(22) PCT Filed: Dec. 7, 2009

(86) PCT No.: PCT/US2009/006408
§ 371 (c)(1),
(2), (4) Date: Jun. 6, 2011

(87) PCT Pub. No.: WO2010/077275
PCT Pub. Date: Jul. 8, 2010

(65) Prior Publication Data
US 2011/0245251 A1    Oct. 6, 2011

Related U.S. Application Data

(60) Provisional application No. 61/201,150, filed on Dec. 8, 2008, provisional application No. 61/205,726, filed on Jan. 22, 2009.

(51) Int. Cl.
| | |
|---|---|
| *C07D 253/07* | (2006.01) |
| *C07D 401/04* | (2006.01) |
| *C07D 403/04* | (2006.01) |
| *A61K 31/53* | (2006.01) |
| *A61K 31/4427* | (2006.01) |
| *A61P 9/12* | (2006.01) |
| *A61P 11/08* | (2006.01) |
| *C07D 409/04* | (2006.01) |
| *C07D 237/14* | (2006.01) |
| *A61K 31/50* | (2006.01) |
| *A61K 31/501* | (2006.01) |

(52) U.S. Cl.
CPC ............ *C07D 237/14* (2013.01); *C07D 253/07* (2013.01); *C07D 401/04* (2013.01); *C07D 403/04* (2013.01); *C07D 409/04* (2013.01)
USPC ......................................... 544/182; 514/242

(58) Field of Classification Search
USPC .......................................... 544/182; 514/242
See application file for complete search history.

(56) References Cited

U.S. PATENT DOCUMENTS

| | | |
|---|---|---|
| 5,849,919 A | 12/1998 | Hamanaka et al. |
| 6,746,729 B1 | 6/2004 | Cherkaoui et al. |
| 7,115,746 B2 | 10/2006 | Snoonian et al. |
| 7,202,253 B2 | 4/2007 | Lloyd et al. |
| 7,226,550 B2 | 6/2007 | Hou et al. |
| 2003/0144350 A1 | 7/2003 | Stevenson et al. |
| 2004/0048844 A1 | 3/2004 | Nugiel et al. |
| 2006/0063930 A1 | 3/2006 | Agoston et al. |
| 2006/0258728 A1 | 11/2006 | Tani et al. |
| 2011/0053958 A1 | 3/2011 | Tran et al. |
| 2011/0224262 A1* | 9/2011 | Tran et al. ............... 514/341 |

FOREIGN PATENT DOCUMENTS

| | | |
|---|---|---|
| CA | 2125074 | 12/1994 |
| EP | 0028829 | 5/1981 |

(Continued)

OTHER PUBLICATIONS

Mubarak KK. Respir Med. 2010, 104(1):9-21.*
Freshney et al.,Culture of Animal Cells, A Manual of Basic Technique, Alan R. Liss, Inc., 1983, New York, p. 4.*
Dermer et al., Bio/Technology, 1994, 12:320.*
Aguilar et al. Am. J. Respir. Crit. Care Med, 2000, 162:1846-1850.
Archer et al, Am. J. Respir. Crit. Care Med., 1998, 158:1061-1067.
Arehart et al., Curr. Med. Chem.2007, 14:2161-2169.

(Continued)

*Primary Examiner* — Venkataraman Balasubramanian

(57) ABSTRACT

Cyclohexane derivatives of Formula Ia and pharmaceutical compositions thereof that modulate the activity of the PGI2 receptor. Compounds of the present invention and pharmaceutical compositions thereof are directed to methods useful in the treatment of: pulmonary arterial hypertension (PAH) and related disorders; platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherosclerosis; atherothrombosis; asthma or a symptom thereof; a diabetic-related disorder such as diabetic peripheral neuropathy, diabetic nephropathy or diabetic retinopathy; glaucoma or other disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; ischemia-reperfusion injury; restenosis; atherosclerosis; acne; type 1 diabetes; type 2 diabetes; sepsis; and chronic obstructive pulmonary disorder (COPD).

(1A)

44 Claims, 6 Drawing Sheets

(56) References Cited

FOREIGN PATENT DOCUMENTS

| | | |
|---|---|---|
| EP | 0442448 | 8/1991 |
| EP | 1046631 | 10/2000 |
| IN | 1995DEL00358 | 3/1995 |
| IN | 2006DELNP04486 | 8/2006 |
| JP | 3160438 | 7/1991 |
| JP | 06329598 | 11/1994 |
| JP | 11269138 | 10/1999 |
| JP | 2005104853 | 4/2005 |
| JP | 2006083085 | 3/2006 |
| JP | 2006137856 | 6/2006 |
| JP | 2007161867 | 6/2007 |
| WO | WO 02/055484 | 7/2002 |
| WO | WO 07/051255 | 5/2007 |
| WO | WO 07/133653 | 11/2007 |
| WO | WO 2009/117095 | 9/2009 |
| WO | WO 2010/077275 | 7/2010 |
| WO | WO 2011/037613 | 3/2011 |

OTHER PUBLICATIONS

Arehart et al., Circ. Res. 2008, 102(8), 986-93 (Epub Mar. 6, 2008).
Asada et al., "Discovery of a series of acrylic acids and their derivatives as chemical leads for selective EP3 receptor antagonists", Bioorganic & Medicinal Chemistry, Pergamon, GB, vol. 17, No. 18, Sep. 15, 2009, pp. 6567-6582.
Badesch et al., Ann. Intern. Med., 2000, 132:425-434.
Badesch et al., Journal of the American College of Cardiology, vol. 43, No. 12 Suppl. S, 56S-61S, Jun. 2004.
Berge et al., Journal of Pharmaceutical Sciences, 66:1-19(1977).
Bernabei et al., Ann. Thorac. Surg., 1995, 59:149-153.
Boehme et al., Rheumatol. Int. 2006, 340-347.
Burnette et al, Exp. Eye Res., 2006, 83:1359-1365.
Cameron et al., Naunyn Schmiedebergs Arch. Pharmacol., 2003, 367:607-614.
Cameron, Diabetologia, 2001, 44:1973-1988.
Chan, J. Nutr., 1998, 128:1593-1596.
Cheng et al., Science, 2002, 296:539-541.
Collier, T.L. et al, *J. Labelled Compd. Radiopharm*, 1999, 42, S264-S266.
Cote, F., et al., PNAS 100(23): 13525-13530 (2003).
Cotter et al., Naunyn Schmiedebergs Arch. Pharmacol., 1993, 347:534-540.
Czeslick et al., Eur. J. Clin, Invest., 2003, 33:1013-1017.
Davi et al, N. Eng. J. Med., 2007, 357:2482-2494.
Di Renzo et al., Prostaglandin Leukot. Essent. Fatty Acids, 2005, 73:405-410.
Dogan et al., Gen. Pharmacol., 1996, 27:1163-1166.
Driscoll et al., "Medical therapy for pulmonary arterial hypertension", Expert Opin. Pharmacother., 2008, vol. 9, pp. 65-81.
Egan et al., Science, 2004, 306:1954-1957.
Fang et al, J. Cereb. Blood Flow Metab., 2006, 26:491-501.
Fetalvero et al., Prostaglandins Other Lipid Mediat. 2007, 82:109-118.
Fetalvero et al., Am. J. Physiol. Heart. Circ. Physiol., 2006, 290:H1337-H1346.
Fries et al., Hematology Am. Soc. Hematol. Educ.Program, 2005:445-451.
Fujiwara et al., Exp. Clin. Endocrinol. Diabetes, 2004, 112:390-394.
Gabriel et al, ASSAY and Drug Development Technologies, 1:291-303, 2003.
Gainza et al, J. Nephrol., 2006, 19:648-655.
Gao et al., Rheumatol. Int., 2002, 22:45-51.
Goya et al., Metabolism Clinical and Experimental, 2003, 52:192-198.
Guillory, "Generation of Polymorphs, Hydrates, Solvates, and Amorphous Solids," *Polymorphism in Pharmaceutical Solids*, ed. Harry G. Brittan, vol. 95, Marcel Dekker, Inc., New York 1999, pp. 183-226.
Harada et al., Shock, 2008, 30(4): 379-87 (Epub Feb. 21, 2008).

Higuchi and Stella, Pro-drugs as Novel Delivery Systems, vol. 14 of the A.C.S. Symposium Series; and in *Bioreversible Carriers in Drug Design*, ed. Edward B. Roche, American Pharmaceutical Association and Pergamon Press 1987.
Hoeper et al., Ann. Intern. Med., 1999, 130:506-509.
Hoeper et al., Eur. Respor. J., 2005, 25:502-508.
Hotta et al, Diabetes, 1996, 45:361-366.
Hotta et al, Prostaglandins 1995, 49:339-349.
Hoyng et al., Invest. Ophthalmol. Vis. Sci., 1987, 28:470-476.
Humbert et al., J. Am. Coll. Cardiol., 2004, 43:13S-24S.
Humbert et al, Eur. Respir. J., 1999, 13:1351-1356.
Idzko et al, J. Clin. Invest., 2007, 117:464-472.
Jaffar et al., J. Immunol, 2007, 179:6193-6203.
Jozefowski et al., Int. Immunopharmcol., 2003, 3:865-878.
Klapars et al., J. Am. Chem. Soc., 2002, 124, 7421-7428.
Kobayashi et al., J. Clin. Invest., 2004, 114:784-794.
Koike et al., FASEB J. 2003, 17:779-781.
Le Bas, M.D. et al. in *J. Labelled Compd. Radiopharm*, 2001, 44, S280-S282.
Liu et al., Respiratory Medicine, Baillier Tindall, London, GB vol. 100, No. 5, May 1, 2006, pp. 765-774.
Lundblad et al., Journal of Cerebral Blood Flow & Metabolism (2008), 367-376.
Mardla et al., Platelets, 2004, 15:319-324.
McCormick et al., Biochem. Soc. Trans., 2007, 35:910-911.
McGoon et al., Chest 2004, 126:14S-34S.
McLaughlin et al, Pulmonary arterial hypertension:, Circulation, 2006, vol. 114, No. 13, pp. 1417-1431.
Miwa et al., Int. Heart J., 2007, 48:417-422.
Moncada et al., Lancet, 1977, 1:18-20.
Morecroft, I., et al, Hypertension 49: 232-236 (2007).
Moss, Pure & Appl. Chem., vol. 68, No. 12, 2193-2222 (1996).
Murata et al., Nature, 1997, 388:678-682.
Naeije et al., Expert Opin.Pharmacother., 2007,8:2247-2265.
Nagao et al., Am. J. Respir. Cell Mol. Biol. 2003; 29:314-320.
Okuda et al., Prostaglandins 1996, 52:375-384.
Owada et al., Nephron, 2002, 92:788-796.
Potapov, V. M., Stereochemistry. 2nd Ed [Textbook for Chemistry Majors]. USSR. (1988), p. 202, Publisher: (Khimiya, Moscow, USSR) (English translation).
Rabinovitch, Annu. Rev. Pathol. Mech. Dis., 2007, 2:369-399.
Raychaudhuri et al., J. Biol. Chem. 2002, 277:33344-33348.
Robbins et al, Chest 2000, 117:14-18.
Rosenkranz, Pulmonary hypertension: Current diagnosis and treatment:, Clin. Res. Cardiol., 2007, vol. 96, No. 8, pp. 527-541.
Rosenzweig, "Emerging treatments for pulmonary arterial hypertension", Expert Opin. Emerging Drugs, 2006, vol. 11, No. 4, pp. 609-619.
Rosenzweig et al, Circulation, 1999, 99:1858-1865.
Sato, T., et al., Journal of Molecular and Cellular Cardiology, Academic Press, GB, vol. 22, May 1, 1990, p. S74.
Schermuly et al., Circ. Res., 2004, 94:1101-1108.
Seiler, S.M. et al., Thrombosis Research, Tarrytown, NY, US, vol. 74, No. 2, Apr. 15, 1994, pp. 115-123.
Shindo et al., Prostaglandins, 1991, 41:85-96.
Shinomiya et al., Biochem. Pharmacol., 2001, 61:1153-1160.
Simonneau et al., J. Am. Coll. Cardiol., 2004, 43:5S-12S.
Stitham et al., Prostaglandins Other Lipid Mediat., 2007, 82:95-108.
Strauss et al., Clin. Chest. Med. 2007, 28:127-142.
Strieter, Eric R., et al., JACS Communications, J. Am. Chem. Soc., 2005, 127, 4120-4121.
Szekeres, I., et al. Journal of Molecular and Cellular Cardiology, Academic Press, GB, vol. 15, Jul. 1, 1983, p. 132.
Taichman et al., Clin. Chest. Med., 2007; 28:1-22.
Takahashi et al., Br. J. Pharmacol, 2002, 137:315-322.
Tawara et al., Journal of Cardiovascular Pharmacology (2007), 50(2), 195-200.
Tuder et al, Am. J. Respir. Crit. Care Med., 1999, 159:1925-1932.
Xiao et al., Circulation 2001, 104:2210-2215.
Ueno et al., Jpn. J. Pharmacol, 1996, 70:177-182.
Ueno et al, Life Sci., 1996, 59:PL105-PL110.
Van Rijt et al., J. Exp. Med., 2005, 201:981-991.
Walther, D.J., et al, Science 299:76 (2003).

(56) References Cited

OTHER PUBLICATIONS

Wang et al., Proc. Natl. Acad. Sci. USA 2006, 103:14507-14512.
Yamada et al, Peptides, 2008, 29:412-418.
Yamagishi et al, Mol. Med. 2002, 8:546-550.
Yamashita et al., Diabetes Res. Clin. Pract., 2002, 57:149-161.
Zhang et al, Arch. Biochem. Biophys., 2006, 454:80-88.
Zhou et al., J. Immunol., 2007, 178:702-710.
Zhu, G-D. et al, J. Org. Chem., 2002, 67, 943-948.
Caojin, et al, "Comparison of Acute Hemodynamic Effects of Aerosolized Iloprost and Inhaled Nitric Oxide in Adult Congenital Heart Disease with Severe Pulmonary Arterial Hypertension," Department of Cardiology, Guangdong General Hospital & Guangdong Cardiovascular Institute, China, Intern Med, vol. 51, Jul. 12, 2012, pp. 2857-2862.
Muller, et al, "Iloprost has potent anti-inflammatory properties on human monocyte-derived dendritic cells," Clinical & Experimental Allergy, Department of Pneumology, University of Freiburg, Germany, 2010, (40), pp. 1214-1221.
Tennis, et al, "The Role of Prostacyclin in Lung Cancer," Translation Research, Division of Pulmonary Sciences and Critical Care Medicine, Department of Medicine, University of Colorado Denver Health Sciences, Denver, Colorado, vol. 155, No. 2, Feb. 2010, pp. 57-61.
Baradia, et al, "Inhalation Therapy to Treat Pulmonary Arterial Hypertension," Pharm. Pat. Analyst, 2012, 1(5), pp. 577-588.
Gryglewski, Pharmacol Rep. Jan.-Feb. 2008;60(1):3-11. "Prostacyclin among prostanoids."
Kurihara et al., Br J Pharmacol. Jan. 1990;99(1):91-6. "Protective effect of beraprost sodium . . . ."
Chen, et al., Am J Physiol Lung Cell Mol Physiol. Apr. 2009;296(4): L648-56. "Protective effect of beraprost sodium . . . ."
Wang et al., Am J Physiol Renal Physiol. Oct. 2007;293(4):F1131-6. "Prostacyclin in endotoxemia-induced acute kidney injury . . . ."

* cited by examiner

MODULATORS OF THE PROSTACYCLIN (PGI2) RECEPTOR USEFUL FOR THE TREATMENT OF DISORDERS RELATED THERETO

CROSS-REFERENCE TO RELATED APPLICATIONS

This application is a National Stage of International Application No. PCT/US2009/006408, filed Dec. 7, 2009, which claims the benefit of U.S. Provisional Application Nos. 61/201,150, filed Dec. 8, 2008 and 61/205,726, filed Jan. 22, 2009, each of which is incorporated herein by reference in its entirety.

FIELD OF THE INVENTION

The present invention relates to certain compounds of Formula Ia and pharmaceutical compositions thereof that modulate the activity of the PGI2 receptor. Compounds of the present invention and pharmaceutical compositions thereof are directed to methods useful in the treatment of: pulmonary arterial hypertension (PAH); idiopathic PAH; familial PAH; PAH associated with: a collagen vascular disease, a congenital heart disease, portal hypertension, HIV infection, ingestion of a drug or toxin, hereditary hemorrhagic telangiectasia, splenectomy, pulmonary veno-occlusive disease (PVOD) or pulmonary capillary hemangiomatosis (PCH); PAH with significant venous or capillary involvement; platelet aggregation; coronary artery disease; myocardial infarction; transient ischemic attack; angina; stroke; ischemia-reperfusion injury; restenosis; atrial fibrillation; blood clot formation in an angioplasty or coronary bypass surgery individual or in an individual suffering from atrial fibrillation; atherothrombosis; asthma or a symptom thereof; a diabetic-related disorder such as diabetic peripheral neuropathy, diabetic nephropathy or diabetic retinopathy; glaucoma or other disease of the eye with abnormal intraocular pressure; hypertension; inflammation; psoriasis; psoriatic arthritis; rheumatoid arthritis; Crohn's disease; transplant rejection; multiple sclerosis; systemic lupus erythematosus (SLE); ulcerative colitis; atherosclerosis; acne; type 1 diabetes; type 2 diabetes; sepsis; and chronic obstructive pulmonary disorder (COPD).

BACKGROUND OF THE INVENTION

Prostacyclin (PGI2) is a lipid molecule derived from arachidonic acid through the cyclooxygenase pathway. It is a potent vasodilator, antiproliferative, anti-thrombotic and antiplatelet agent that mediates its effects as an agonist of a G protein-coupled receptor (PGI2 receptor; e.g., human PGI2 receptor, GenBank® Accession No. NP_000951 and alleles thereof). It is known that the binding of PGI2 (or other such agonist) to the PGI2 receptor leads to coupling with the Gs protein and increases intracellular cAMP levels. (See, e.g., Zhang et al., Arch. Biochem. Biophys., 2006, 454:80-88.)

Pulmonary arterial hypertension (PAH) is a life-threatening disease characterized by a progressive pulmonary vasculopathy leading to right ventricular hypertrophy. Right heart failure occurs if left untreated. Prostacyclin, which has vasodilatory and antiproliferative effects on the pulmonary vasculature has been found to be low in patients with PAH compared with normal controls. Exogenous administration of prostacyclin or an analog of prostacyclin (i.e., an agonist of the PGI2 receptor) has become an important strategy in the treatment of PAH. (See, e.g., Tuder et al., Am. J. Respir. Crit. Care. Med., 1999, 159:1925-1932; Humbert et al., J. Am. Coll. Cardiol., 2004, 43:13S-24S; Rosenzweig, Expert Opin. Emerging Drugs, 2006, 11:609-619; McLaughlin et al., Circulation, 2006, 114:1417-1431; Rosenkranz, Clin. Res. Cardiol., 2007, 96:527-541; Driscoll et al., Expert Opin. Pharmacother., 2008, 9:65-81.)

Trepostinil and iloprost are FDA-approved analogs of prostacyclin which, like prostacyclin, are not orally-active. Beraprost is an orally-active analog of prostacyclin approved for the treatment of PAH in Japan, but it has failed registration for the treatment of PAH in Europe and in the US. Of the three FDA-approved drugs, prostacyclin is the best studied in PAH patients. The approximate annual cost of treating PAH with these drugs is $25,000 to $200,000 depending on the dose. At present, many experts consider intravenous prostacyclin to be the most reliable agent for managing the sickest PAH patients. Due to the short half-life of prostacyclin, intravenous treatment is complicated by the need for a continuous infusion. Patients are at risk for potentially fatal rebound pulmonary hypertension if the infusion is abruptly disrupted, as well as significant risk of catheter-related complications including sepsis. (See, e.g., Rosenzweig, Expert Opin. Emerging Drugs, 2006, 11:609-619; Naeije et al., Expert Opin. Pharmacother., 2007, 8:2247-2265; Strauss et al., Clin. Chest. Med., 2007, 28:127-142; Driscoll et al., Expert Opin. Pharmacother., 2008, 9:65-81.)

There is considerable interest in developing prostacyclin analogs (i.e., agonists of the PGI2 receptor) for use in the treatment of other diseases, such as atherothrombosis. Developing stable, orally-active analogs of prostacyclin (i.e., stable, orally-active agonists of the PGI2 receptor) is a rate-limiting step in achieving this goal (see, e.g., Arehart et al., Curr. Med. Chem., 2007, 14:2161-2169; Arehart et al., Circ. Res., 2008, 102(8), 986-93), as well as in the improved management of PAH.

SUMMARY OF THE INVENTION

One aspect of the present invention encompasses certain cyclohexane derivatives selected from compounds of Formula Ia and pharmaceutically acceptable salts, solvates and hydrates thereof:

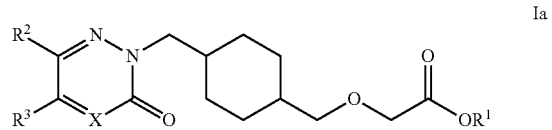

Ia wherein:

$R^1$ is selected from: H and $C_1$-$C_8$ alkyl;

$R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen; and X is selected from: N and CH.

One aspect of the present invention pertains to pharmaceutical compositions comprising a compound of the present invention and a pharmaceutically acceptable carrier.

One aspect of the present invention pertains to methods for the treatment of a PGI2 receptor mediated disorder in an individual, comprising administering to the individual in need thereof, a therapeutically effective amount of a compound of the present invention or a pharmaceutical composition thereof.

One aspect of the present invention pertains to methods for the treatment of PAH in an individual, comprising administering to the individual in need thereof, a therapeutically effective amount of a compound of the present invention or a pharmaceutical composition thereof.

One aspect of the present invention pertains to methods for the treatment of idiopathic PAH in an individual, comprising administering to the individual in need thereof, a therapeutically effective amount of a compound of the present invention or a pharmaceutical composition thereof.

One aspect of the present invention pertains to methods for the treatment of familial PAH in an individual, comprising administering to the individual in need thereof, a therapeutically effective amount of a compound of the present invention or a pharmaceutical composition thereof.

One aspect of the present invention pertains to methods for the treatment of PAH associated with a collagen vascular disease in an individual, comprising administering to the individual in need thereof, a therapeutically effective amount of a compound of the present invention or a pharmaceutical composition thereof.

One aspect of the present invention pertains to methods for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis in an individual, comprising administering to the individual in need thereof, a therapeutically effective amount of a compound of the present invention or a pharmaceutical composition thereof.

One aspect of the present invention pertains to methods for the treatment of PAH associated with a congenital heart disease in an individual, comprising administering to the individual in need thereof, a therapeutically effective amount of a compound of the present invention or a pharmaceutical composition thereof.

One aspect of the present invention pertains to methods for the treatment of PAH associated with a congenital heart disease selected from: atrial septal defect (ASD), ventricular septal defect (VSD) and patent ductus arteriosus in an individual, comprising administering to the individual in need thereof, a therapeutically effective amount of a compound of the present invention or a pharmaceutical composition thereof.

One aspect of the present invention pertains to methods for the treatment of PAH associated with portal hypertension in an individual, comprising administering to the individual in need thereof, a therapeutically effective amount of a compound of the present invention or a pharmaceutical composition thereof.

One aspect of the present invention pertains to methods for the treatment of PAH associated with HIV infection in an individual, comprising administering to the individual in need thereof; a therapeutically effective amount of a compound of the present invention or a pharmaceutical composition thereof.

One aspect of the present invention pertains to methods for the treatment of PAH associated with ingestion of a drug or toxin in an individual, comprising administering to the individual in need thereof, a therapeutically effective amount of a compound of the present invention or a pharmaceutical composition thereof.

One aspect of the present invention pertains to methods for the treatment of PAH associated with hereditary hemorrhagic telangiectasia in an individual, comprising administering to the individual in need thereof, a therapeutically effective amount of a compound of the present invention or a pharmaceutical composition thereof.

One aspect of the present invention pertains to methods for the treatment of PAH associated with splenectomy in an individual, comprising administering to the individual in need thereof, a therapeutically effective amount of a compound of the present invention or a pharmaceutical composition thereof.

One aspect of the present invention pertains to methods for the treatment of PAH associated with significant venous or capillary involvement in an individual, comprising administering to the individual in need thereof, a therapeutically effective amount of a compound of the present invention or a pharmaceutical composition thereof.

One aspect of the present invention pertains to methods for the treatment of PAH associated with pulmonary veno-occlusive disease (PVOD) in an individual, comprising administering to the individual in need thereof, a therapeutically effective amount of a compound of the present invention or a pharmaceutical composition thereof.

One aspect of the present invention pertains to methods for the treatment of PAH associated with pulmonary capillary hemangiomatosis (PCH) in an individual, comprising administering to the individual in need thereof; a therapeutically effective amount of a compound of the present invention or a pharmaceutical composition thereof.

One aspect of the present invention pertains to methods for the treatment of platelet aggregation in an individual, comprising administering to the individual in need thereof, a therapeutically effective amount of a compound of the present invention or a pharmaceutical composition thereof.

One aspect of the present invention pertains to methods for the treatment of: coronary artery disease, myocardial infarction, transient ischemic attack, angina, stroke, ischemia-reperfusion injury, restenosis or atrial fibrillation in an individual, comprising administering to the individual in need thereof, a therapeutically effective amount of a compound of the present invention or a pharmaceutical composition thereof.

One aspect of the present invention pertains to methods for the treatment of blood clot formation in an angioplasty or coronary bypass surgery individual comprising administering to the individual in need thereof, a therapeutically effective amount of a compound of the present invention or a pharmaceutical composition thereof.

One aspect of the present invention pertains to methods for the treatment of blood clot formation in an individual suffering from atrial fibrillation comprising administering to the individual in need thereof, a therapeutically effective amount of a compound of the present invention or a pharmaceutical composition thereof.

One aspect of the present invention pertains to methods for the treatment of atherosclerosis in an individual, comprising administering to the individual in need thereof, a therapeutically effective amount of a compound of the present invention or a pharmaceutical composition thereof.

One aspect of the present invention pertains to methods for the treatment of atherothrombosis in an individual, comprising administering to the individual in need thereof, a therapeutically effective amount of a compound of the present invention or a pharmaceutical composition thereof.

One aspect of the present invention pertains to methods for the treatment of asthma in an individual, comprising administering to the individual in need thereof, a therapeutically effective amount of a compound of the present invention or a pharmaceutical composition thereof.

One aspect of the present invention pertains to methods for the treatment of a symptom of asthma in an individual, comprising administering to the individual in need thereof, a therapeutically effective amount of a compound of the present invention or a pharmaceutical composition thereof.

One aspect of the present invention pertains to methods for the treatment of a diabetic-related disorder in an individual, comprising administering to the individual in need thereof, a therapeutically effective amount of a compound of the present invention or a pharmaceutical composition thereof.

One aspect of the present invention pertains to methods for the treatment of diabetic peripheral neuropathy in an individual, comprising administering to the individual in need thereof, a therapeutically effective amount of a compound of the present invention or a pharmaceutical composition thereof.

One aspect of the present invention pertains to methods for the treatment of diabetic nephropathy in an individual, comprising administering to the individual in need thereof, a therapeutically effective amount of a compound of the present invention or a pharmaceutical composition thereof.

One aspect of the present invention pertains to methods for the treatment of diabetic retinopathy in an individual, comprising administering to the individual in need thereof, a therapeutically effective amount of a compound of the present invention or a pharmaceutical composition thereof.

One aspect of the present invention pertains to methods for the treatment of glaucoma or other disease of the eye with abnormal intraocular pressure in an individual, comprising administering to the individual in need thereof, a therapeutically effective amount of a compound of the present invention or a pharmaceutical composition thereof. In some embodiments the abnormal intraocular pressure is increased intraocular pressure.

One aspect of the present invention pertains to methods for the treatment of hypertension in an individual, comprising administering to the individual in need thereof, a therapeutically effective amount of a compound of the present invention or a pharmaceutical composition thereof.

One aspect of the present invention pertains to methods for the treatment of hypertension intended to confer protection against cerebral ischemia in an individual, comprising administering to the individual in need thereof, a therapeutically effective amount of a compound of the present invention or a pharmaceutical composition thereof.

One aspect of the present invention pertains to methods for the treatment of inflammation in an individual, comprising administering to the individual in need thereof, a therapeutically effective amount of a compound of the present invention or a pharmaceutical composition thereof.

One aspect of the present invention pertains to methods for the treatment of an inflammatory disease in an individual, comprising administering to the individual in need thereof, a therapeutically effective amount of a compound of the present invention or a pharmaceutical composition thereof.

One aspect of the present invention pertains to methods for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma in an individual, comprising administering to the individual in need thereof, a therapeutically effective amount of a compound of the present invention or a pharmaceutical composition thereof.

One aspect of the present invention pertains to methods of modulating the activity of a PGI2 receptor by contacting the receptor with a compound of the present invention.

One aspect of the present invention pertains to methods of agonizing a PGI2 receptor by contacting the receptor with a compound of the present invention.

One aspect of the present invention pertains to methods for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH) in an individual comprising administering to said individual in need thereof, a therapeutically effective amount of a compound of the present invention or a pharmaceutical composition thereof.

One aspect of the present invention pertains to methods for the treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD) in an individual comprising administering to said individual in need thereof, a therapeutically effective amount of a compound of the present invention or a pharmaceutical composition thereof.

One aspect of the present invention pertains to the use of a compound of the present invention in the manufacture of a medicament for the treatment of a PGI2 receptor mediated disorder.

One aspect of the present invention pertains to the use of a compound of the present invention in the manufacture of a medicament for the treatment of PAH.

One aspect of the present invention pertains to the use of a compound of the present invention in the manufacture of a medicament for the treatment of idiopathic PAH.

One aspect of the present invention pertains to the use of a compound of the present invention in the manufacture of a medicament for the treatment of familial PAH.

One aspect of the present invention pertains to the use of a compound of the present invention in the manufacture of a medicament for the treatment of PAH associated with collagen vascular disease.

One aspect of the present invention pertains to the use of a compound of the present invention in the manufacture of a medicament for the treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

One aspect of the present invention pertains to the use of a compound of the present invention in the manufacture of a medicament for the treatment of PAH associated with a congenital heart disease.

One aspect of the present invention pertains to the use of a compound of the present invention in the manufacture of a medicament for the treatment of PAH associated with a congenital heart disease selected from: atrial septic defect (ASD), ventricular septic defect (VSD) and patent ductus arteriosus.

One aspect of the present invention pertains to the use of a compound of the present invention in the manufacture of a medicament for the treatment of PAH associated with portal hypertension.

One aspect of the present invention pertains to the use of a compound of the present invention in the manufacture of a medicament for the treatment of PAH associated with HIV infection.

One aspect of the present invention pertains to the use of a compound of the present invention in the manufacture of a medicament for the treatment of PAH associated with ingestion of a drug or toxin.

One aspect of the present invention pertains to the use of a compound of the present invention in the manufacture of a medicament for the treatment of PAH associated with hereditary hemorrhagic telangiectasia.

One aspect of the present invention pertains to the use of a compound of the present invention in the manufacture of a medicament for the treatment of PAH associated with splenectomy.

One aspect of the present invention pertains to the use of a compound of the present invention in the manufacture of a medicament for the treatment of PAH associated with significant venous or capillary involvement.

One aspect of the present invention pertains to the use of a compound of the present invention in the manufacture of a medicament for the treatment of PAH associated with pulmonary veno-occlusive disease (PVOD).

One aspect of the present invention pertains to the use of a compound of the present invention in the manufacture of a medicament for the treatment of PAH associated with pulmonary capillary hemangiomatosis (PCH).

One aspect of the present invention pertains to the use of a compound of the present invention in the manufacture of a medicament for the treatment of platelet aggregation.

One aspect of the present invention pertains to the use of a compound of the present invention in the manufacture of a medicament for the treatment of a PGI2 receptor mediated disorder selected from: coronary artery disease, myocardial infarction, transient ischemic attack, angina, stroke, ischemia-reperfusion injury, restenosis and atrial fibrillation.

One aspect of the present invention pertains to the use of a compound of the present invention in the manufacture of a medicament for the treatment of blood clot formation in an angioplasty or coronary bypass surgery individual.

One aspect of the present invention pertains to the use of a compound of the present invention in the manufacture of a medicament for the treatment of blood clot formation in an individual suffering from atrial fibrillation.

One aspect of the present invention pertains to the use of a compound of the present invention in the manufacture of a medicament for the treatment of atherosclerosis.

One aspect of the present invention pertains to the use of a compound of the present invention in the manufacture of a medicament for the treatment of atherothrombosis.

One aspect of the present invention pertains to the use of a compound of the present invention in the manufacture of a medicament for the treatment of asthma.

One aspect of the present invention pertains to the use of a compound of the present invention in the manufacture of a medicament for the treatment of a symptom of asthma.

One aspect of the present invention pertains to the use of a compound of the present invention in the manufacture of a medicament for the treatment of a diabetic-related disorder.

One aspect of the present invention pertains to the use of a compound of the present invention in the manufacture of a medicament for the treatment of diabetic peripheral neuropathy.

One aspect of the present invention pertains to the use of a compound of the present invention in the manufacture of a medicament for the treatment of diabetic nephropathy.

One aspect of the present invention pertains to the use of a compound of the present invention in the manufacture of a medicament for the treatment of diabetic retinopathy.

One aspect of the present invention pertains to the use of a compound of the present invention in the manufacture of a medicament for the treatment of glaucoma or other disease of the eye with abnormal intraocular pressure. In some embodiments the abnormal intraocular pressure is increased intraocular pressure.

One aspect of the present invention pertains to the use of a compound of the present invention in the manufacture of a medicament for the treatment of hypertension.

One aspect of the present invention pertains to the use of a compound of the present invention in the manufacture of a medicament for the treatment of hypertension intended to confer protection against cerebral ischemia.

One aspect of the present invention pertains to the use of a compound of the present invention in the manufacture of a medicament for the treatment of inflammation.

One aspect of the present invention pertains to the use of a compound of the present invention in the manufacture of a medicament for the treatment of an inflammatory disease.

One aspect of the present invention pertains to the use of a compound of the present invention in the manufacture of a medicament for the treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to the use of a compound of the present invention in the manufacture of a medicament for modulating the activity of a PGI2 receptor.

One aspect of the present invention pertains to the use of a compound of the present invention in the manufacture of a medicament for agonizing a PGI2 receptor.

One aspect of the present invention pertains to the use of a compound of the present invention in the manufacture of a medicament for the treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

One aspect of the present invention pertains to the use of a compound of the present invention in the manufacture of a medicament for the treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

One aspect of the present invention pertains to compounds of the present invention for use in a method of treatment of the human or animal body by therapy.

One aspect of the present invention pertains to compounds of the present invention for use in a method of treatment of a PGI2 receptor mediated disorder.

One aspect of the present invention pertains to compounds of the present invention for use in a method of treatment of PAH.

One aspect of the present invention pertains to compounds of the present invention for use in a method of treatment of idiopathic PAH.

One aspect of the present invention pertains to compounds of the present invention for use in a method of treatment of familial PAH One aspect of the present invention pertains to compounds of the present invention for use in a method of treatment of PAH associated with a collagen vascular, disease.

One aspect of the present invention pertains to compounds of the present invention for use in a method of treatment of PAH associated with a collagen vascular disease selected from: scleroderma, CREST syndrome, systemic lupus erythematosus (SLE), rheumatoid arthritis, Takayasu's arteritis, polymyositis, and dermatomyositis.

One aspect of the present invention pertains to compounds of the present invention for use in a method of treatment of PAH associated with a congenital heart disease.

One aspect of the present invention pertains to compounds of the present invention for use in a method of treatment of PAH associated with a congenital heart disease selected from: atrial septic defect (ASD), ventricular septic defect (VSD) and patent ductus arteriosus.

One aspect of the present invention pertains to compounds of the present invention for use in a method of treatment of PAH associated with portal hypertension.

One aspect of the present invention pertains to compounds of the present invention for use in a method of treatment of PAH associated with HIV infection.

One aspect of the present invention pertains to compounds of the present invention for use in a method of treatment of PAH associated with ingestion of a drug or toxin.

One aspect of the present invention pertains to compounds of the present invention for use in a method of treatment of PAH associated with hereditary hemorrhagic telangiectasia.

One aspect of the present invention pertains to compounds of the present invention for use in a method of treatment of PAH associated with splenectomy.

One aspect of the present invention pertains to compounds of the present invention for use in a method of treatment of PAH associated with significant venous or capillary involvement.

One aspect of the present invention pertains to compounds of the present invention for use in a method of treatment of PAH associated with pulmonary veno-occlusive disease (PVOD).

One aspect of the present invention pertains to compounds of the present invention for use in a method of treatment of PAH associated with pulmonary capillary hemangiomatosis (PCH).

One aspect of the present invention pertains to compounds of the present invention for use in a method of treatment of platelet aggregation.

One aspect of the present invention pertains to compounds of the present invention for use in a method of treatment of: coronary artery disease, myocardial infarction, transient ischemic attack, angina, stroke, ischemia-reperfusion injury, restenosis or atrial fibrillation.

One aspect of the present invention pertains to compounds of the present invention for use in a method of treatment of blood clot formation in an angioplasty or coronary bypass surgery individual.

One aspect of the present invention pertains to compounds of the present invention for use in a method of treatment of blood clot formation in an individual suffering from atrial fibrillation.

One aspect of the present invention pertains to compounds of the present invention for use in a method of treatment of atherosclerosis.

One aspect of the present invention pertains to compounds of the present invention for use in a method of treatment of atherothrombosis.

One aspect of the present invention pertains to compounds of the present invention for use in a method of treatment of asthma.

One aspect of the present invention pertains to compounds of the present invention for use in a method of treatment of a symptom of asthma.

One aspect of the present invention pertains to compounds of the present invention for use in a method of treatment of a diabetic-related disorder.

One aspect of the present invention pertains to compounds of the present invention for use in a method of treatment of diabetic peripheral neuropathy.

One aspect of the present invention pertains to compounds of the present invention for use in a method of treatment of diabetic nephropathy.

One aspect of the present invention pertains to compounds of the present invention for use in a method of treatment of diabetic retinopathy.

One aspect of the present invention pertains to compounds of the present invention for use in a method of treatment of glaucoma or other disease of the eye with abnormal intraocular pressure. In some embodiments the abnormal intraocular pressure is increased intraocular pressure.

One aspect of the present invention pertains to compounds of the present invention for use in a method of treatment of hypertension.

One aspect of the present invention pertains to compounds of the present invention for use in a method of treatment of hypertension intended to confer protection against cerebral ischemia.

One aspect of the present invention pertains to compounds of the present invention for use in a method of treatment of inflammation.

One aspect of the present invention pertains to compounds of the present invention for use in a method of treatment of an inflammatory disease.

One aspect of the present invention pertains to compounds of the present invention for use in a method of treatment of an inflammatory disease selected from: psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis, chronic obstructive pulmonary disorder (COPD) and asthma.

One aspect of the present invention pertains to compounds of the present invention for use in a method of modulating the activity of a PGI2 receptor.

One aspect of the present invention pertains to compounds of the present invention for use in a method of agonizing a PGI2 receptor.

One aspect of the present invention pertains to compounds of the present invention for use in a method of treatment of PAH selected from: idiopathic PAH; familial PAH; PAH associated with a collagen vascular disease selected from: scleroderma, CREST syndrome, systemic lupus erythematosus (SLE), rheumatoid arthritis, Takayasu's arteritis, polymyositis, and dermatomyositis; PAH associated with a congenital heart disease selected from: atrial septic defect (ASD), ventricular septic defect (VSD) and patent ductus arteriosus in an individual; PAH associated with portal hypertension; PAH associated with HIV infection; PAH associated with ingestion of a drug or toxin; PAH associated with hereditary hemorrhagic telangiectasia; PAH associated with splenectomy; PAH associated with significant venous or capillary involvement; PAH associated with pulmonary veno-occlusive disease (PVOD); and PAH associated with pulmonary capillary hemangiomatosis (PCH).

One aspect of the present invention pertains to compounds of the present invention for use in a method of treatment of a disorder selected from: platelet aggregation, coronary artery disease, myocardial infarction, transient ischemic attack, angina, stroke, ischemia-reperfusion injury, restenosis, atrial fibrillation, blood clot formation, atherosclerosis, atherothrombosis, asthma, a symptom of asthma, a diabetic-related disorder, diabetic peripheral neuropathy, diabetic nephropathy, diabetic retinopathy, glaucoma or other disease of the eye with abnormal intraocular pressure, hypertension, inflammation, psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, type 1 diabetes, type 2 diabetes, sepsis and chronic obstructive pulmonary disorder (COPD).

One aspect of the present invention pertains to compounds for preparing a composition comprising admixing a compound of the present invention and a pharmaceutically acceptable carrier.

These and other aspects of the invention disclosed herein will be set forth in greater detail as the patent disclosure proceeds.

DETAILED DESCRIPTION OF THE INVENTION

Definitions

Figure 1:
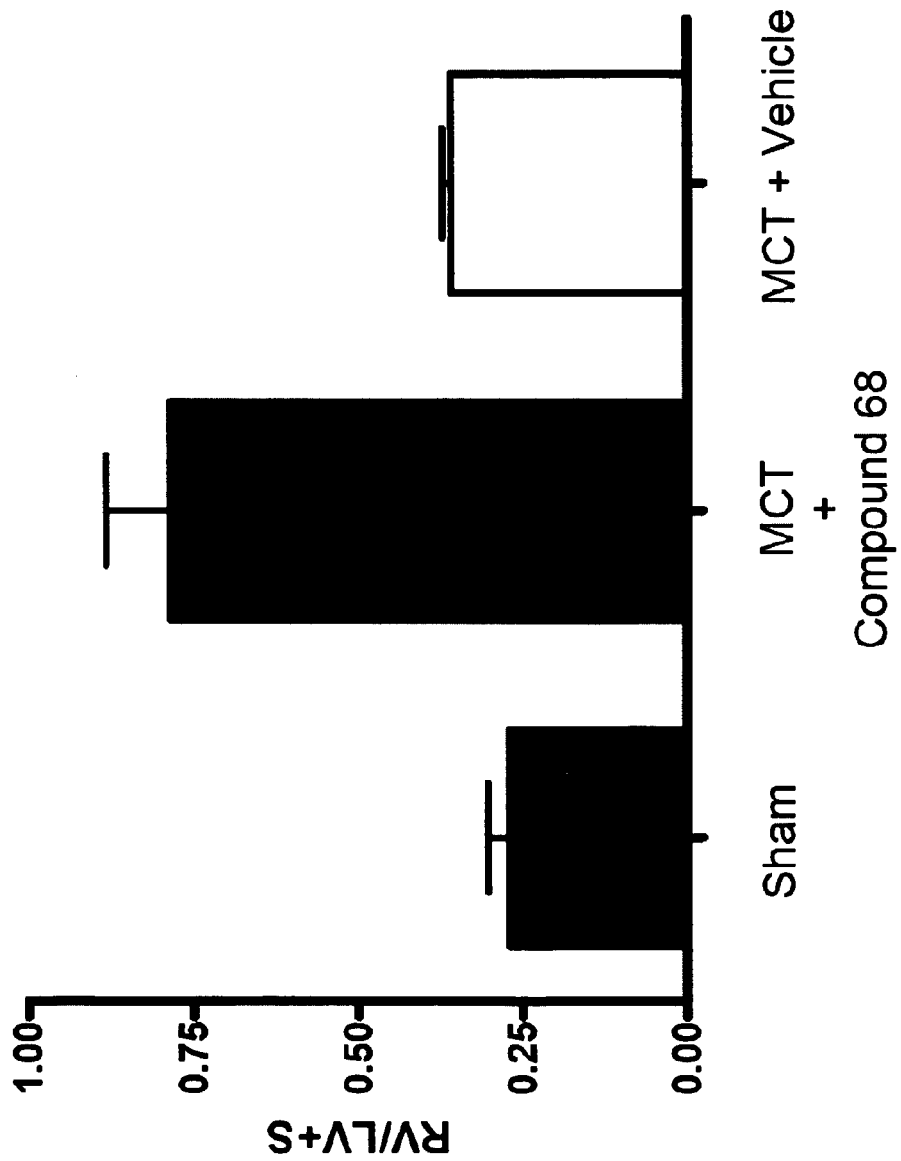
FIG. 1 shows the results of an experiment which measured the ability of Compound 68 to inhibit the right ventricle hypertrophic response to MCT-induced pulmonary arterial hypertension in rat at 30 mg/kg.
Figure 2:
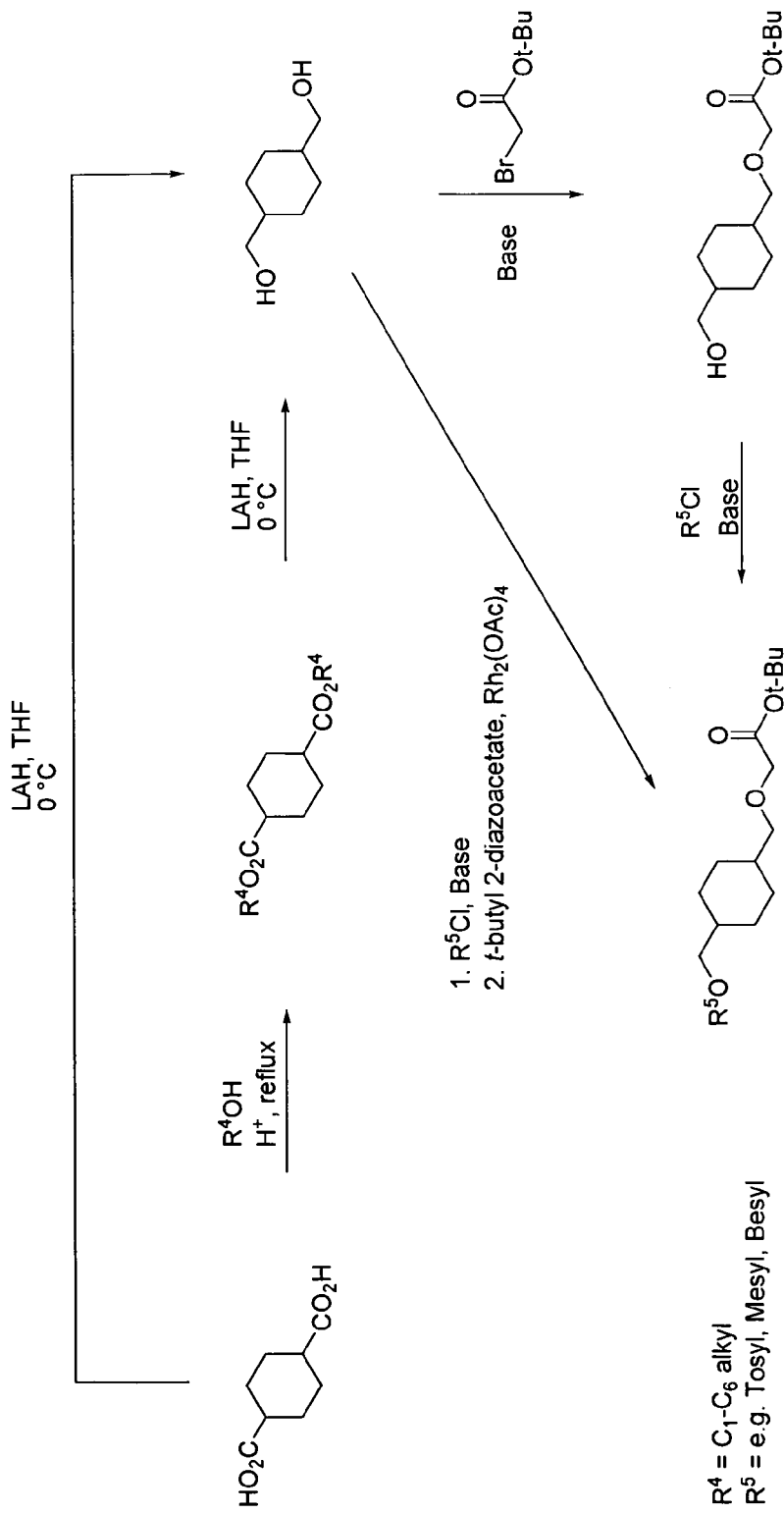
FIG. 2 depicts a general method for preparing intermediates useful in the synthesis of compounds of the present invention. Cyclohexane-1,4-dicarboxylic acid is first converted to the diol either directly or via an ester. The diol is then converted to a sulfonate ester intermediate by either by alkylation with tert-butyl bromoacetate followed activation with a sulfonyl chloride or alternatively by treatment first with a sulfonyl chloride followed by alkylation with tert-butyl 2-diazoacetate in the presence of diacetoxyrhodium.
Figure 3:
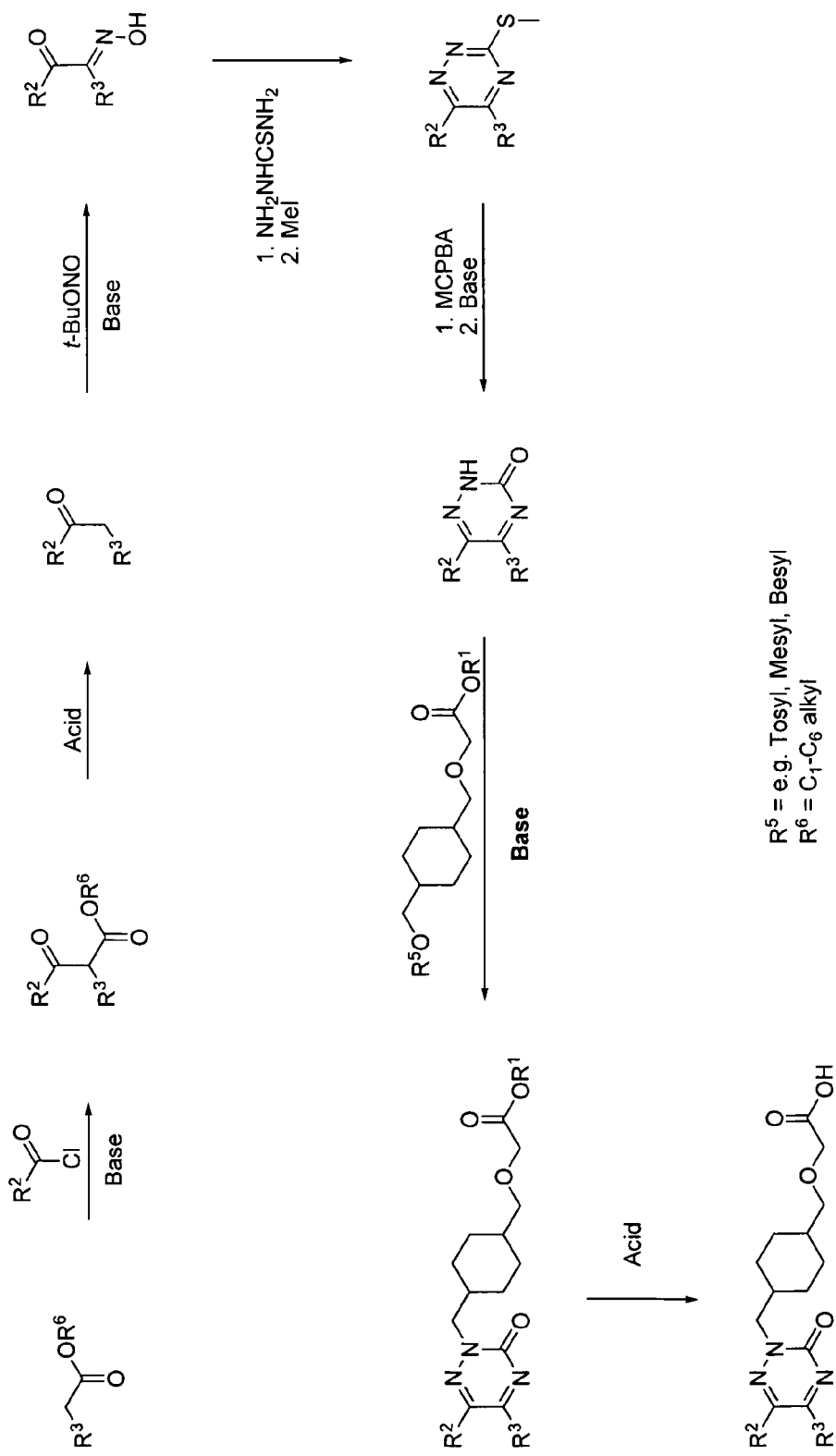
FIG. 3 depicts a general method for preparing 1,2,4-triazin-3(2H)-ones of the present invention. In the first step, an acetic acid derivative is reacted with an acid chloride in the presence of base to give a β-ketoester derivative. This undergoes acid mediated hydrolysis/decarboxylation to give an ethanone derivative. Reaction with tert-butyl nitrite in the presence of base gives an oxime which is reacted with hydrazinecarbothioamide followed by iodomethane to give a 3-(methylthio)-1,2,4-triazine intermediate. This is converted to the triazinone by treatment with MCPBA and then base. The triazinone is coupled to the sulfonate ester intermediate described in FIG. 2 to give an ester of Formula Ia which is hydrolyzed with acid to give a carboxylic acid of Formula Ia.
Figure 4:
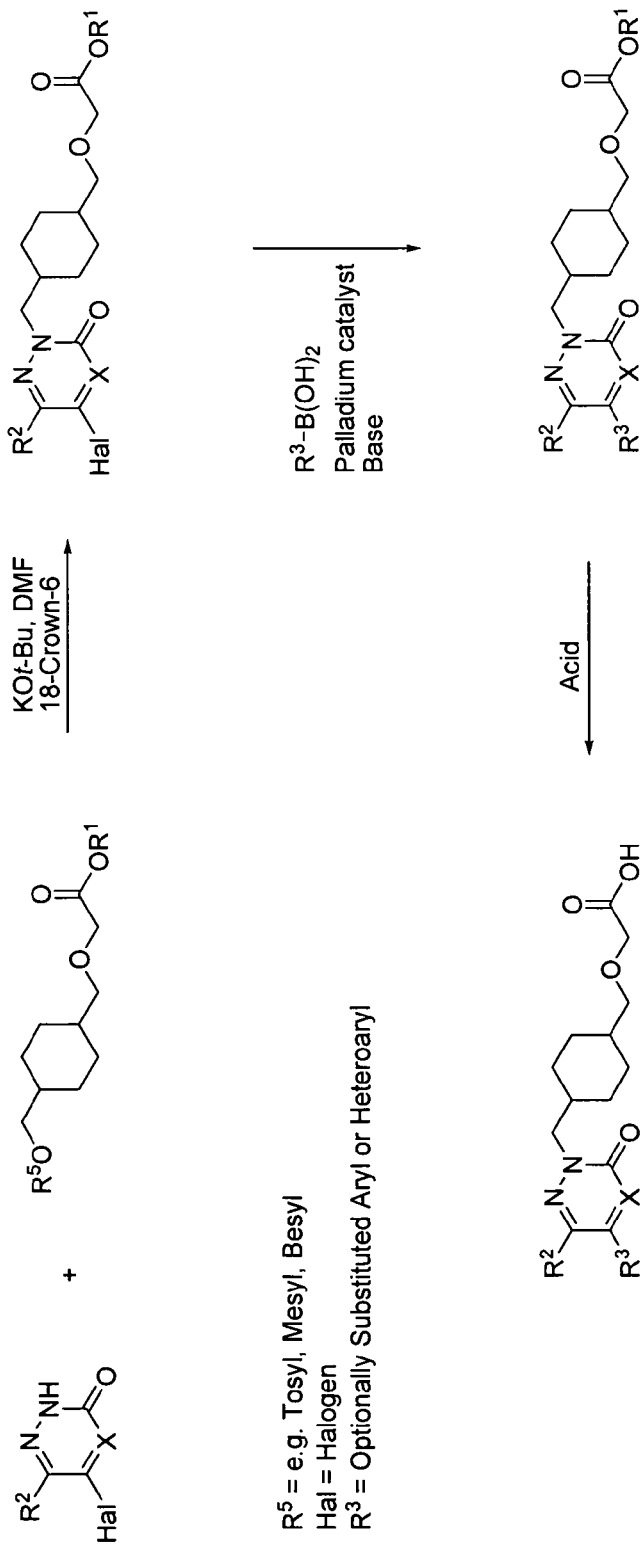
FIG. 4 depicts another general method for preparing compounds of the present invention. In this method, a 5-halo-1,2,4-triazin-3(2H)-ones or a 5-halopyridazin-3(2H)-one intermediate is reacted with the sulfonate ester described in FIG. 2 in the presence of potassium tert-butoxide and 18-crown-6 in DMF. The product undergoes a palladium catalyzed coupling to an aryl or heteroaryl boronic acid derivative to give an ester of Formula Ia which is hydrolyzed with acid to give a carboxylic acid of Formula Ia.
Figure 5:
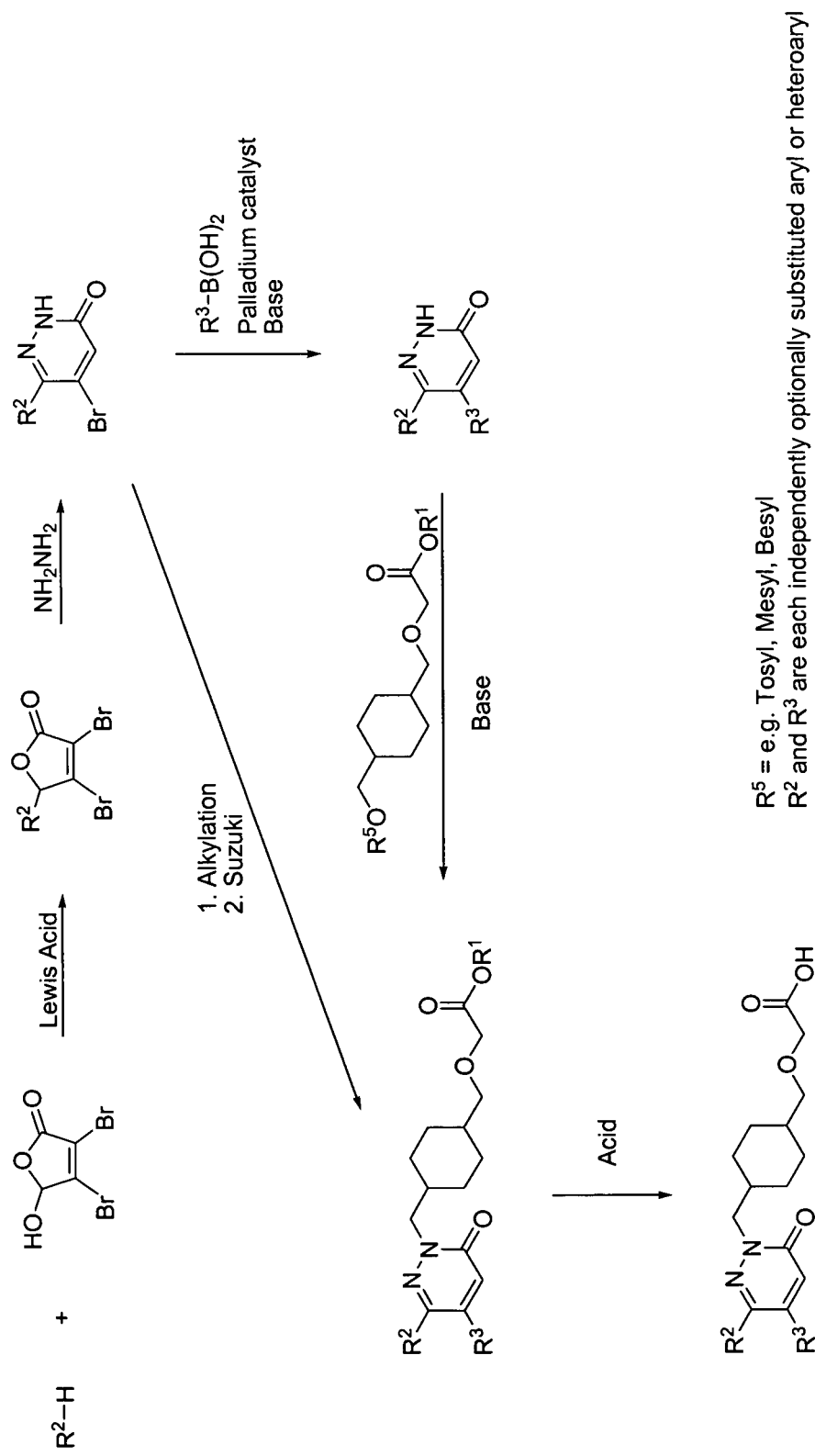
FIG. 5 depicts another general method for preparing compounds of the present invention. Certain pyridazinone intermediates are prepared by reaction of 3,4-dibromo-5-hydroxyfuran-2(5H)-one with an aryl or heteroaryl derivative in the presence of a Lewis acid followed by treatment with hydrazine. The resulting pyridazinone is reacted with a boronic acid derivative in the presence of a palladium catalyst. The product of that reaction is coupled to the sulfonate ester intermediate described in FIG. 2 to give an ester of Formula Ia. This is hydrolyzed with acid to give a carboxylic acid of Formula Ia. Alternatively, the order in which the pyridazinone is coupled to the boronic acid and the sulfonate ester may be reversed.
Figure 6:
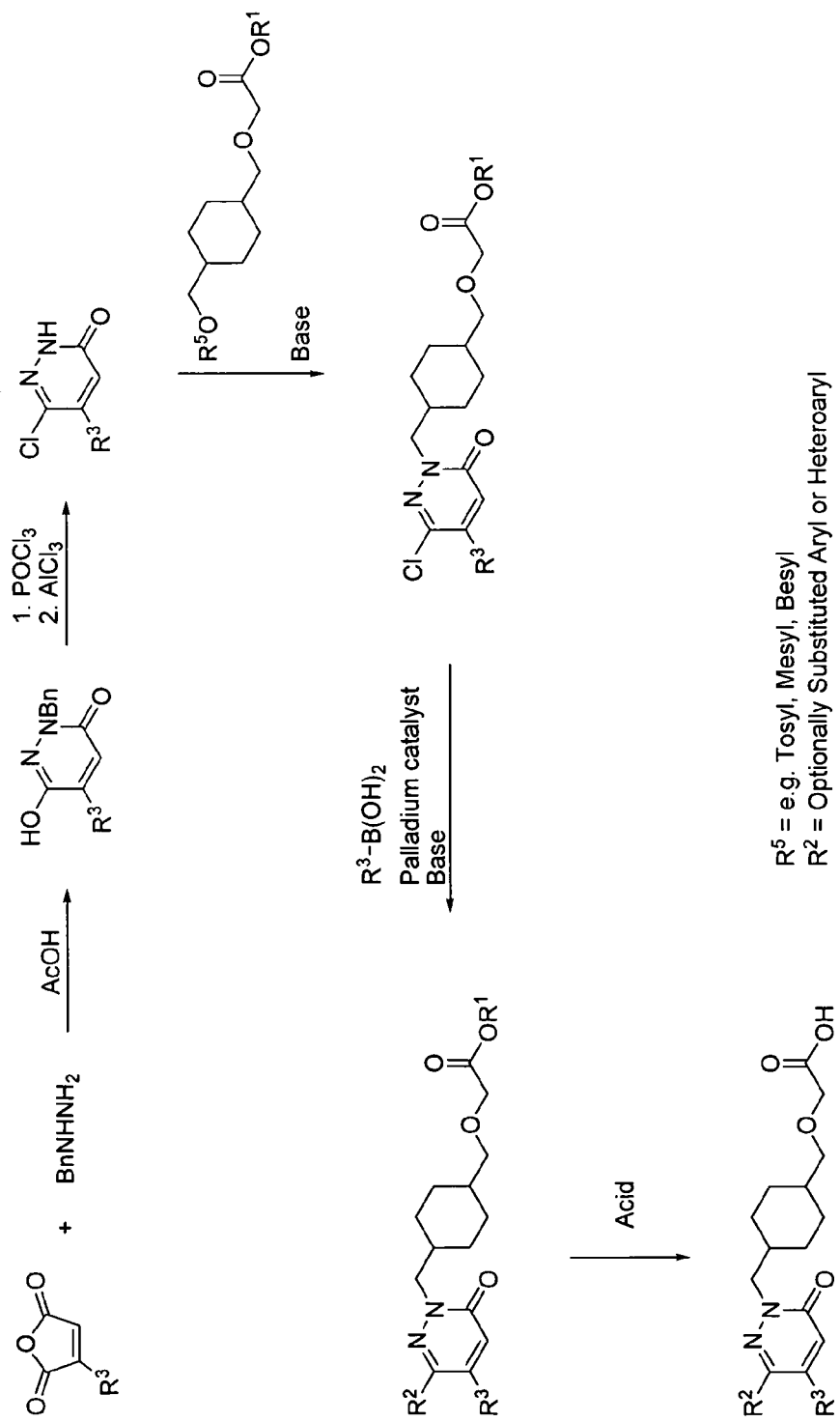
FIG. 6 depicts another general method for preparing compounds of the present invention. Certain furan-2,5-dione derivatives may be converted to hydroxypyridazinone intermediates by reaction with benzylhydrazine in acetic acid. Subsequent conversion to the chloride and removal of the benzyl group is achieved by treatment with phosphorous oxychloride followed by aluminum chloride. The resulting chloropyridazinone intermediate is coupled to the sulfonate ester intermediate described in FIG. 2 and treated with a boronic acid in the presence of a palladium catalyst to give an ester of Formula Ia. This is hydrolyzed with acid to give a carboxylic acid of Formula Ia.

For clarity and consistency, the following definitions will be used throughout this patent document.

The term "agonists" is intended to mean moieties that interact and activate the receptor, such as, the PGI2 receptor and initiate a physiological or pharmacological response characteristic of that receptor. For example, when moieties activate the intracellular response upon binding to the receptor, or enhance GTP binding to membranes.

The term "contact or contacting" is intended to mean bringing the indicated moieties together, whether in an in vitro system or an in vivo system. Thus, "contacting" a PGI2 receptor with a compound of the invention includes the administration of a compound of the present invention to an individual, preferably a human, having a PGI2 receptor, as well as, for example, introducing a compound of the invention into a sample containing a cellular or more purified preparation containing a PGI2 receptor.

The term "hydrate" as used herein means a compound of the invention or a salt thereof, that further includes a stoichiometric or non-stoichiometric amount of water bound by non-covalent intermolecular forces.

The terms "including" and "such as" are illustrative and not limitative.

The term "in need of treatment" and the term "in need thereof," when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates and most preferably humans.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates and hydrates of compounds of the present invention; whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician or caregiver; or in an individual, which includes one or more of the following:

(1) Preventing the disease; for example, preventing a disease, condition or disorder in an individual that may be predisposed to the disease, condition or disorder but does not yet experience or display the pathology or symptomatology of the disease;

(2) Inhibiting the disease; for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "$C_1$-$C_6$ alkoxy" is intended to mean a $C_1$-$C_6$ alkyl radical, as defined herein, attached directly to an oxygen atom. Some embodiments are 1 to 5 carbons; some embodiments are 1 to 4 carbons; some embodiments are 1 to 3 carbons; and some embodiments are 1 or 2 carbons. Examples include methoxy, ethoxy, n-propoxy, isopropoxy, n-butoxy, t-butoxy, isobutoxy, sec-butoxy and the like.

The term "$C_1$-$C_6$ alkyl" is intended to mean a straight or branched carbon radical containing 1 to 6 carbons. Some embodiments are 1 to 5 carbons. Some embodiments are 1 to 4 carbons. Some embodiments are 1 to 3 carbons. Some embodiments are 1 or 2 carbons. Some embodiments are 1 carbon. Examples of an alkyl include, but are not limited to, methyl, ethyl, n-propyl, isopropyl, n-butyl, sec-butyl, isobutyl, t-butyl, pentyl, isopentyl, t-pentyl, neo-pentyl, 1-methylbutyl [i.e., —CH($CH_3$)$CH_2$$CH_2$$CH_3$], 2-methylbutyl [i.e., —$CH_2$CH($CH_3$)$CH_2$$CH_3$], n-hexyl and the like.

The term "$C_1$-$C_6$ alkylthio" is intended to mean a $C_1$-$C_6$ alkyl radical attached to a sulfur atom (i.e., —S—) wherein the alkyl radical has the same definition as described herein. Examples include, but are not limited to, methylsulfanyl (i.e., $CH_3$S—), ethylsulfanyl, n-propylsulfanyl, iso-propylsulfanyl, n-butylsulfanyl, sec-butylsulfanyl, iso-butylsulfanyl, t-butylsulfanyl, and the like.

The term "aryl" is intended to mean an aromatic ring radical containing 6 to 10 ring carbons. Examples include phenyl and naphthyl. In some embodiments aryl is intended to mean phenyl.

The term "18-crown-6" is intended to mean 1,4,7,10,13,16-hexaoxacyclooctadecane.

The term "$C_1$-$C_6$ haloalkyl" is intended to mean a $C_1$-$C_6$ alkyl group, defined herein, wherein the alkyl is substituted with one halogen up to fully substituted and a fully substituted $C_1$-$C_6$ haloalkyl can be represented by the formula $C_nL_{2n+1}$ wherein L is a halogen and "n" is 1, 2, 3, 4, 5 or 6. When more than one halogen is present then they may be the same or different and selected from the group consisting of F, Cl, Br and I, preferably F. Some embodiments are 1 to 5 carbons, some embodiments are 1 to 4 carbons, some embodiments are 1 to 3 carbons, and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl and the like.

The term "halogen" or "halo" is intended to mean to a fluoro, chloro, bromo or iodo group.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N wherein the N can be optionally substituted with H, $C_1$-$C_4$ acyl or $C_1$-$C_4$ alkyl. Some embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Some embodiments contain 8 to 14 ring atoms for example carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

Compounds of the Invention:

One aspect of the present invention pertains to certain compounds as shown in Formula Ia:

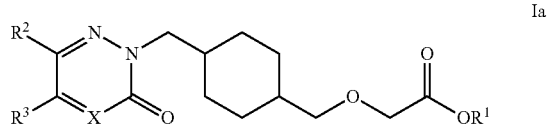

and pharmaceutically acceptable salts, solvates and hydrates thereof wherein $R^1$, $R^2$, $R^3$ and X have the same definitions as described herein, supra and infra.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$, $R^2$, $R^3$ and X) contained within the generic chemical formulae described herein, for example, Ia, Ic, Ie, Ig, Ii, etc., are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of Formula Ia and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula Ia and formulae used throughout this disclosure are intended to represent all individual enantiomers and mixtures thereof, unless stated or shown otherwise.

It is understood and appreciated that compounds of Formula Ia exist as meso isomers. Such meso isomers may be referred to as cis and trans. Certain cis meso isomers of compounds of Formula Ia are named herein using the prefix (1s,4s) and certain trans meso isomers of compounds of Formula Ia are named herein using the prefix (1r,4r) as shown below.

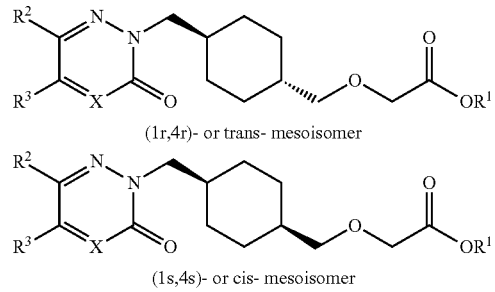

(1r,4r)- or trans- mesoisomer (1s,4s)- or cis- mesoisomer

The Group $R^1$:

In some embodiments, $R^1$ is selected from: H and $C_1$-$C_6$ alkyl.

In some embodiments, $R^1$ is H.

In some embodiments, $R^1$ is $C_1$-$C_6$ alkyl.

In some embodiments, $R^1$ is tert-butyl.

The Group $R^2$:

In some embodiments, $R^2$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: chloro, ethyl, fluoro, isopropyl, methoxy, methyl, methylthio, phenyl and trifluoromethyl.

In some embodiments, $R^2$ is selected from: methyl, phenyl, pyridinyl, thiophen-2-yl and thiophen-3-yl; wherein said methyl, phenyl, pyridinyl, thiophen-2-yl and thiophen-3-yl are each optionally substituted with one or more substituents each independently selected from: chloro, ethyl, fluoro, isopropyl, methoxy, methyl, methylthio, phenyl and trifluoromethyl.

In some embodiments, $R^2$ is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl) phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl.

In some embodiments, $R^2$ is 2,3-difluorophenyl.
In some embodiments, $R^2$ is 2-chlorophenyl.
In some embodiments, $R^2$ is 2-fluoro-4-methylphenyl.
In some embodiments, $R^2$ is 2-fluorophenyl.
In some embodiments, $R^2$ is 2-methoxyphenyl.
In some embodiments, $R^2$ is 3-chlorophenyl.
In some embodiments, $R^2$ is 3-fluoro-4-methylphenyl.
In some embodiments, $R^2$ is 3-fluoro-5-methoxyphenyl.
In some embodiments, $R^2$ is 3-fluorophenyl.
In some embodiments, $R^2$ is 3-methoxyphenyl.
In some embodiments, $R^2$ is 4-(methylthio)phenyl.
In some embodiments, $R^2$ is 4-(trifluoromethyl)phenyl.
In some embodiments, $R^2$ is 4-chloro-2-fluorophenyl.
In some embodiments, $R^2$ is 4-chloro-3-fluorophenyl.
In some embodiments, $R^2$ is 4-chlorophenyl.
In some embodiments, $R^2$ is 4-ethylphenyl.
In some embodiments, $R^2$ is 4-fluorophenyl.
In some embodiments, $R^2$ is 4-isopropylphenyl.
In some embodiments, $R^2$ is 4-methoxyphenyl.
In some embodiments, $R^2$ is 5-methylpyridin-3-yl.
In some embodiments, $R^2$ is 6-chloropyridin-3-yl.
In some embodiments, $R^2$ is 6-methylpyridin-3-yl.
In some embodiments, $R^2$ is benzhydryl.
In some embodiments, $R^2$ is phenyl.
In some embodiments, $R^2$ is p-tolyl.
In some embodiments, $R^2$ is pyridin-3-yl.
In some embodiments, $R^2$ is pyridin-4-yl.
In some embodiments, $R^2$ is thiophen-2-yl.
In some embodiments, $R^2$ is thiophen-3-yl.

The Group $R^3$:

In some embodiments, $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy and halogen.

In some embodiments, $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: chloro, fluoro, methoxy and methyl.

In some embodiments, $R^3$ is selected from: H, 1H-pyrazol-4-yl, phenyl, pyridinyl and thiophen-2-yl; wherein said phenyl, pyridinyl and thiophen-2-yl are each optionally substituted with one or more substituents each independently selected from: chloro, fluoro, methoxy and methyl.

In some embodiments, $R^3$ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloropyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

In some embodiments, $R^3$ is H.
In some embodiments, $R^3$ is 1H-pyrazol-4-yl.
In some embodiments, $R^3$ is 2,3-difluorophenyl.
In some embodiments, $R^3$ is 2-chlorophenyl.
In some embodiments, $R^3$ is 2-chloropyridin-4-yl.
In some embodiments, $R^3$ is 2-fluoro-3-methoxyphenyl.
In some embodiments, $R^3$ is 2-fluoropyridin-3-yl.
In some embodiments, $R^3$ is 2-fluoropyridin-4-yl.
In some embodiments, $R^3$ is 2-methoxyphenyl.
In some embodiments, $R^3$ is 2-methylpyridin-4-yl.
In some embodiments, $R^3$ is 3,4-dichlorophenyl.
In some embodiments, $R^3$ is 3,5-dichlorophenyl.
In some embodiments, $R^3$ is 3-chloro-2-fluorophenyl.
In some embodiments, $R^3$ is 3-chloro-4-fluorophenyl.
In some embodiments, $R^3$ is 3-chlorophenyl.
In some embodiments, $R^3$ is 3-fluoro-5-methoxyphenyl.
In some embodiments, $R^3$ is 3-fluorophenyl.
In some embodiments, $R^3$ is 3-methoxyphenyl.
In some embodiments, $R^3$ is 4-chlorophenyl.
In some embodiments, $R^3$ is 4-fluorophenyl.
In some embodiments, $R^3$ is 4-methoxyphenyl.
In some embodiments, $R^3$ is 4-methylthiophen-2-yl.
In some embodiments, $R^3$ is 5-chloro-2-fluorophenyl.
In some embodiments, $R^3$ is 5-chloro-pyridin-3-yl.
In some embodiments, $R^3$ is 5-methylpyridin-3-yl.
In some embodiments, $R^3$ is 5-methylthiophen-2-yl.
In some embodiments, $R^3$ is 6-fluoropyridin-3-yl.
In some embodiments, $R^3$ is m-tolyl.
In some embodiments, $R^3$ is phenyl.
In some embodiments, $R^3$ is p-tolyl.
In some embodiments, $R^3$ is pyridin-3-yl.
In some embodiments, $R^3$ is pyridin-4-yl.
In some embodiments, $R^3$ is thiophen-2-yl.

The Group X:

In some embodiments, X is selected from: N and CH.
In some embodiments, X is N.
In some embodiments, X is CH.

Certain Combinations of the Present Invention:

In some embodiments, $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one, two, three, four or five substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one, two, three or four substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one, two or three substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or two substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one substituent selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or more substituents each independently selected from: chloro, ethyl, fluoro, isopropyl, methoxy, methyl, methylthio, phenyl and trifluoromethyl.

In some embodiments, $R^2$ and $R^3$ are each independently selected from: H, 1H-pyrazol-4-yl, methyl, phenyl, pyridinyl, thiophen-2-yl and thiophen-3-yl; wherein said methyl, phenyl, pyridinyl, thiophen-2-yl and thiophen-3-yl are each optionally substituted with one or more substituents each independently selected from: chloro, ethyl, fluoro, isopropyl, methoxy, methyl, methylthio, phenyl and trifluoromethyl.

In some embodiments, $R^2$ and $R^3$ are each independently selected from: H, 1H-pyrazol-4-yl, 2,3-difluorophenyl, 2-chlorophenyl, 2-chloropyridin-4-yl, 2-fluoro-3-methoxyphenyl, 2-fluoro-4-methylphenyl, 2-fluorophenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 4-methylthiophen-2-yl, 5-chloro-2-fluorophenyl, 5-chloro-pyridin-3-yl, 5-methylpyridin-3-yl, 5-methylpyridin-3-yl, 5-methylthiophen-2-yl, 6-chloropyridin-3-yl, 6-fluoropyridin-3-yl, 6-methylpyridin-3-yl, benzhydryl, m-tolyl, phenyl, p-tolyl, pyridin-3-yl, pyridin-4-yl, thiophen-2-yl and thiophen-3-yl.

One aspect of the present invention encompasses certain cyclohexane derivatives selected from compounds of Formula Ic and pharmaceutically acceptable salts, solvates and hydrates thereof:

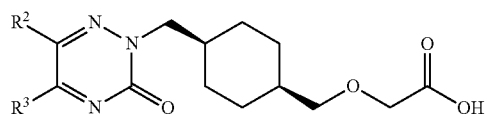

Ic wherein:

$R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen; and $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy and halogen.

One aspect of the present invention encompasses certain cyclohexane derivatives selected from compounds of Formula Ic and pharmaceutically acceptable salts, solvates and hydrates thereof:

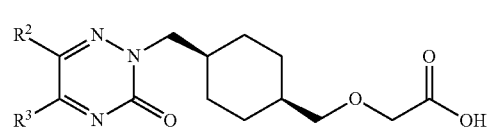

Ic wherein:

$R^2$ is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl; and $R^3$ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

One aspect of the present invention encompasses certain cyclohexane derivatives selected from compounds of Formula Ie and pharmaceutically acceptable salts, solvates and hydrates thereof:

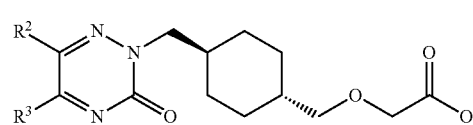

Ie wherein:

$R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen; and $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy and halogen.

One aspect of the present invention encompasses certain cyclohexane derivatives selected from compounds of Formula Ie and pharmaceutically acceptable salts, solvates and hydrates thereof:

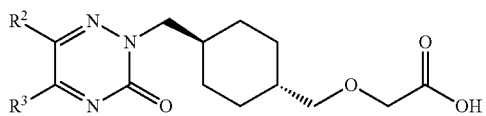

wherein:

R² is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl; and R³ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

One aspect of the present invention encompasses certain cyclohexane derivatives selected from compounds of Formula Ig and pharmaceutically acceptable salts, solvates and hydrates thereof:

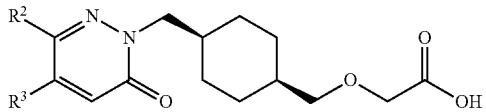

wherein:

R² is selected from: C₁-C₈ alkyl, aryl and heteroaryl; wherein said C₁-C₈ alkyl, aryl and heteroaryl are each optionally substituted with one or more substituents each independently selected from: C₁-C₈ alkyl, C₁-C₈ alkoxy, C₁-C₈ alkylthio, aryl, C₁-C₈ haloalkyl and halogen; and R³ is selected from: H, C₁-C₈ alkyl, aryl and heteroaryl; wherein said C₁-C₈ alkyl, aryl and heteroaryl are each optionally substituted with one or more substituents each independently selected from: C₁-C₈ alkyl, C₁-C₈ alkoxy and halogen.

One aspect of the present invention encompasses certain cyclohexane derivatives selected from compounds of Formula Ig and pharmaceutically acceptable salts, solvates and hydrates thereof:

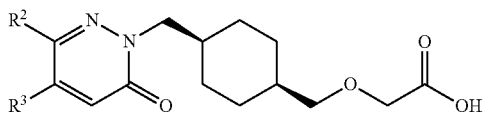

wherein:

R² is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl; and R³ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

One aspect of the present invention encompasses certain cyclohexane derivatives selected from compounds of Formula Ii and pharmaceutically acceptable salts, solvates and hydrates thereof:

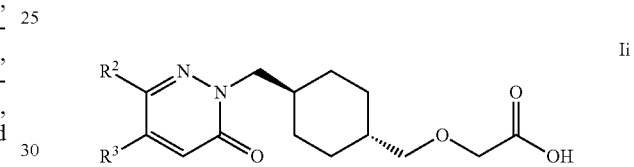

wherein:

R² is selected from: C₁-C₈ alkyl, aryl and heteroaryl; wherein said C₁-C₈ alkyl, aryl and heteroaryl are each optionally substituted with one or more substituents each independently selected from: C₁-C₈ alkyl, C₁-C₈ alkoxy, C₁-C₈ alkylthio, aryl, C₁-C₈ haloalkyl and halogen; and R³ is selected from: H, C₁-C₈ alkyl, aryl and heteroaryl; wherein said C₁-C₈ alkyl, aryl and heteroaryl are each optionally substituted with one or more substituents each independently selected from: C₁-C₈ alkyl, C₁-C₈ alkoxy and halogen.

One aspect of the present invention encompasses certain cyclohexane derivatives selected from compounds of Formula Ii and pharmaceutically acceptable salts, solvates and hydrates thereof:

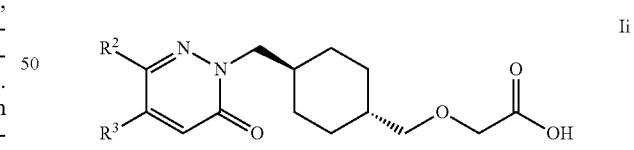

wherein:

R² is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl; and R³ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

Some embodiments of the present invention include every combination of one or more compounds selected from the following group shown in TABLE A.

TABLE A

| Cpd No. | Chemical Structure | Chemical Name |
|---|---|---|
| 1 | 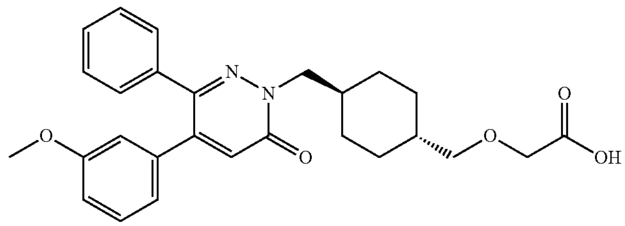 [SMILES: COc1cccc(-c2cc(=O)n(C[C@H]3CC[C@H](COCC(=O)O)CC3)nc2-c2ccccc2)c1] | 2-(((1r,4r)-4-((4-(3-methoxyphenyl)-6-oxo-3-phenylpyridazin-1(6H)-yl)methyl)cyclohexyl)methoxy)acetic acid |
| 2 | 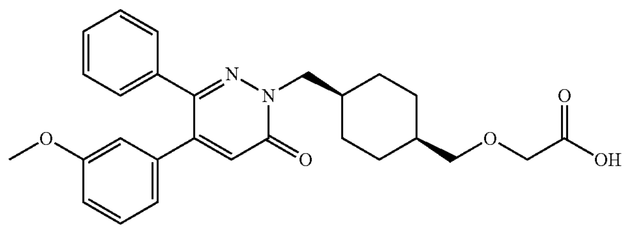 [SMILES: COc1cccc(-c2cc(=O)n(C[C@H]3CC[C@@H](COCC(=O)O)CC3)nc2-c2ccccc2)c1] | 2-(((1s,4s)-4-((4-(3-methoxyphenyl)-6-oxo-3-phenylpyridazin-1(6H)-yl)methyl)cyclohexyl)methoxy)acetic acid |
| 3 | 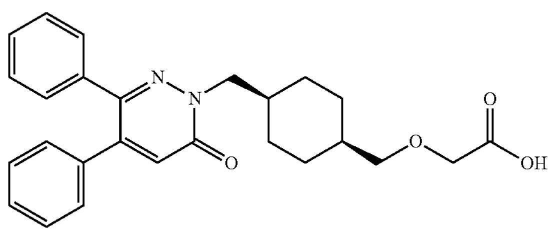 [SMILES: O=C(O)COC[C@H]1CC[C@@H](Cn2nc(-c3ccccc3)c(-c3ccccc3)cc2=O)CC1] | 2-(((1s,4s)-4-((6-oxo-3,4-diphenylpyridazin-1(6H)-yl)methyl)cyclohexyl)methoxy)acetic acid |
| 4 | 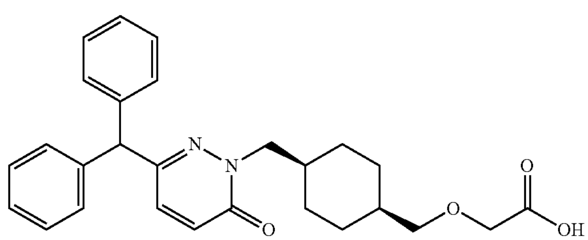 [SMILES: O=C(O)COC[C@H]1CC[C@@H](Cn2nc(C(c3ccccc3)c3ccccc3)ccc2=O)CC1] | 2-(((1s,4s)-4-((3-benzhydryl-6-oxopyridazin-1(6H)-yl)methyl)cyclohexyl)methoxy)acetic acid |
| 5 | 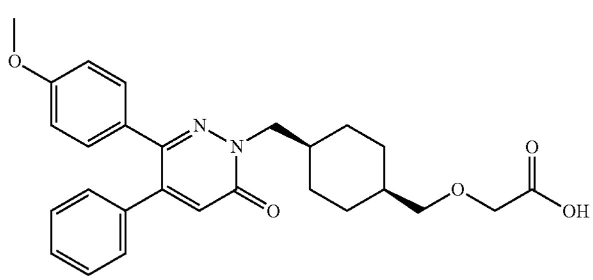 [SMILES: COc1ccc(-c2nn(C[C@H]3CC[C@@H](COCC(=O)O)CC3)c(=O)cc2-c2ccccc2)cc1] | 2-(((1s,4s)-4-((3-(4-methoxyphenyl)-6-oxo-4-phenylpyridazin-1(6H)-yl)methyl)cyclohexyl)methoxy)acetic acid |

TABLE A-continued

| Cpd No. | Chemical Structure | Chemical Name |
|---|---|---|
| 6 | 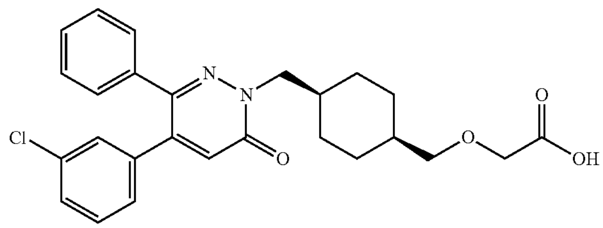 [SMILES: O=C(O)COC[C@H]1CC[C@@H](Cn2nc(-c3ccccc3)c(-c3cccc(Cl)c3)cc2=O)CC1] | 2-(((1s,4s)-4-((4-(3-chlorophenyl)-6-oxo-3-phenylpyridazin-1(6H)-yl)methyl)cyclohexyl)methoxy)acetic acid |
| 7 | 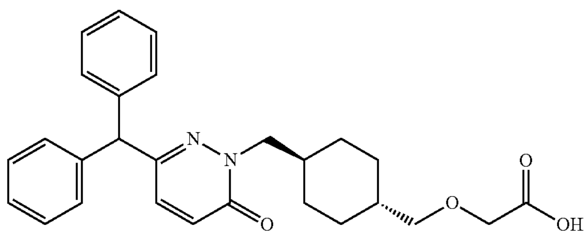 [SMILES: O=C(O)COC[C@H]1CC[C@H](Cn2nc(C(c3ccccc3)c3ccccc3)ccc2=O)CC1] | 2-(((1r,4r)-4-((3-benzhydryl-6-oxopyridazin-1(6H)-yl)methyl)cyclohexyl)methoxy)acetic acid |
| 8 | 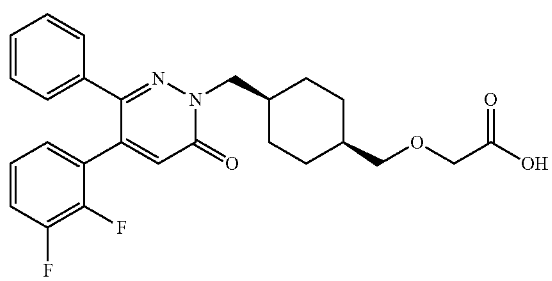 [SMILES: O=C(O)COC[C@H]1CC[C@@H](Cn2nc(-c3ccccc3)c(-c3cccc(F)c3F)cc2=O)CC1] | 2-((1s,4s)-4-((4-(2,3-difluorophenyl)-6-oxo-3-phenylpyridazin-1(6H)-yl)methyl)cyclohexyl)methoxy)acetic acid |
| 9 | 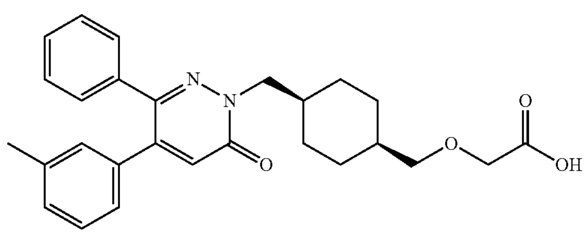 [SMILES: Cc1cccc(-c2cc(=O)n(C[C@H]3CC[C@@H](COCC(=O)O)CC3)nc2-c2ccccc2)c1] | 2-(((1s,4s)-4-((6-oxo-3-phenyl-4-m-tolylpyridazin-1(6H)-yl)methyl)cyclohexyl)methoxy)acetic acid |
| 10 | 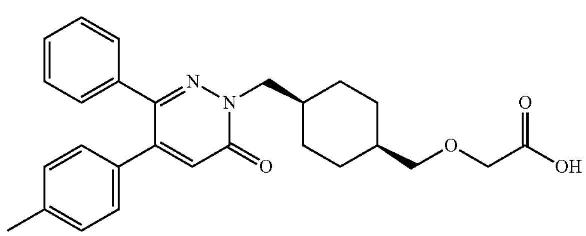 [SMILES: Cc1ccc(-c2cc(=O)n(C[C@H]3CC[C@@H](COCC(=O)O)CC3)nc2-c2ccccc2)cc1] | 2-(((1s,4s)-4-((6-oxo-3-phenyl-4-p-tolylpyridazin-1(6H)-yl)methyl)cyclohexyl)methoxy)acetic acid |
| 11 | 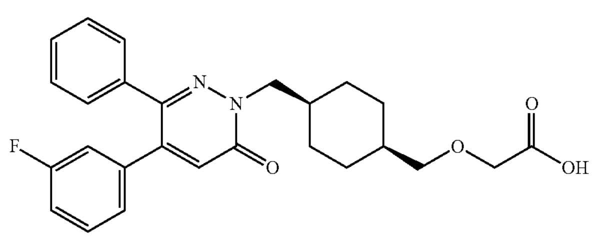 [SMILES: O=C(O)COC[C@H]1CC[C@@H](Cn2nc(-c3ccccc3)c(-c3cccc(F)c3)cc2=O)CC1] | 2-(((1s,4s)-4-((4-(3-fluorophenyl)-6-oxo-3-phenylpyridazin-1(6H)-yl)methyl)cyclohexyl)methoxy)acetic acid |

TABLE A-continued

| Cpd No. | Chemical Structure | Chemical Name |
|---|---|---|
| 12 | 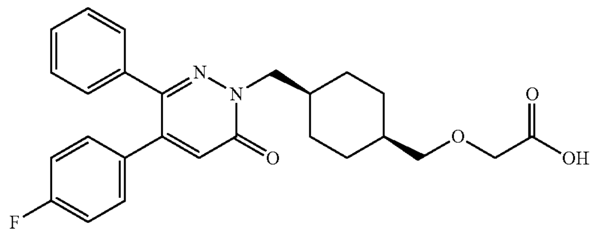 [SMILES: O=C(O)COC[C@H]1CC[C@@H](Cn2nc(-c3ccccc3)c(-c3ccc(F)cc3)cc2=O)CC1] | 2-(((1s,4s)-4-((4-(4-fluorophenyl)-6-oxo-3-phenylpyridazin-1(6H)-yl)methyl)cyclohexyl)methoxy)acetic acid |
| 13 | 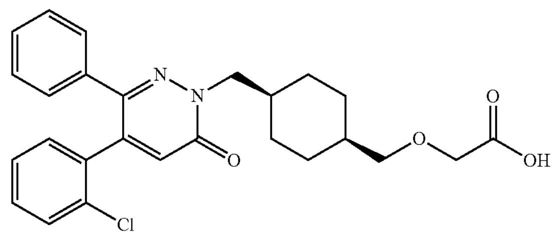 [SMILES: O=C(O)COC[C@H]1CC[C@@H](Cn2nc(-c3ccccc3)c(-c3ccccc3Cl)cc2=O)CC1] | 2-(((1s,4s)-4-((4-(2-chlorophenyl)-6-oxo-3-phenylpyridazin-1(6H)-yl)methyl)cyclohexyl)methoxy)acetic acid |
| 14 | 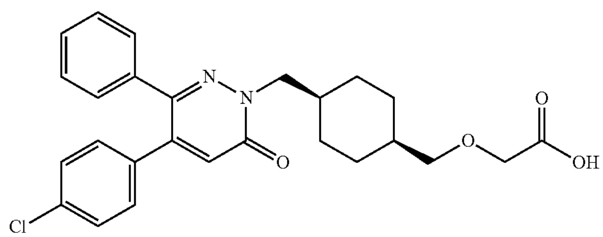 [SMILES: O=C(O)COC[C@H]1CC[C@@H](Cn2nc(-c3ccccc3)c(-c3ccc(Cl)cc3)cc2=O)CC1] | 2-(((1s,4s)-4-((4-(4-chlorophenyl)-6-oxo-3-phenylpyridazin-1(6H)-yl)methyl)cyclohexyl)methoxy)acetic acid |
| 15 | 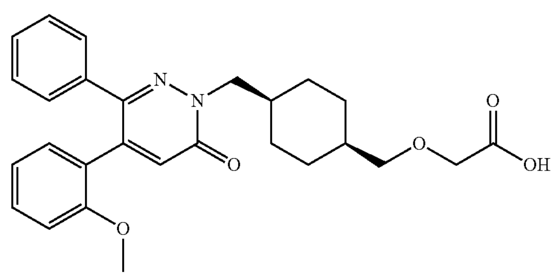 [SMILES: COc1ccccc1-c1cc(=O)n(C[C@H]2CC[C@@H](COCC(=O)O)CC2)nc1-c1ccccc1] | 2-(((1s,4s)-4-((4-(2-methoxyphenyl)-6-oxo-3-phenylpyridazin-1(6H)-yl)methyl)cyclohexyl)methoxy)acetic acid |
| 16 | 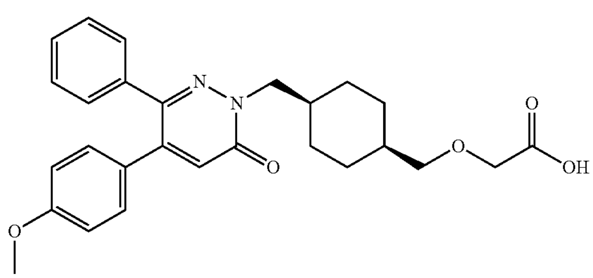 [SMILES: COc1ccc(-c2cc(=O)n(C[C@H]3CC[C@@H](COCC(=O)O)CC3)nc2-c2ccccc2)cc1] | 2-(((1s,4s)-4-((4-(4-methoxyphenyl)-6-oxo-3-phenylpyridazin-1(6H)-yl)methyl)cyclohexyl)methoxy)acetic acid |
| 17 | 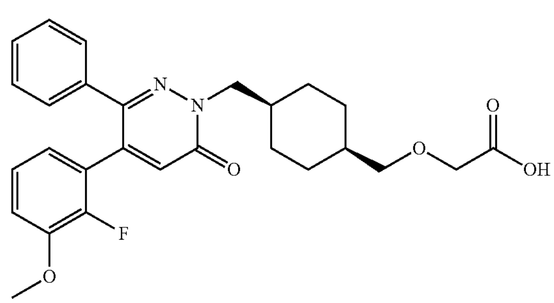 [SMILES: COc1cccc(-c2cc(=O)n(C[C@H]3CC[C@@H](COCC(=O)O)CC3)nc2-c2ccccc2)c1F] | 2-(((1s,4s-((4-(2-fluoro-3-methoxyphenyl)-6-oxo-3-phenylpyridazin-1(6H)-yl)methyl)cyclohexyl)methoxy)acetic acid |

TABLE A-continued

| Cpd No. | Chemical Structure | Chemical Name |
|---|---|---|
| 18 | 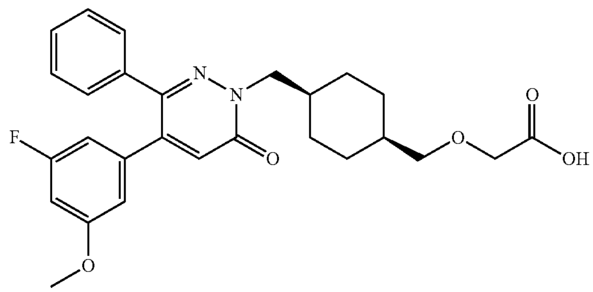 [SMILES: COc1cc(F)cc(-c2cc(=O)n(C[C@H]3CC[C@@H](COCC(=O)O)CC3)nc2-c2ccccc2)c1] | 2-(((1s,4s)-4-((4-(3-fluoro-5-methoxyphenyl)-6-oxo-3-phenylpyridazin-1(6H)-yl)methyl)cyclohexyl)methoxy)acetic acid |
| 19 | 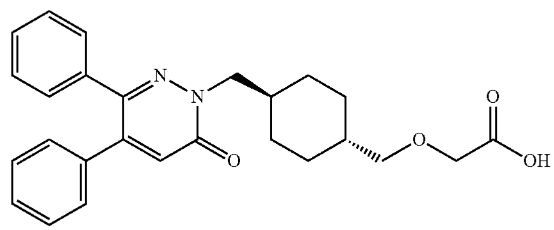 [SMILES: O=C(O)COC[C@H]1CC[C@H](Cn2nc(-c3ccccc3)c(-c3ccccc3)cc2=O)CC1] | 2-(((1r,4r)-4-((6-oxo-3,4-diphenylpyridazin-1(6H)-yl)methyl)cyclohexyl)methoxy)acetic acid |
| 20 | 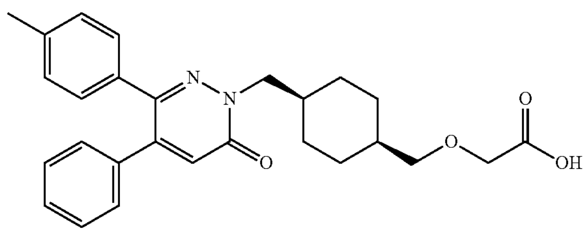 [SMILES: Cc1ccc(-c2nn(C[C@H]3CC[C@@H](COCC(=O)O)CC3)c(=O)cc2-c2ccccc2)cc1] | 2-(((1s,4s)-4-((6-oxo-4-phenyl-3-p-tolylpyridazin-1(6H)-yl)methyl)cyclohexyl)methoxy)acetic acid |
| 21 | 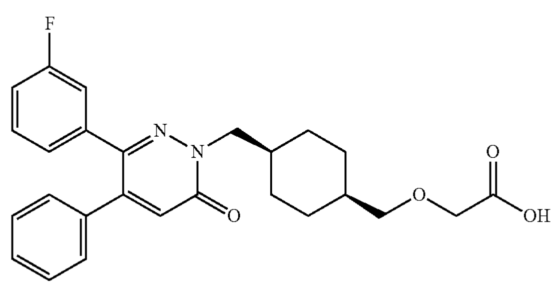 [SMILES: O=C(O)COC[C@H]1CC[C@@H](Cn2nc(-c3cccc(F)c3)c(-c3ccccc3)cc2=O)CC1] | 2-(((1s,4s)-4-((3-(3-fluorophenyl)-6-oxo-4-phenylpyridazin-1(6H)-yl)methyl)cyclohexyl)methoxy)acetic acid |
| 22 | 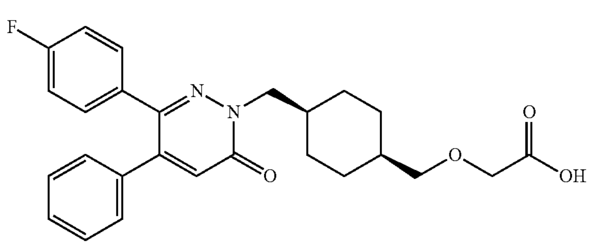 [SMILES: O=C(O)COC[C@H]1CC[C@@H](Cn2nc(-c3ccc(F)cc3)c(-c3ccccc3)cc2=O)CC1] | 2-(((1s,4s)-4-((3-(4-fluorophenyl)-6-oxo-4-phenylpyridazin-1(6H)-yl)methyl)cyclohexyl)methoxy)acetic acid |
| 23 | 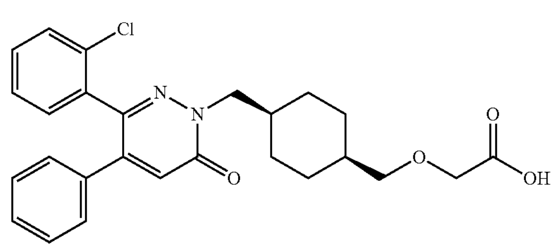 [SMILES: O=C(O)COC[C@H]1CC[C@@H](Cn2nc(-c3ccccc3Cl)c(-c3ccccc3)cc2=O)CC1] | 2-(((1s,4s)-4-((3-(2-chlorophenyl)-6-oxo-4-phenylpyridazin-1(6H)-yl)methyl)cyclohexyl)methoxy)acetic acid |

TABLE A-continued

| Cpd No. | Chemical Structure | Chemical Name |
|---|---|---|
| 24 | 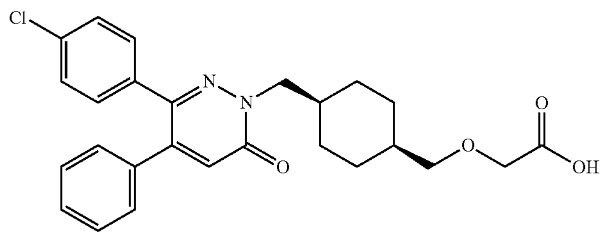 [SMILES: O=C(O)COC[C@H]1CC[C@@H](Cn2nc(-c3ccc(Cl)cc3)c(-c3ccccc3)cc2=O)CC1] | 2-(((1s,4s)-4-((3-(4-chlorophenyl)-6-oxo-4-phenylpyridazin-1(6H)-yl)methyl)cyclohexyl)methoxy)acetic acid |
| 25 | 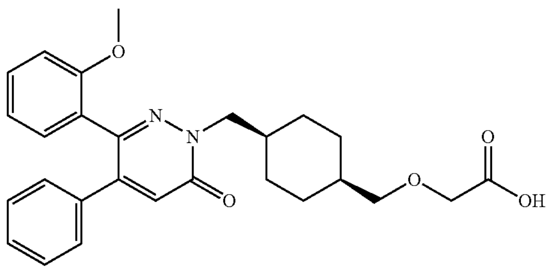 [SMILES: COc1ccccc1-c1nn(C[C@H]2CC[C@@H](COCC(=O)O)CC2)c(=O)cc1-c1ccccc1] | 2-(((1s,4s)-4-((3-(2-methoxyphenyl)-6-oxo-4-phenylpyridazin-1(6H)-yl)methyl)cyclohexyl)methoxy)acetic acid |
| 26 | 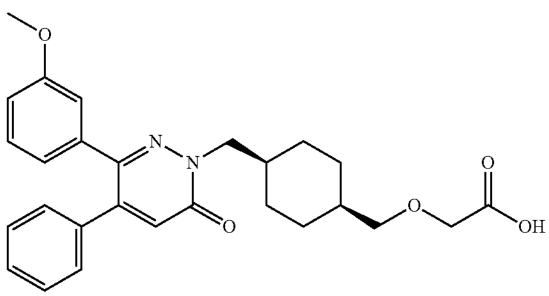 [SMILES: COc1cccc(-c2nn(C[C@H]3CC[C@@H](COCC(=O)O)CC3)c(=O)cc2-c2ccccc2)c1] | 2-(((1s,4s)-4-((3-(3-methoxyphenyl)-6-oxo-4-phenylpyridazin-1(6H)-yl)methyl)cyclohexyl)methoxy)acetic acid |
| 27 | 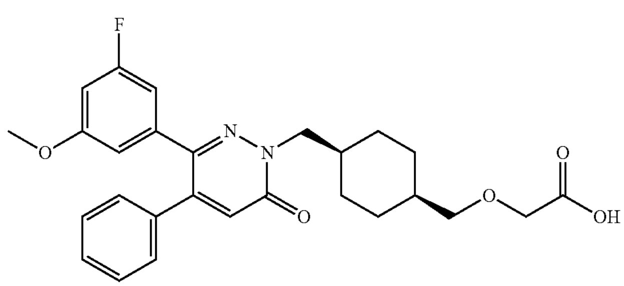 [SMILES: COc1cc(F)cc(-c2nn(C[C@H]3CC[C@@H](COCC(=O)O)CC3)c(=O)cc2-c2ccccc2)c1] | 2-(((1s,4s)-4-((3-(3-fluoro-5-methoxyphenyl)-6-oxo-4-phenylpyridazin-1(6H)-yl)methyl)cyclohexyl)methoxy)acetic acid |
| 28 | 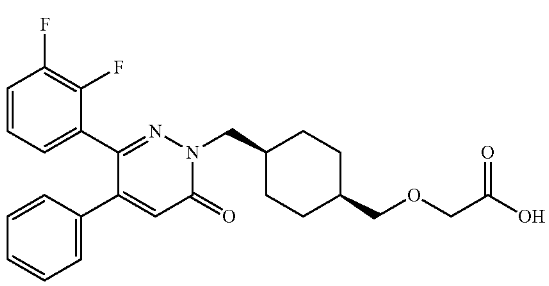 [SMILES: O=C(O)COC[C@H]1CC[C@@H](Cn2nc(-c3cccc(F)c3F)c(-c3ccccc3)cc2=O)CC1] | 2-(((1s,4s)-4-((3-(2,3-difluorophenyl)-6-oxo-4-phenylpyridazin-1(6H)-yl)methyl)cyclohexyl)methoxy)acetic acid |

TABLE A-continued

| Cpd No. | Chemical Structure | Chemical Name |
|---|---|---|
| 29 | 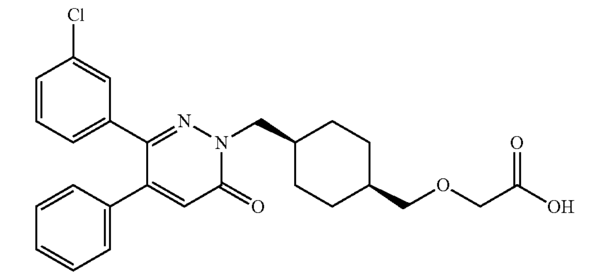 | 2-(((1s,4s)-4-((3-(3-chlorophenyl)-6-oxo-4-phenylpyridazin-1(6H)-yl)methyl)cyclohexyl)methoxy)acetic acid |
| 30 | 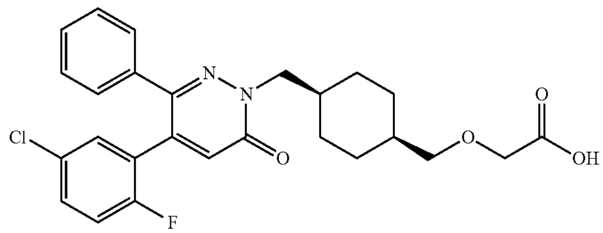 [SMILES: O=C(O)COC[C@H]1CC[C@@H](Cn2nc(-c3ccccc3)c(-c3cc(Cl)ccc3F)cc2=O)CC1] | 2-(((1s,4s)-4-((4-(5-chloro-2-fluorophenyl)-6-oxo-3-phenylpyridazin-1(6H)-yl)methyl)cyclohexyl)methoxy)acetic acid |
| 31 | 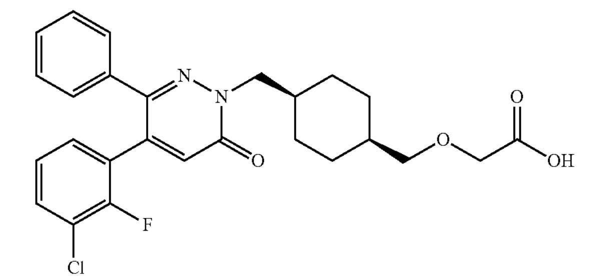 [SMILES: O=C(O)COC[C@H]1CC[C@@H](Cn2nc(-c3ccccc3)c(-c3cccc(Cl)c3F)cc2=O)CC1] | 2-(((1s,4s)-4-((4-(3-chloro-2-fluorophenyl)-6-oxo-3-phenylpyridazin-1(6H)-yl)methyl)cyclohexyl)methoxy)acetic acid |
| 32 | 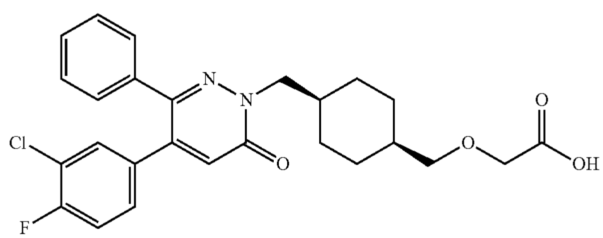 [SMILES: O=C(O)COC[C@H]1CC[C@@H](Cn2nc(-c3ccccc3)c(-c3ccc(F)c(Cl)c3)cc2=O)CC1] | 2-(((1s,4s)-4-((4-(3-chloro-4-fluorophenyl)-6-oxo-3-phenylpyridazin-1(6H)-yl)methyl)cyclohexyl)methoxy)acetic acid |
| 33 | 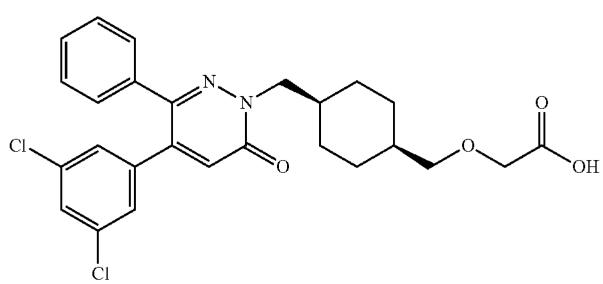 [SMILES: O=C(O)COC[C@H]1CC[C@@H](Cn2nc(-c3ccccc3)c(-c3cc(Cl)cc(Cl)c3)cc2=O)CC1] | 2-(((1s,4s)-4-((4-(3,5-dichlorophenyl)-6-oxo-3-phenylpyridazin-1(6H)-yl)methyl)cyclohexyl)methoxy)acetic acid |
| 34 | 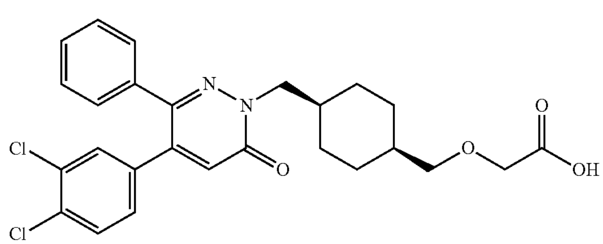 | 2-(((1s,4s)-4-((4-(3,4-dichlorophenyl)-6-oxo-3-phenylpyridazin-1(6H)-yl)methyl)cyclohexyl)methoxy)acetic acid |

TABLE A-continued

| Cpd No. | Chemical Structure | Chemical Name |
|---|---|---|
| 35 | 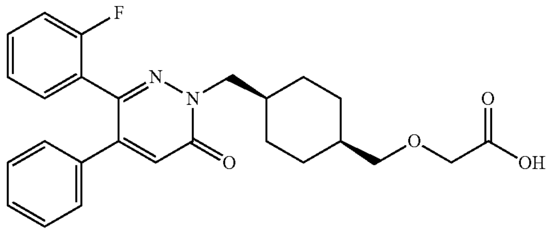 [SMILES: O=C(O)COC[C@H]1CC[C@@H](Cn2nc(-c3ccccc3F)c(-c3ccccc3)cc2=O)CC1] | 2-(((1s,4s)-4-((3-2-fluorophenyl)-6-oxo-4-phenylpyridazin-1(6H)-yl)methyl)cyclohexyl)methoxy)acetic acid |
| 36 | 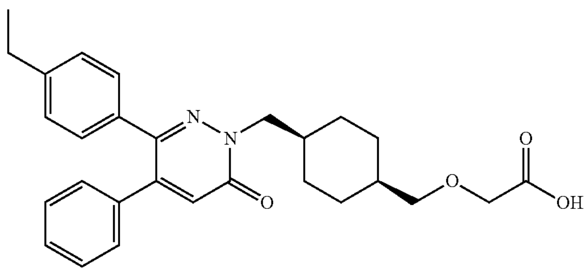 [SMILES: CCc1ccc(-c2nn(C[C@H]3CC[C@@H](COCC(=O)O)CC3)c(=O)cc2-c2ccccc2)cc1] | 2-(((1s,4s)-4-((3-(4-ethylphenyl)-6-oxo-4-phenylpyridazin-1(6H)-yl)methyl)cyclohexyl)methoxy)acetic acid |
| 37 | 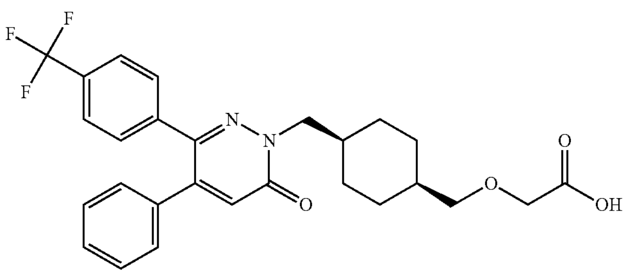 [SMILES: O=C(O)COC[C@H]1CC[C@@H](Cn2nc(-c3ccc(C(F)(F)F)cc3)c(-c3ccccc3)cc2=O)CC1] | 2-(((1s,4s)-4-((6-oxo-4-phenyl-3-(4-(trifluoromethyl)phenyl)pyridazin-l(6H)-yl)methyl)cyclohexyl)methoxy)acetic acid |
| 38 | 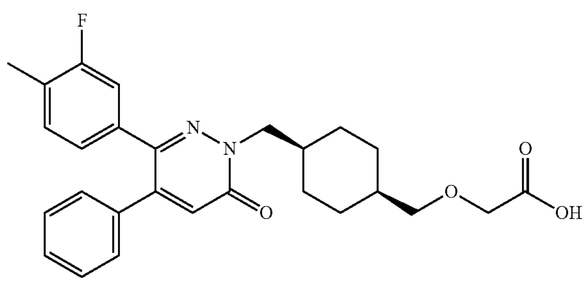 [SMILES: Cc1ccc(-c2nn(C[C@H]3CC[C@@H](COCC(=O)O)CC3)c(=O)cc2-c2ccccc2)cc1F] | 2-(((1s,4s)-4-((3-(3-fluoro-4-methylphenyl)-6-oxo-4-phenylpyridazin-1(6H)-yl)methyl)cyclohexyl)methoxy)acetic acid |
| 39 | 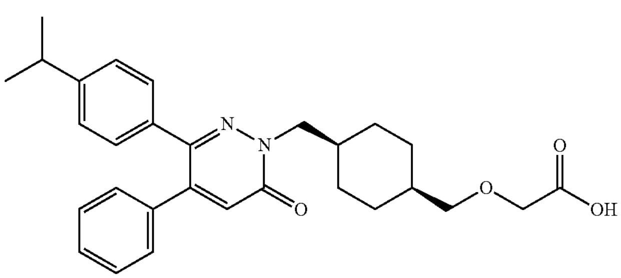 [SMILES: CC(C)c1ccc(-c2nn(C[C@H]3CC[C@@H](COCC(=O)O)CC3)c(=O)cc2-c2ccccc2)cc1] | 2-(((1s,4s)-4-((3-(4-isopropylphenyl)-6-oxo-4-phenylpyridazin-1(6H)-yl)methyl)cyclohexyl)methoxy)acetic acid |
| 40 | 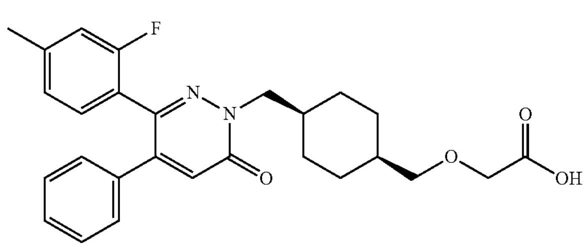 [SMILES: Cc1ccc(-c2nn(C[C@H]3CC[C@@H](COCC(=O)O)CC3)c(=O)cc2-c2ccccc2)c(F)c1] | 2-(((1s,4s)-4-((3-(2-fluoro-4-methylphenyl)-6-oxo-4-phenylpyridazin-1(6H)-yl)methyl)cyclohexyl)methoxy)acetic acid |

| Cpd No. | Chemical Structure | Chemical Name |
|---|---|---|
| 41 | 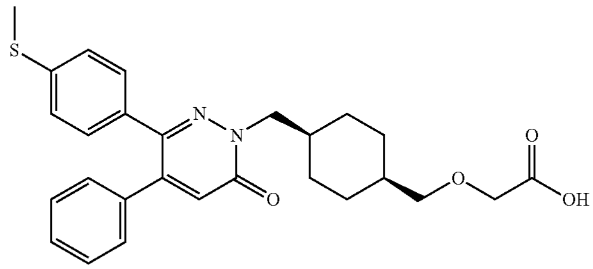 [SMILES: CSc1ccc(-c2nn(C[C@H]3CC[C@@H](COCC(=O)O)CC3)c(=O)cc2-c2ccccc2)cc1] | 2-(((1s,4s)-4-((3-(4-(methylthio)phenyl)-6-oxo-4-phenylpyridazin-1(6H)-yl)methyl)cyclohexyl)methoxy)acetic acid |
| 42 | 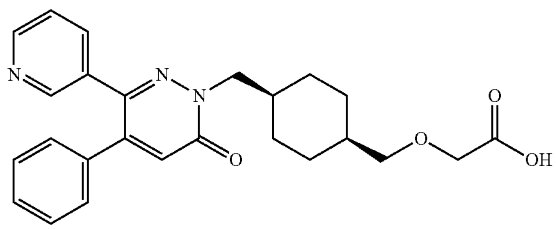 [SMILES: O=C(O)COC[C@H]1CC[C@@H](Cn2nc(-c3cccnc3)c(-c3ccccc3)cc2=O)CC1] | 2-(((1s,4s)-4-((6-oxo-4-phenyl-3-(pyridin-3-yl)pyridazin-1(6H)-yl)methyl)cyclohexyl)methoxy)acetic acid |
| 43 | 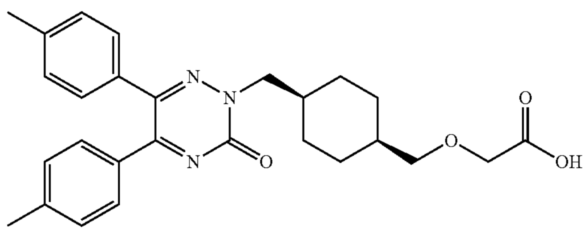 [SMILES: Cc1ccc(-c2nc(=O)n(C[C@H]3CC[C@@H](COCC(=O)O)CC3)nc2-c2ccc(C)cc2)cc1] | 2-(((1s,4s)-4-((3-oxo-5,6-di-p-tolyl-1,2,4-triazin-2(3H)-yl)methyl)cyclohexyl)methoxy)acetic acid |
| 44 | 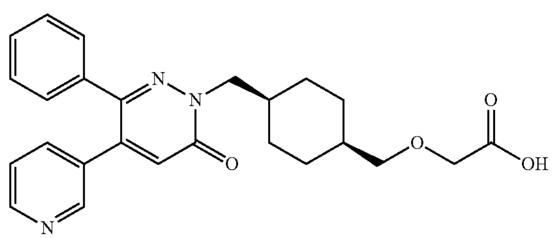 [SMILES: O=C(O)COC[C@H]1CC[C@@H](Cn2nc(-c3ccccc3)c(-c3cccnc3)cc2=O)CC1] | 2-(((1s,4s)-4-((6-oxo-3-phenyl-4-(pyridin-3-yl)pyridazin-1(6H)-yl)methyl)cyclohexyl)methoxy)acetic acid |
| 45 | 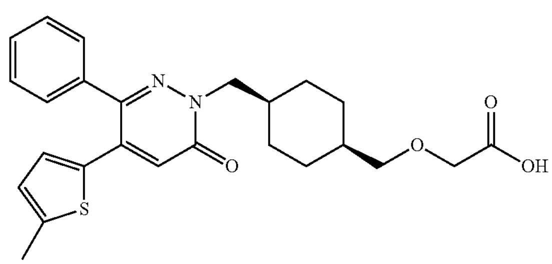 [SMILES: Cc1ccc(-c2cc(=O)n(C[C@H]3CC[C@@H](COCC(=O)O)CC3)nc2-c2ccccc2)s1] | 2-(((1s,4s)-4-((4-(5-methylthiophen-2-yl)-6-oxo-3-phenylpyridazin-1(6H)-yl)methyl)cyclohexyl)methoxy)acetic acid |
| 46 | 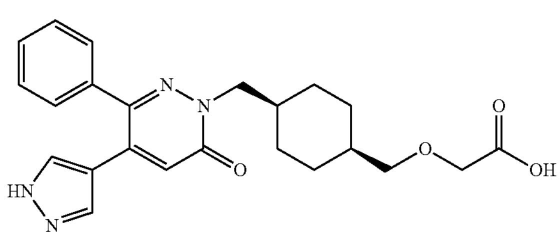 [SMILES: O=C(O)COC[C@H]1CC[C@@H](Cn2nc(-c3ccccc3)c(-c3cn[nH]c3)cc2=O)CC1] | 2-(((1s,4s)-4-((6-oxo-3-phenyl-4-(1H-pyrazol-4-yl)pyridazin-1(6H)-yl)methyl)cyclohexyl)methoxy)acetic acid |

TABLE A-continued

| Cpd No. | Chemical Structure | Chemical Name |
|---|---|---|
| 47 | 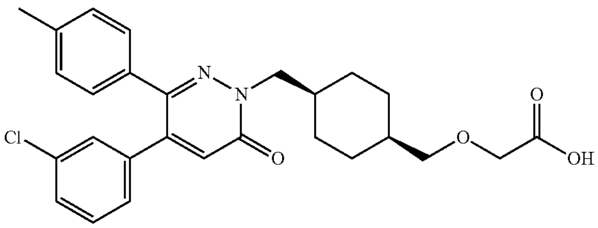 [SMILES: Cc1ccc(-c2nn(C[C@H]3CC[C@@H](COCC(=O)O)CC3)c(=O)cc2-c2cccc(Cl)c2)cc1] | 2-(((1s,4s)-4-((4-(3-chlorophenyl)-6-oxo-3-p-tolylpyridazin-1(6H)-yl)methyl)cyclohexyl)methoxy)acetic acid |
| 48 | 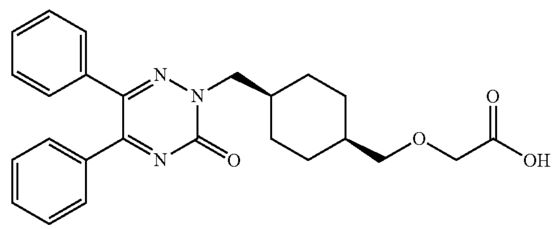 [SMILES: O=C(O)COC[C@H]1CC[C@@H](Cn2nc(-c3ccccc3)c(-c3ccccc3)nc2=O)CC1] | 2-(((1s,4s)-4-((3-oxo-5,6-diphenyl-1,2,4-triazin-2(3H)-yl)methyl)cyclohexyl)methoxy)acetic acid |
| 49 | 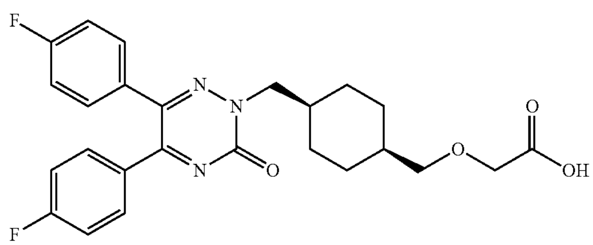 [SMILES: O=C(O)COC[C@H]1CC[C@@H](Cn2nc(-c3ccc(F)cc3)c(-c3ccc(F)cc3)nc2=O)CC1] | 2-(((1s,4s)-4-((5,6-bis(4-fluorophenyl)-3-oxo-1,2,4-triazin-2(3H)-yl)methyl)cyclohexyl)methoxy)acetic acid |
| 50 | 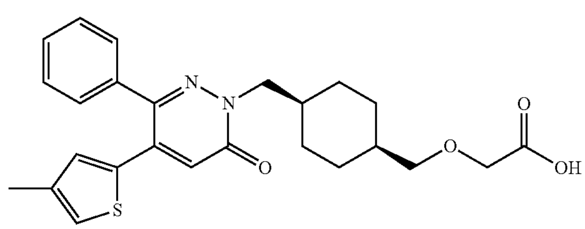 [SMILES: Cc1csc(-c2cc(=O)n(C[C@H]3CC[C@@H](COCC(=O)O)CC3)nc2-c2ccccc2)c1] | 2-(((1s,4s)-4-((4-(4-methylthiophen-2-yl)-6-oxo-3-phenylpyridazin-1(6H)-yl)methyl)cyclohexyl)methoxy)acetic acid |
| 51 | 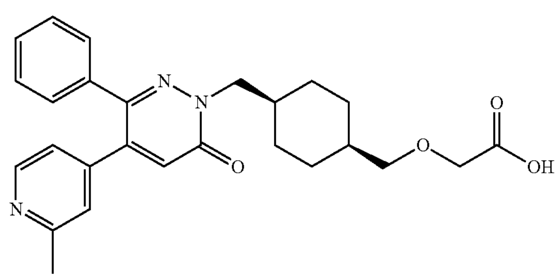 [SMILES: Cc1cc(-c2cc(=O)n(C[C@H]3CC[C@@H](COCC(=O)O)CC3)nc2-c2ccccc2)ccn1] | 2-(((1s,4s)-4-((4-(2-methylpyridin-4-yl)-6-oxo-3-phenylpyridazin-1(6H)-yl)methyl)cyclohexyl)methoxy)acetic acid |
| 52 | 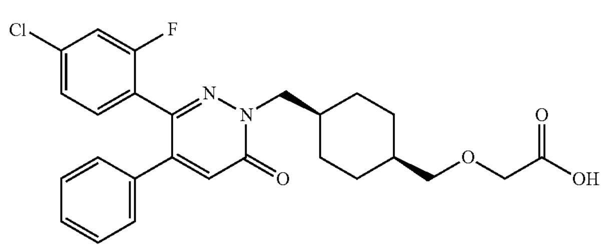 [SMILES: O=C(O)COC[C@H]1CC[C@@H](Cn2nc(-c3ccc(Cl)cc3F)c(-c3ccccc3)cc2=O)CC1] | 2-(((1s,4s)-4-((3-(4-chloro-2-fluorophenyl)-6-oxo-4-phenylpyridazin-1(6H)-yl)methyl)cyclohexyl)methoxy)acetic acid |

| Cpd No. | Chemical Structure | Chemical Name |
|---|---|---|
| 53 | 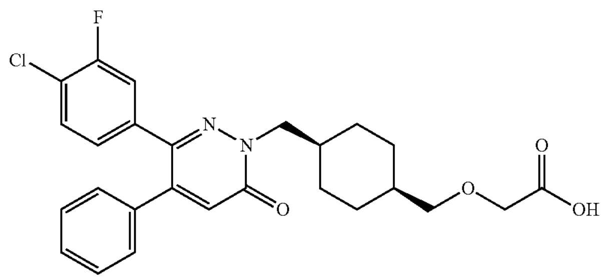 [SMILES: O=C(O)COC[C@H]1CC[C@@H](Cn2nc(-c3ccc(Cl)c(F)c3)c(-c3ccccc3)cc2=O)CC1] | 2-(((1s,4s)-4-((3-(4-chloro-3-fluorophenyl)-6-oxo-4-phenylpyridazin-1(6H)-yl)methyl)cyclohexyl)methoxy)acetic acid |
| 54 | 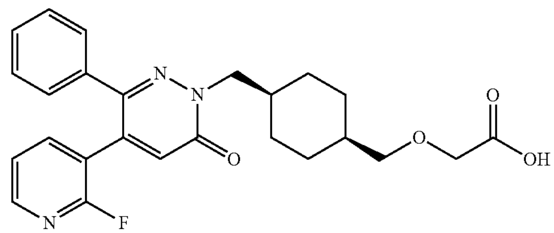 [SMILES: O=C(O)COC[C@H]1CC[C@@H](Cn2nc(-c3ccccc3)c(-c3cccnc3F)cc2=O)CC1] | 2-(((1s,4s)-4-((4-(2-fluoropyridin-3-yl)-6-oxo-3-phenylpyridazin-1(6H)-yl)methyl)cyclohexyl)methoxy)acetic acid |
| 55 | 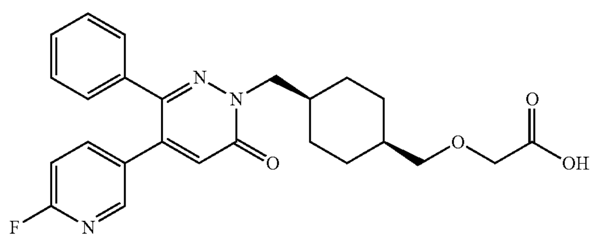 [SMILES: O=C(O)COC[C@H]1CC[C@@H](Cn2nc(-c3ccccc3)c(-c3ccc(F)nc3)cc2=O)CC1] | 2-(((1s,4s)-4-((4-(6-fluoropyridin-3-yl)-6-oxo-3-phenylpyridazin-1(6H)-yl)methyl)cyclohexyl)methoxy)acetic acid |
| 56 | 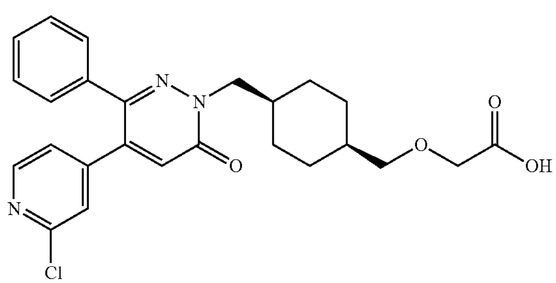 | 2-(((1s,4s)-4-((4-(2-chloropyridin-4-yl)-6-oxo-3-phenylpyridazin-1(6H)-yl)methyl)cyclohexyl)methoxy)acetic acid |
| 57 | 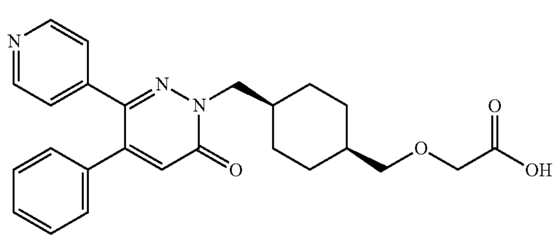 [SMILES: O=C(O)COC[C@H]1CC[C@@H](Cn2nc(-c3ccncc3)c(-c3ccccc3)cc2=O)CC1] | 2-(((1s,4s)-4-((6-oxo-4-phenyl-3-(pyridin-4-yl)pyridazin-1(6H)-yl)methyl)cyclohexyl)methoxy)acetic acid |
| 58 | 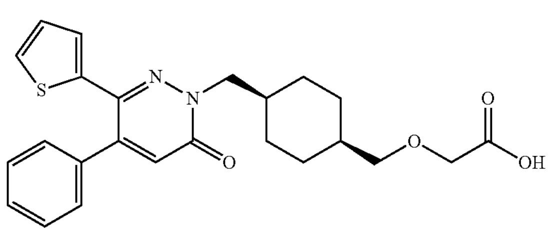 [SMILES: O=C(O)COC[C@H]1CC[C@@H](Cn2nc(-c3cccs3)c(-c3ccccc3)cc2=O)CC1] | 2-(((1s,4s)-4-((6-oxo-4-phenyl-3-(thiophen-2-yl)pyridazin-1(6H)-yl)methyl)cyclohexyl)methoxy)acetic acid |

TABLE A-continued

| Cpd No. | Chemical Structure | Chemical Name |
|---|---|---|
| 59 | 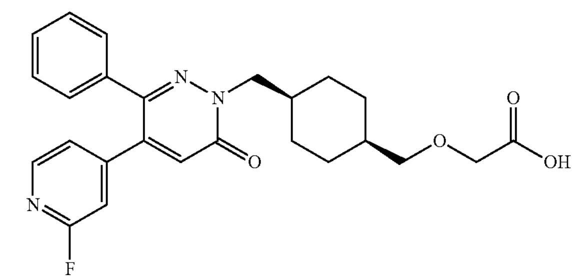 [SMILES: O=C(O)COC[C@H]1CC[C@@H](Cn2nc(-c3ccccc3)c(-c3ccnc(F)c3)cc2=O)CC1] | 2-(((1s,4s)-4-((4-(2-fluoropyridin-4-yl)-6-oxo-3-phenylpyridazin-1(6H)-yl)methyl)cyclohexyl)methoxy)acetic acid |
| 60 | 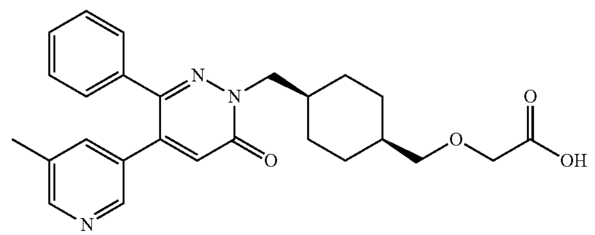 [SMILES: Cc1cncc(-c2cc(=O)n(C[C@H]3CC[C@@H](COCC(=O)O)CC3)nc2-c2ccccc2)c1] | 2-(((1s,4s)-4-((4-(5-methylpyridin-3-yl)-6-oxo-3-phenylpyridazin-1(6H)-yl)methyl)cyclohexyl)methoxy)acetic acid |
| 61 | 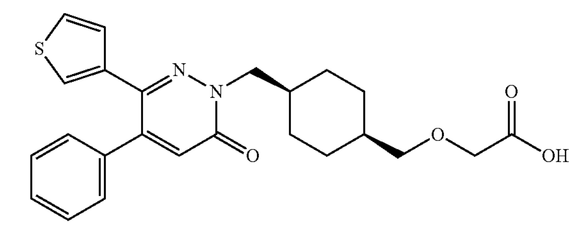 [SMILES: O=C(O)COC[C@H]1CC[C@@H](Cn2nc(-c3ccsc3)c(-c3ccccc3)cc2=O)CC1] | 2-(((1s,4s)-4-((6-oxo-4-phenyl-3-(thiophen-3-yl)pyridazin-1(6H)-yl)methyl)cyclohexyl)methoxy)acetic acid |
| 62 | 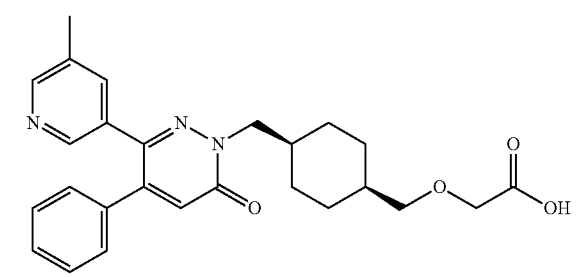 [SMILES: Cc1cncc(-c2nn(C[C@H]3CC[C@@H](COCC(=O)O)CC3)c(=O)cc2-c2ccccc2)c1] | 2-(((1s,4s)-4-((3-(5-methylpyridin-3-yl)-6-oxo-4-phenylpyridazin-1(6H)-yl)methyl)cyclohexyl)methoxy)acetic acid |
| 63 | 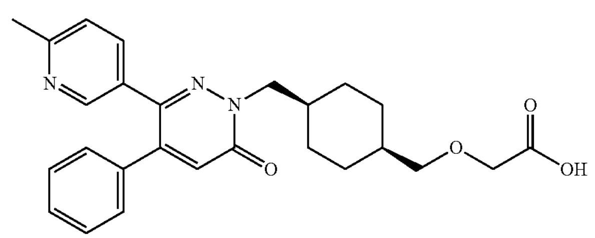 [SMILES: Cc1ccc(-c2nn(C[C@H]3CC[C@@H](COCC(=O)O)CC3)c(=O)cc2-c2ccccc2)cn1] | 2-(((1s,4s)-4-((3-(6-methylpyridin-3-yl)-6-oxo-4-phenylpyridazin-1(6H)-yl)methyl)cyclohexyl)methoxy)acetic acid |
| 64 | 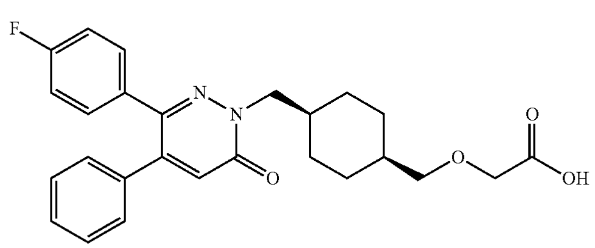 [SMILES: O=C(O)COC[C@H]1CC[C@@H](Cn2nc(-c3ccc(F)cc3)c(-c3ccccc3)cc2=O)CC1] | 2-(((1s,4s)-4-((6-(4-fluorophenyl)-3-oxo-5-phenyl-1,2,4-triazin-2(3H)-yl)methyl)cyclohexyl)methoxy)acetic acid |

TABLE A-continued

| Cpd No. | Chemical Structure | Chemical Name |
|---|---|---|
| 65 | 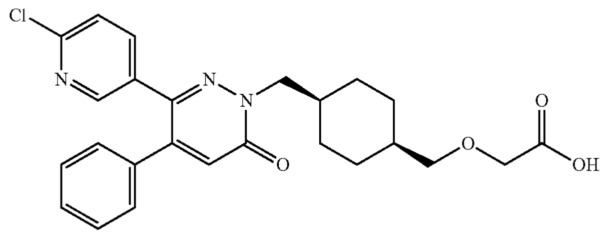 [SMILES: O=C(O)COC[C@H]1CC[C@@H](Cn2nc(-c3ccc(Cl)nc3)c(-c3ccccc3)cc2=O)CC1] | 2-(((1s,4s)-4-(3-(6-chloropyridin-3-yl)-6-oxo-4-phenylpyridazin-1(6H)-yl)methyl)cyclohexyl)methoxy)acetic acid |
| 66 | 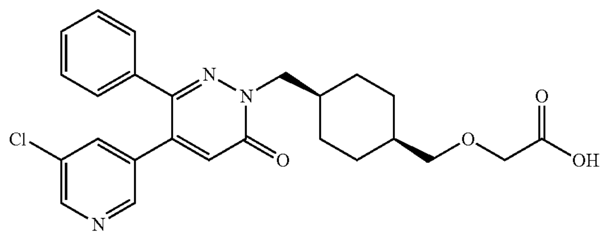 [SMILES: O=C(O)COC[C@H]1CC[C@@H](Cn2nc(-c3ccccc3)c(-c3cncc(Cl)c3)cc2=O)CC1] | 2-(((1s,4s)-4-((4-(5-chloropyridin-3-yl)-6-oxo-3-phenylpyridazin-1(6H)-yl)methyl)cyclohexyl)methoxy)acetic acid |
| 67 | 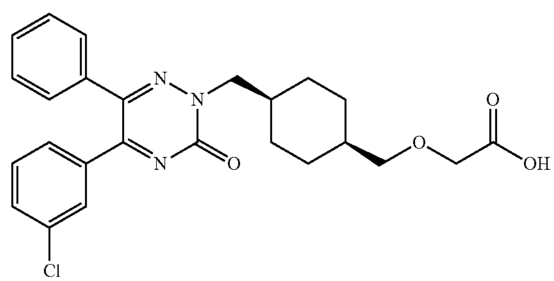 | 2-(((1s,4s)-4-((5-(3-chlorophenyl)-3-oxo-6-phenyl-1,2,4-triazin-2(3H)-yl)methyl)cyclohexyl)methoxy)acetic acid |
| 68 | 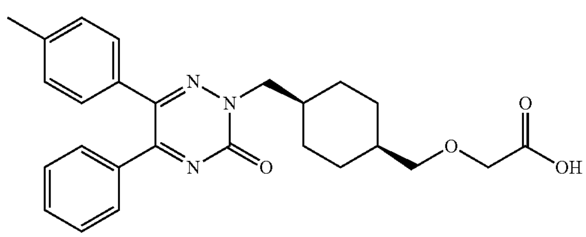 [SMILES: Cc1ccc(-c2nn(C[C@H]3CC[C@@H](COCC(=O)O)CC3)c(=O)nc2-c2ccccc2)cc1] | 2-(((1s,4s)-4-((3-oxo-5-phenyl-6-p-tolyl-1,2,4-triazin-2(3H)-yl)methyl)cyclohexyl)methoxy)acetic acid |
| 69 | 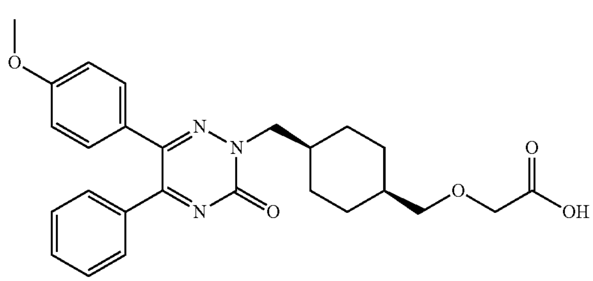 [SMILES: COc1ccc(-c2nn(C[C@H]3CC[C@@H](COCC(=O)O)CC3)c(=O)nc2-c2ccccc2)cc1] | 2-(((1s,4s)-4-((6-(4-methoxyphenyl)-3-oxo-5-phenyl-1,2,4-triazin-2(3H)-yl)methyl)cyclohexyl)methoxy)acetic acid |
| 70 | 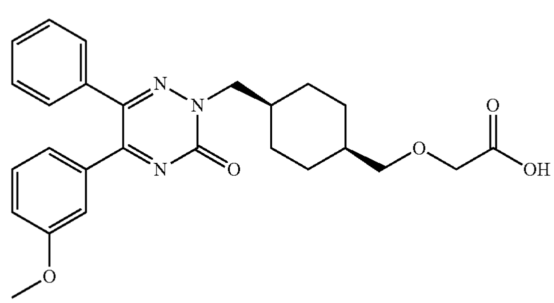 [SMILES: COc1cccc(-c2nc(=O)n(C[C@H]3CC[C@@H](COCC(=O)O)CC3)nc2-c2ccccc2)c1] | 2-(((1s,4s)-4-((5-(3-methoxyphenyl)-3-oxo-6-phenyl-1,2,4-triazin-2(3H)-yl)methyl)cyclohexyl)methoxy)acetic acid |

TABLE A-continued

| Cpd No. | Chemical Structure | Chemical Name |
|---|---|---|
| 71 | 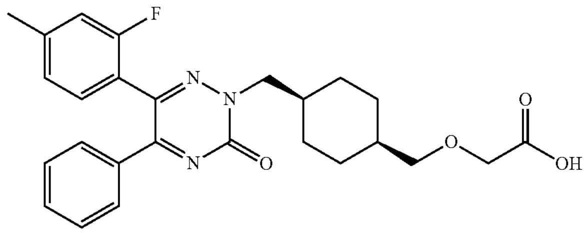 [SMILES: Cc1ccc(-c2nn(C[C@H]3CC[C@@H](COCC(=O)O)CC3)c(=O)nc2-c2ccccc2)c(F)c1] | 2-(((1s,4s)-4-((6-(2-fluoro-4-methylphenyl)-3-oxo-5-phenyl-1,2,4-triazin-2(3H)-yl)methyl)cyclohexyl)methoxy)acetic acid |
| 72 | 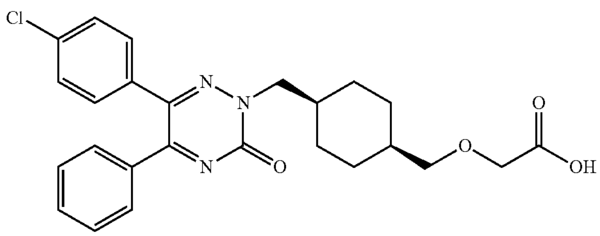 [SMILES: O=C(O)COC[C@H]1CC[C@@H](Cn2nc(-c3ccc(Cl)cc3)c(-c3ccccc3)nc2=O)CC1] | 2-(((1s,4s)-4-((6-(4-chlorophenyl)-3-oxo-5-phenyl-1,2,4-triazin-2(3H)-yl)methyl)cyclohexyl)methoxy)acetic acid |
| 73 | 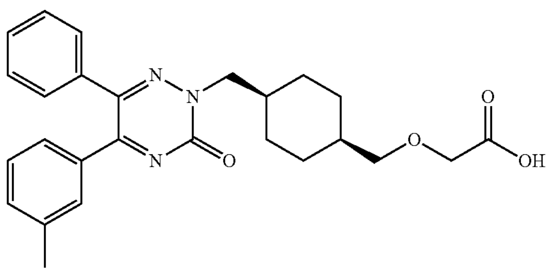 [SMILES: Cc1cccc(-c2nc(=O)n(C[C@H]3CC[C@@H](COCC(=O)O)CC3)nc2-c2ccccc2)c1] | 2-(((1s,4s)-4-((3-oxo-6-phenyl-5-m-tolyl-1,2,4-triazin-2(3H)-yl)methyl)cyclohexyl)methoxy)acetic acid |
| 74 | 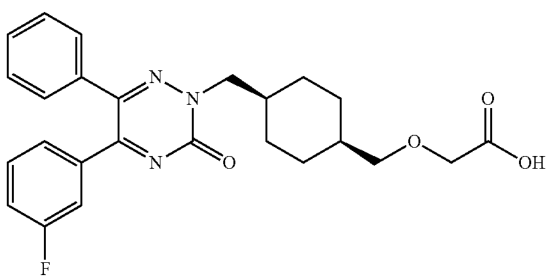 [SMILES: O=C(O)COC[C@H]1CC[C@@H](Cn2nc(-c3ccccc3)c(-c3cccc(F)c3)nc2=O)CC1] | 2-(((1s,4s)-4-((5-(3-fluorophenyl)-3-oxo-6-phenyl-1,2,4-triazin-2(3H)-yl)methyl)cyclohexyl)methoxy)acetic acid |
| 75 | 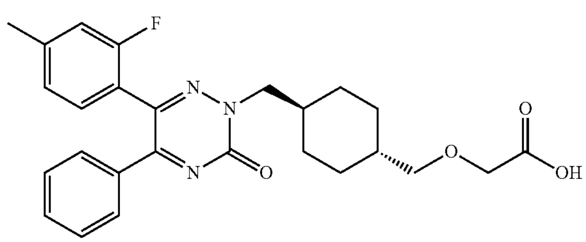 [SMILES: Cc1ccc(-c2nn(C[C@H]3CC[C@H](COCC(=O)O)CC3)c(=O)nc2-c2ccccc2)c(F)c1] | 2-(((1r,4r)-4-((6-(2-fluoro-4-methylphenyl)-3-oxo-5-phenyl-1,2,4-triazin-2(3H)-yl)methyl)cyclohexyl)methoxy)acetic acid |
| 76 | 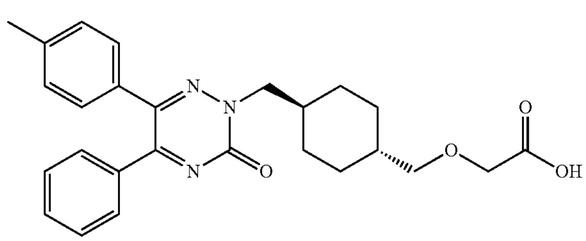 [SMILES: Cc1ccc(-c2nn(C[C@H]3CC[C@H](COCC(=O)O)CC3)c(=O)nc2-c2ccccc2)cc1] | 2-(((1r,4r)-4-((3-oxo-5-phenyl-6-p-tolyl-1,2,4-triazin-2(3H)-yl)methyl)cyclohexyl)methoxy)acetic acid |

| Cpd No. | Chemical Structure | Chemical Name |
|---|---|---|
| 77 | 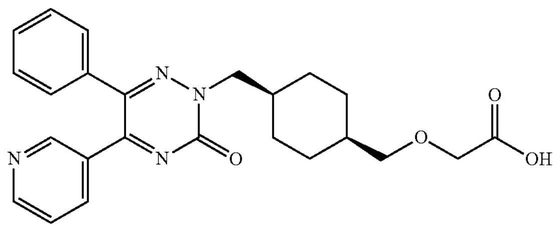 [SMILES: O=C(O)COC[C@H]1CC[C@@H](Cn2nc(-c3ccccc3)c(-c3cccnc3)nc2=O)CC1] | 2-(((1s,4s)-4-((3-oxo-6-phenyl-5-(pyridin-3-yl)-1,2,4-triazin-2(3H)-yl)methyl)cyclohexyl)methoxy)acetic acid |
| 78 | 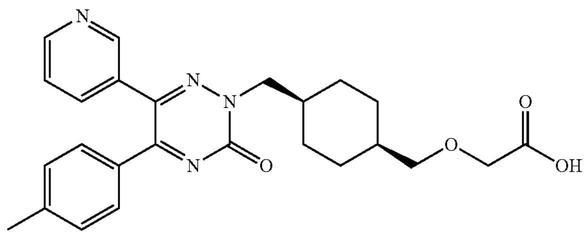 [SMILES: Cc1ccc(-c2nc(=O)n(C[C@H]3CC[C@@H](COCC(=O)O)CC3)nc2-c2cccnc2)cc1] | 2-(((1s,4s)-4-((3-oxo-6-(pyridin-3-yl)-5-p-tolyl-1,2,4-triazin-2(3H)-yl)methyl)cyclohexyl)methoxy)acetic acid |
| 79 | 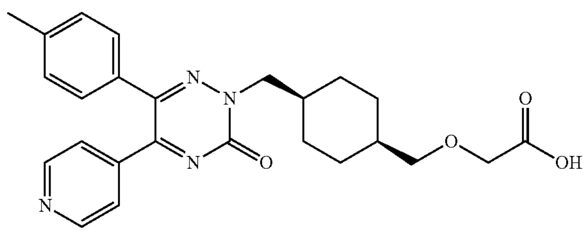 [SMILES: Cc1ccc(-c2nn(C[C@H]3CC[C@@H](COCC(=O)O)CC3)c(=O)nc2-c2ccncc2)cc1] | 2-(((1s,4s)-4-((3-oxo-5-(pyridin-4-yl)-6-p-tolyl-1,2,4-triazin-2(3H)-yl)methyl)cyclohexyl)methoxy)acetic acid |
| 80 | 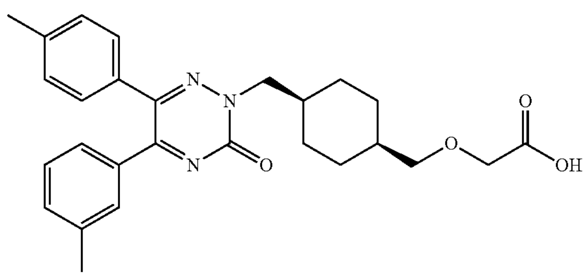 [SMILES: Cc1ccc(-c2nn(C[C@H]3CC[C@@H](COCC(=O)O)CC3)c(=O)nc2-c2cccc(C)c2)cc1] | 2-(((1s,4s)-4-((3-oxo-5-m-tolyl-6-p-tolyl-1,2,4-triazin-2(3H)-yl)methyl)cyclohexyl)methoxy)acetic acid |
| 81 | 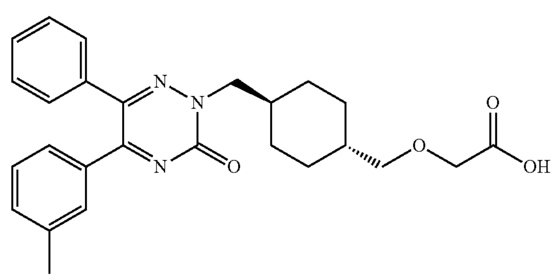 [SMILES: Cc1cccc(-c2nc(=O)n(C[C@H]3CC[C@H](COCC(=O)O)CC3)nc2-c2ccccc2)c1] | 2-(((1r,4r)-4-((3-oxo-6-phenyl-5-m-tolyl-1,2,4-triazin-2(3H)-yl)methyl)cyclohexyl)methoxy)acetic acid |
| 82 | 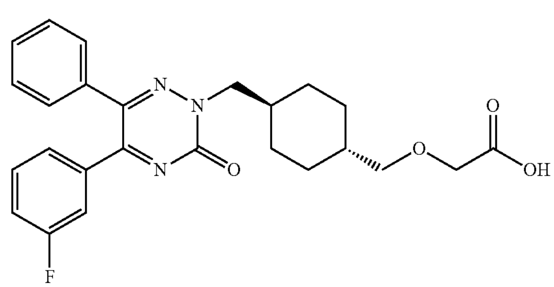 [SMILES: O=C(O)COC[C@H]1CC[C@H](Cn2nc(-c3ccccc3)c(-c3cccc(F)c3)nc2=O)CC1] | 2-(((1r,4r)-4-((5-(3-fluorophenyl)-3-oxo-6-phenyl-1,2,4-triazin-2(3H)-yl)methyl)cyclohexyl)methoxy)acetic acid |

TABLE A-continued

| Cpd No. | Chemical Structure | Chemical Name |
|---|---|---|
| 83 | 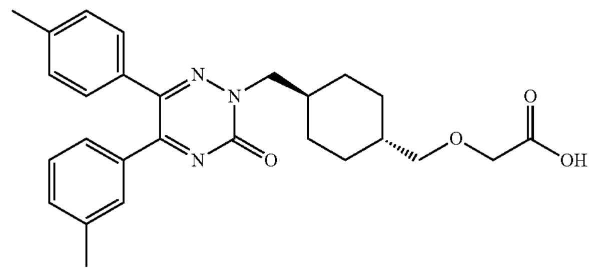 [SMILES: Cc1ccc(-c2nn(C[C@H]3CC[C@H](COCC(=O)O)CC3)c(=O)nc2-c2cccc(C)c2)cc1] | 2-(((1r,4r)-4-((3-oxo-5-m-tolyl-6-p-tolyl-1,2,4-triazin-2(3H)-yl)methyl)cyclohexyl)methoxy)acetic acid |
| 84 | 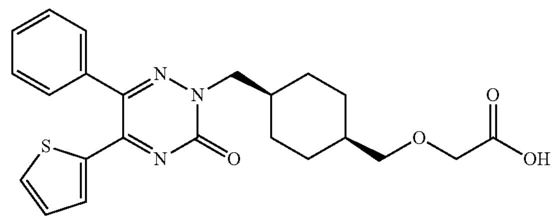 [SMILES: O=C(O)COC[C@H]1CC[C@@H](Cn2nc(-c3ccccc3)c(-c3cccs3)nc2=O)CC1] | 2-(((1s,4s)-4-((3-oxo-6-phenyl-5-(thiophen-2-yl)-1,2,4-triazin-2(3H)-yl)methyl)cyclohexyl)methoxy)acetic acid |
| 85 | 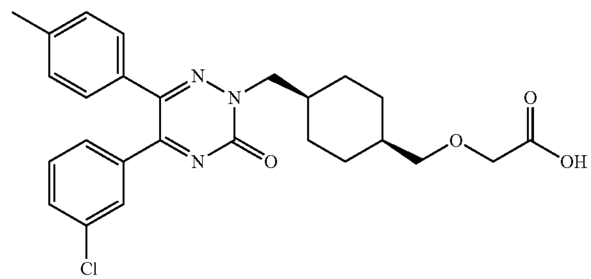 [SMILES: Cc1ccc(-c2nn(C[C@H]3CC[C@@H](COCC(=O)O)CC3)c(=O)nc2-c2cccc(Cl)c2)cc1] | 2-(((1s,4s)-4-((5-(3-chlorophenyl)-3-oxo-6-p-tolyl-1,2,4-triazin-2(3H)-yl)methyl)cyclohexyl)methoxy)acetic acid |
| 86 | 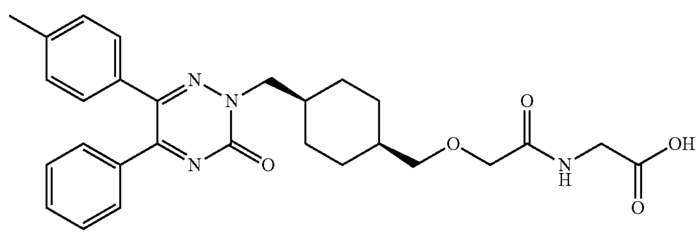 [SMILES: Cc1ccc(-c2nn(C[C@H]3CC[C@@H](COCC(=O)NCC(=O)O)CC3)c(=O)nc2-c2ccccc2)cc1] | 2-(2-(((1s,4s)-4-((3-oxo-5-phenyl-6-p-tolyl-1,2,4-triazin-2(3H)-yl)methyl)cyclohexyl)methoxy)acetamido) acetic acid |
| 87 | 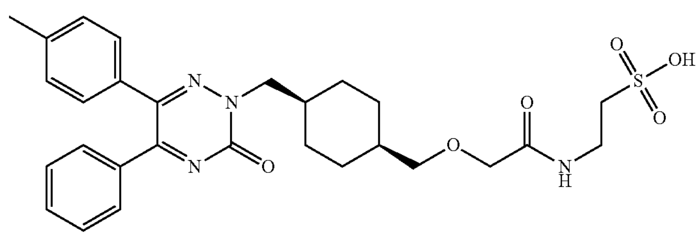 [SMILES: Cc1ccc(-c2nn(C[C@H]3CC[C@@H](COCC(=O)NCCS(=O)(=O)O)CC3)c(=O)nc2-c2ccccc2)cc1] | 2-(2-(((1s,4s)-4-((3-oxo-5-phenyl-6-p-tolyl-1,2,4-triazin-2(3H)-yl)methyl)cyclohexyl)methoxy)acetamido) ethanesulfonic acid |

Additionally, individual compounds and chemical genera of the present invention, for example those compounds found in TABLE A including diastereoisomers and enantiomers thereof, encompass all pharmaceutically acceptable salts, solvates and particularly hydrates, thereof.

The compounds of the Formula Ia of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]; incorporated herein by reference in its entirety).

It is understood that the present invention embraces each diastereoisomer, each enantiomer and mixtures thereof of each compound and generic formulae disclosed herein just as if they were each individually disclosed with the specific stereochemical designation for each chiral carbon. Separation of the individual isomers (such as, by chiral HPLC, recrystallization of diastereoisomeric mixtures and the like) or selective synthesis (such as, by enantiomeric selective syntheses and the like) of the individual isomers is accomplished by application of various methods which are well known to practitioners in the art.

Indications and Methods of Prophylaxis and/or Treatment

In addition to the foregoing beneficial uses for the modulators of PGI2 receptor activity disclosed herein, the compounds disclosed herein are useful in the treatment of several additional diseases and disorders, and in the amelioration of symptoms thereof. Without limitation, these include the following:

1. Pulmonary Arterial Hypertension (PAH)

Pulmonary arterial hypertension (PAH) has a multifactorial pathobiology. Vasoconstriction, remodeling of the pulmonary vessel wall, and thrombosis contribute to increased pulmonary vascular resistance in PAH (Humbert et al., J. Am. Coll. Cardiol., 2004, 43:13S-24S.)

The compounds of the present invention disclosed herein are useful in the treatment of pulmonary arterial hypertension (PAH) and symptoms thereof. PAH shall be understood to encompass the following forms of pulmonary arterial hypertension described in the 2003 World Health Organization (WHO) clinical classification of pulmonary arterial hypertension: idiopathic PAH (IPAH); familial PAH (FPAH); PAH associated with other conditions (APAH), such as PAH associated with collagen vascular disease, PAH associated with congenital systemic-to-pulmonary shunts, PAH associated with portal hypertension, PAH associated with HIV infection, PAH associated with drugs or toxins, or PAH associated with Other; and PAH associated with significant venous or capillary involvement.

Idiopathic PAH refers to PAH of undetermined cause.

Familial PAH refers to PAH for which hereditary transmission is suspected or documented.

PAH associated with collagen vascular disease shall be understood to encompass PAH associated with scleroderma, PAH associated with CREST (calcinosis cutis, Raynaud's phenomenon, esophageal dysfunction, sclerodactyly), and telangiectasias) syndrome, PAH associated with systemic lupus erythematosus (SLE), PAH associated with rheumatoid arthritis, PAH associated with Takayasu's arteritis, PAH associated with polymyositis, and PAH associated with dermatomyositis.

PAH associated with congenital systemic-to-pulmonary shunts shall be understood to encompass PAH associated with atrial septal defect (ASD), PAH associated with ventricular septal defect (VSD) and PAH associated with patent ductus arteriosus.

PAH associated with drugs or toxins shall be understood to encompass PAH associated with ingestion of aminorex, PAH associated with ingestion of a fenfluramine compound (e.g., PAH associated with ingestion of fenfluramine or PAH associated with ingestion of dexfenfluramine), PAH associated with ingestion of certain toxic oils (e.g., PAH associated with ingestion of rapeseed oil), PAH associated with ingestion of pyrrolizidine alkaloids (e.g., PAH associated with ingestion of bush tea) and PAH associated with ingestion of monocrotaline.

PAH associated with Other shall be understood to encompass PAH associated with a thyroid disorder, PAH associated with glycogen storage disease, PAH associated with Gaucher disease, PAH associated with hereditary hemorrhagic telangiectasia, PAH associated with a hemoglobinopathy, PAH associated with a myeloproliferative disorder, and PAH associated with splenectomy.

PAH associated with significant venous or capillary involvement shall be understood to encompass PAH associated with pulmonary veno-occlusive disease (PVOD) and PAH associated with pulmonary capillary hemangiomatosis (PCH).

(See, e.g., Simonneau et al., J. Am. Coll. Cardiol., 2004, 43:5S-12S; McGoon et al., Chest, 2004, 126:14 S-34S; Rabinovitch, Annu. Rev. Pathol. Mech. Dis., 2007, 2:369-399; McLaughlin et al., Circulation, 2006, 114:1417-1431; Strauss et al., Clin. Chest. Med., 2007, 28:127-142; Taichman et al., Clin. Chest. Med., 2007, 28:1-22.)

Evidence for the association of PAH with scleroderma and the beneficial effect of an agonist of the PGI2 receptor on PAH is given by Badesch et al. (Badesch et al., Ann. Intern. Med., 2000, 132:425-434). Evidence for the association of PAH with the collagen vascular diseases mixed connective tissue disease (MCTD), systemic lupus erythematosus (SLE), Sjögren's syndrome and CREST syndrome and the beneficial effect of an agonist of the PGI2 receptor on PAH is given by Humbert et al. (Eur. Respir. J., 1999, 13:1351-1356). Evidence for the association of PAH with CREST syndrome and the beneficial effect of an agonist of the PGI2 receptor on PAH is given by Miwa et al. (Int. Heart J., 2007, 48:417-422). Evidence for the association of PAH with SLE and the beneficial effect of an agonist of the PGI2 receptor on PAH is given by Robbins et al. (Chest, 2000, 117:14-18). Evidence for the association of PAH with HIV infection and the beneficial of an agonist of the PGI2 receptor on PAH is given by Aguilar et al. (Am. J. Respir. Crit. Care Med., 2000, 162:1846-1850). Evidence for the association of PAH with congenital heart defects (including ASD, VSD and patent ductus arteriosus) and the beneficial effect of an agonist of the PGI2 receptor on PAH is given by Rosenzweig et al. (Circulation, 1999, 99:1858-1865). Evidence for the association of PAH with fenfluramine and with dexfenfluramine, anorexigens, is given by Archer et al. (Am. J. Respir. Crit. Care Med., 1998, 158:1061-1067). Evidence for the association of PAH with hereditary hemorrhagic telangiectasia is given by McGoon et al. (Chest, 2004, 126:14-34). Evidence for the association of PAH with splenectomy is given by Hoeper et al. (Ann. Intern. Med., 1999, 130:506-509). Evidence for the association of PAH with portal hypertension and the beneficial effect of an agonist of the PGI2 receptor on PAH is given by Hoeper et al. (Eur. Respir. J., 2005, 25:502-508).

Symptoms of PAH include dyspnea, angina, syncope and edema (McLaughlin et al., Circulation, 2006, 114:1417-1431). The compounds of the present invention disclosed herein are useful in the treatment of symptoms of PAH.

Tawara et al. have demonstrated that long-term inhibition of Rho-kinase, an effector of the small GTPase Rho, ameliorates monocrotaline-induced PAH in rats and hypoxia-induced. PAH in mice. The same group also reported that prostacyclin and its oral analog, beraprost sodium (BPS), may lack direct inhibitory effect on Rho-kinase in vitro, suggesting that combination therapy with a Rho-kinase inhibitor and BPS is effective for the treatment of PAH. Thus, male Sprague-Dawley rats were given a s.c. injection of monocrotaline (60 mg/kg) and maintained with or without the treatment with a Rho-kinase inhibitor, fasudil (30 mg/kg/day), BPS (200 μg/kg/day), or a combination of both drugs for three weeks. The combination therapy, when compared with each monotherapy, showed significantly more improvement in PAH, right ventricular hypertrophy, and pulmonary medial thickness without any adverse effects. (See, Tawara et al., Journal of Cardiovascular Pharmacology (2007), 50(2), 195-200.)

The PGI2 receptor agonists disclosed herein, alone or in combination with a Rho-kinase inhibitor, are useful in the treatment of pulmonary arterial hypertension (PAH) and symptoms thereof.

The enzyme tryptophan hydroxylase (TPH), has two known isoforms: TPH1, which is expressed in the periphery, and TPH2, which is expressed primarily in the brain. Mice genetically deficient for the TPH1 gene ("knockout mice") have been reported. In one case, the mice reportedly expressed normal amounts of serotonin in classical serotonergic brain regions, but largely lacked serotonin in the periphery. Walther, D. J., et al., Science 299:76 (2003). In another, the knockout mice exhibited abnormal cardiac activity, which was attributed to a lack of peripheral serotonin. Cote, F., et al., PNAS 100(23):13525-13530 (2003).

Recently, TPH knockout mice were studied in a hypoxia-induced pulmonary arterial hypertension model. Morecroft, I., et al., Hypertension 49:232-236 (2007). The results of those studies suggest that TPH1 and peripheral serotonin play an essential role in the development of hypoxia-induced elevations in pulmonary pressures and hypoxia-induced pulmonary vascular remodeling.

The PGI2 receptor agonists disclosed herein, alone or in combination with a tryptophan hydroxylase inhibitor, are useful in the treatment of pulmonary arterial hypertension (PAH) and symptoms thereof.

2. Antiplatelet Therapies (Conditions Related to Platelet Aggregation)

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction ("MI" or "heart attack"), the heart muscle does not receive enough oxygen-rich blood as a result of a blockage in the coronary blood vessels. If taken while an attack is in progress or immediately afterward (preferably within 30 min), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

There is evidence that a PGI2 receptor agonist will inhibit platelet aggregation and thus be a potential treatment as an antiplatelet therapy (see, e.g., Moncada et al., Lancet, 1977, 1:18-20). It has been shown that genetic deficiency of the PGI2 receptor in mice leads to an increased propensity towards thrombosis (Murata et al., Nature, 1997, 388:678-682).

PGI2 receptor agonists can be used to treat, for example, claudication or peripheral artery disease as well as cardiovascular complications, arterial thrombosis, atherosclerosis, vasoconstriction caused by serotonin, ischemia-reperfusion injury, and restenosis of arteries following angioplasty or stent placement. (See, e.g., Fetalvero et al., Prostaglandins Other Lipid Mediat., 2007, 82:109-118; Arehart et al., Curr. Med. Chem., 2007, 14:2161-2169; Davi et al., N. Engl. J. Med., 2007, 357:2482-2494; Fetalvero et al., Am. J. Physiol. Heart. Circ. Physiol., 2006, 290:H1337-H1346; Murata et al., Nature, 1997, 388:678-682; Wang et al., Proc. Natl. Acad. Sci. USA, 2006, 103:14507-14512; Xiao et al., Circulation, 2001, 104:2210-2215; McCormick et al., Biochem. Soc. Trans., 2007, 35:910-911; Arehart et al., Circ. Res., 2008, 102(8), 986-93.)

PGI2 receptor agonists can also be used alone or in combination with thrombolytic therapy, for example, tissue-type plasminogen activator (t-PA), to provide cardioprotection following MI or postischemic myocardial dysfunction or protection from ischemic injury during percutaneous coronary intervention, and the like, including complications resulting therefrom. PGI2 receptor agonists can also be used in antiplatelet therapies in combination with, for example, alpha-tocopherol (vitamin E), echistatin (a disintegrin) or, in states of hypercoagulability, heparin. (See, e.g., Chan., J. Nutr., 1998, 128:1593-1596; Mardla et al., Platelets, 2004, 15:319-324; Bernabei et al., Ann. Thorac. Surg., 1995, 59:149-153; Gainza et al., J. Nephrol., 2006, 19:648-655.)

The PGI2 receptor agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof, comprising administering to the patient a composition comprising a PGI2 receptor agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising a PGI2 receptor agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising a PGI2 receptor agonist disclosed herein at a time where such risk exists.

3. Atherosclerosis

Atherosclerosis is a complex disease characterized by inflammation, lipid accumulation, cell death and fibrosis. It is the leading cause of mortality in many countries, including the United States. Atherosclerosis, as the term is used herein, shall be understood to encompass disorders of large and medium-sized arteries that result in the progressive accumulation within the intima of smooth muscle cells and lipids.

It has been shown that an agonist of the PGI2 receptor can confer protection from atherosclerosis, such as from atherothrombosis (Arehart et al., Curr. Med. Chem., 2007, 14:2161-

2169; Stitham et al., Prostaglandins Other Lipid Mediat., 2007, 82:95-108; Fries et al., Hematology Am. Soc. Hematol. Educ. Program, 2005, :445-451; Egan et al., Science, 2004, 306:1954-1957; Kobayashi et al., J. Clin. Invest., 2004, 114: 784-794; Arehart et al., Circ. Res., 2008, 102(8), 986-93).

It has been shown that defective PGI2 receptor signaling appears to accelerate atherothrombosis in humans, i.e. that an agonist of the PGI2 receptor can confer protection from atherothrombosis in humans (Arehart et al., Circ. Res., 2008, 102(8), 986-93).

The compounds of the present invention disclosed herein are useful in the treatment of atherosclerosis, and the treatment of the symptoms thereof. Accordingly, in some embodiments, the present invention provides methods for treating atherosclerosis in a patient in need of the treatment, comprising administering to the patient a composition comprising a PGI2 receptor agonist disclosed herein. In further embodiments, methods are provided for treating a symptom of atherosclerosis in a patient in need of the treatment, comprising administering to the patient a composition comprising a PGI2 receptor agonist disclosed herein.

4. Asthma

Asthma is a lymphocyte-mediated inflammatory airway disorder characterized by airway eosinophilia, increased mucus production by goblet cells, and structural remodeling of the airway wall. The prevalence of asthma has dramatically increased worldwide in recent decades. It has been shown that genetic deficiency of the PGI2 receptor in mice augments allergic airway inflammation (Takahashi et al., Br J Pharmacol, 2002, 137:315-322). It has been shown that an agonist of the PGI2 receptor can suppress not only the development of asthma when given during the sensitization phase, but also the cardinal features of experimental asthma when given during the challenge phase (Idzko et al., J. Clin. Invest., 2007, 117: 464-472; Nagao et al., Am. J. Respir. Cell Mol. Biol., 2003, 29:314-320), at least in part through markedly interfering with the function of antigen-presenting dendritic cells within the airways (Idzko et al., J. Clin. Invest., 2007, 117:464-472; Zhou et al., J. Immunol., 2007, 178:702-710; Jaffar et al., J. Immunol., 2007, 179:6193-6203; Jozefowski et al., Int. Immunopharmacol., 2003, 3:865-878). These cells are crucial for both the initiation and the maintenance phases of allergic asthma, as depletion of airway dendritic cells during secondary challenge in sensitized mice abolished all characteristic features of asthma, an effect that could be completely restored by adoptive transfer of wild-type dendritic cells (van Rijt et al., J. Exp. Med., 2005, 201:981-991). It has also been shown that an agonist of the PGI2 receptor can inhibit proinflammatory cytokine secretion by human alveolar macrophages (Raychaudhuri et al., J. Biol. Chem., 2002, 277:33344-33348). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising a PGI2 receptor agonist disclosed herein. In further embodiments, methods are provided for treating a symptom of asthma in a patient in need of the treatment, comprising administering to the patient a composition comprising a PGI2 receptor agonist disclosed herein.

5. Diabetic-Related Pathologies

Although hyperglycemia is the major cause for the pathogenesis of diabetic complications such as diabetic peripheral neuropathy (DPN), diabetic nephropathy (DN) and diabetic retinopathy (DR), enhanced vasoconstriction and platelet aggregation in diabetic patients has also been implicated to play a role in disease progression (Cameron et al., Naunyn Schmiedebergs Arch. Pharmacol., 2003, 367:607-614). Agonists of the PGI2 receptor promote vasodilation and inhibit platelet aggregation. Improving microvascular blood flow is able to benefit diabetic complications (Cameron, Diabetologia, 2001, 44:1973-1988).

It has been shown that an agonist of the PGI2 receptor can prevent and reverse motor and sensory peripheral nerve conduction abnormalities in streptozotocin-diabetic rats (Cotter et al., Naunyn Schmiedebergs Arch. Pharmacol., 1993, 347: 534-540). Further evidence for the beneficial effect of an agonist of the PGI2 receptor in the treatment of diabetic peripheral neuropathy is given by Hotta et al. (Diabetes, 1996, 45:361-366), Ueno et al. (Jpn. J. Pharmacol., 1996, 70:177-182), Ueno et al. (Life Sci., 1996, 59:PL105-PL110), Hotta et al. (Prostaglandins, 1995, 49:339-349), Shindo et al. (Prostaglandins, 1991, 41:85-96), Okuda et al. (Prostaglandins, 1996, 52:375-384), and Koike et al. (FASEB J., 2003, 17:779-781). Evidence for the beneficial effect of an agonist of the PGI2 receptor in the treatment of diabetic nephropathy is given by Owada et al. (Nephron, 2002, 92:788-796) and Yamashita et al. (Diabetes Res. Clin. Pract., 2002, 57:149-161). Evidence for the beneficial effect of an agonist of the PGI2 receptor in the treatment of diabetic retinopathy is given by Yamagishi et al. (Mol. Med., 2002, 8:546-550), Burnette et al. (Exp. Eye Res., 2006, 83:1359-1365), and Hotta et al. (Diabetes, 1996, 45:361-366). It has been shown that an agonist of the PGI2 receptor can reduce increased tumor necrosis factor-α (TNF-α) levels in diabetic patients, implying that an agonist of the PGI2 receptor may contribute to the prevention of progression in diabetic complications (Fujiwara et al., Exp. Clin. Endocrinol. Diabetes, 2004, 112:390-394).

6. Glaucoma

Evidence that topical administration of an agonist of the PGI2 receptor can result in a decrease in intraocular pressure (IOP) in rabbits and dogs and thereby have beneficial effect in the treatment of glaucoma is given by Hoyng et al. (Hoyng et al., Invest. Ophthalmol. Vis. Sci., 1987, 28:470-476).

7. Hypertension

Agonists of the PGI2 receptor have been shown to have activity for regulation of vascular tone, for vasodilation, and for amelioration of pulmonary hypertension (see, e.g., Strauss et al., Clin Chest Med, 2007, 28:127-142; Driscoll et al., Expert Opin. Pharmacother., 2008, 9:65-81). Evidence for a beneficial effect of an agonist of the PGI2 receptor in the treatment of hypertension is given by Yamada et al. (Peptides, 2008, 29:412-418). Evidence that an agonist of the PGI2 receptor can protect against cerebral ischemia is given by Dogan et al. (Gen. Pharmacol., 1996, 27:1163-1166) and Fang et al. (J. Cereb. Blood Flow Metab., 2006, 26:491-501).

8. Anti-Inflammation Therapies

Anti-inflammation agents are prescribed for a variety of conditions. For example, in an inflammatory disease they are used to interfere with and thereby reduce an underlying deleterious There is evidence that a PGI2 receptor agonist can inhibit inflammation and thus be a potential treatment as an anti-inflammation therapy. It has been shown that an agonist of the PGI2 receptor can inhibit pro-inflammatory cytokine and chemokine (interleukin-12 (IL-12), tumor necrosis factor-α (TNF-α), IL-1α, IL-6, macrophage inflammatory protein-1alpha (MIP-1α), monocyte chemoattractant protein-1 (MCP-1)) production and T cell stimulatory function of dendritic cells (Jozefowski et al., Int. Immunopharmacol., 2003, 865-878; Zhou et al., J. Immunol., 2007, 178:702-710; Nagao et al., Am. J. Respir. Cell Mol. Biol., 2003, 29:314-320; Idzko et al., J. Clin. Invest., 2007, 117:464-472). It has been shown that an agonist of the PGI2 receptor can inhibit pro-inflammatory cytokine (TNF-α, IL-1β, IL-6, granulocyte macrophage stimulating factor (GM-CSF)) production by macrophages (Raychaudhuri et al., J. Biol. Chem., 2002, 277:33344-33348; Czeslick et al., Eur. J. Clin. Invest., 2003, 33:1013-1017; Di Renzo et al., Prostaglandin Leukot. Essent. Fatty Acids, 2005, 73:405-410; Shinomiya et al., Biochem. Pharmacol., 2001, 61:1153-1160). It has been shown that an agonist of the PGI2 receptor can stimulate anti-inflammatory cytokine (IL-10) production by dendritic cells (Jozefowski et al., Int. Immunopharmacol., 2003, 865-878; Zhou et al., J. Immunol., 2007, 178:702-710). It has been shown that an agonist of the PGI2 receptor can stimulate anti-inflammatory cytokine (IL-10) production by macrophages (Shinomiya et al., Biochem. Pharmacol., 2001, 61:1153-1160). It has been shown that an agonist of the PGI2 receptor can inhibit a chemokine (CCL17)-induced chemotaxis of leukocytes ($CD4^+$ Th2 T cells) (Jaffar et al., J. Immunol., 2007, 179: 6193-6203). It has been shown that an agonist of the PGI2 receptor can confer protection from atherosclerosis, such as from atherothrombosis (Arehart et al., Curr. Med. Chem., 2007, 14:2161-2169; Stitham et al., Prostaglandins Other Lipid Mediat., 2007, 82:95-108; Fries et al., Hematology Am. Soc. Hematol. Educ. Program, 2005, :445-451; Egan et al., Science, 2004, 306:1954-1957; Kobayashi et al., J. Clin. Invest., 2004, 114:784-794; Arehart et al., Circ. Res., 2008, 102(8), 986-93). It has been shown that an agonist of the PGI2 receptor can attenuate asthma (Idzko et al., J. Clin. Invest., 2007, 117:464-472; Jaffar et al., J. Immunol., 2007, 179: 6193-6203; Nagao et al., Am. J. Respir. Cell. Mol. Biol., 2003, 29:314-320). It has been shown that an agonist of the PGI2 receptor can decrease TNF-α production in type 2 diabetes patients (Fujiwara et al., Exp. Clin. Endocrinol. Diabetes, 2004, 112:390-394; Goya et al., Metabolism, 2003, 52:192-198). It has been shown that an agonist of the PGI2 receptor can inhibit ischemia-reperfusion injury (Xiao et al., Circulation, 2001, 104:2210-2215). It has been shown that an agonist of the PGI2 receptor can inhibit restenosis (Cheng et al., Science, 2002, 296:539-541). It has been shown that an agonist of the PGI2 receptor can attenuate pulmonary vascular injury and shock in a rat model of septic shock (Harada et al., Shock, 2008, Feb. 21 Epub ahead of print). It has been shown that an agonist of the PGI2 receptor can reduce the serum levels of TNF-α in vivo in patients with rheumatoid arthritis, and this is associated with improvement in the clinical course of the disease (Gao et al., Rheumatol. Int., 2002, 22:45-51; Boehme et al., Rheumatol. Int., 2006, 26:340-347).

The compounds of the present invention disclosed herein provide beneficial reduction of inflammation. The compounds of the present invention disclosed herein provide beneficial reduction of a deleterious inflammatory response associated with an inflammatory disease. Accordingly, in some embodiments, the present invention provides methods for reducing inflammation in a patient in need thereof, comprising administering to the patient a composition comprising a PGI2 receptor agonist disclosed herein. In some embodiments, the present invention provides methods for decreasing IL-12, TNF-α, IL-1α, IL-1β, IL-6, MIP-1α or MCP-1 production in a patient in need thereof, comprising administering to the patient a composition comprising a PGI2 receptor agonist disclosed herein. In some embodiments, the present invention provides methods for decreasing TNF-α production in a patient in need thereof, comprising administering to the patient a composition comprising a PGI2 receptor agonist disclosed herein. In some embodiments, the present invention provides methods for increasing IL-10 production in a patient in need thereof, comprising administering to the patient a composition comprising a PGI2 receptor agonist disclosed herein. In some embodiments, the present invention provides methods for reducing a deleterious inflammatory response associated with an inflammatory disease in a patient in need thereof, comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein. In some embodiments, the present invention provides methods for treating an inflammatory disease or a symptom thereof in a patient in need of the treatment comprising administering to the patient a composition comprising a PGI2 receptor agonist disclosed herein, wherein the inflammatory disease is selected from the group consisting of psoriasis, psoriatic arthritis, rheumatoid arthritis, Crohn's disease, transplant rejection, multiple sclerosis, systemic lupus erythematosus (SLE), ulcerative colitis, ischemia-reperfusion injury, restenosis, atherosclerosis, acne, diabetes (including type 1 diabetes and type 2 diabetes), sepsis, chronic obstructive pulmonary disease (COPD), and asthma.

9. Traumatic Brain Injury

Prostacyclin production is known to increase after brain trauma, and in a recent study, the importance of prostacyclin for posttraumatic hemodynamic alterations and neuron survival was investigated. Prostacyclin receptor-deficient ($IP^{-/-}$) mice were compared to mice with functional prostacyclin receptors ($IP^{+/+}$) after a controlled cortical injury. Contusion volume was increased in $IP^{-/-}$ mice compared with $IP^{+/+}$ mice. Three hours after trauma, cortical blood flow was decreased in the injured cortex of both groups and the reduction in blood flow in the cortex of the $IP^{-/-}$ mice persisted from 3 to 24 h, whereas blood flow approached normal values in the $IP^{+/+}$ mice after 24 h. (See, e.g., Lundblad et al. Journal of Cerebral Blood Flow & Metabolism (2008) 28, 367-376).

The PGI2 receptor agonists disclosed herein provide beneficial improvement in neuron survival after brain trauma. Accordingly, in some embodiments, the present invention provides methods for treating a traumatic brain injury in a patient in need thereof, comprising administering to the patient a composition comprising a PGI2 receptor agonist disclosed herein.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate, hydrate or physiologically functional derivative thereof can be used as active ingredients in pharmaceutical compositions, specifically as PGI2 receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size. The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed, as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Certain compounds of the present invention which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1,N^2$-dibenzylethane-1,2-diamine), chloroprocaine (2-(diethylamino)ethyl 4-(chloroamino)benzoate), choline, diethanolamine, ethylenediamine, meglumine ((2R,3R,4R,5S)-6-(methylamino)hexane-1,2,3,4,5-pentaol), procaine (2-(diethylamino)ethyl 4-aminobenzoate), and the like. Certain pharmaceutically acceptable salts are listed in Berge, et al., *Journal of Pharmaceutical Sciences,* 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design,* ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the PGI2 receptor modulators are utilized as active ingredients in a pharmaceutical composition, these are not intended for use only in humans, but in other non-human mammals as well. Indeed, recent advances in the area of animal health-care mandate that consideration be given for the use of active agents, such as PGI2 receptor modulators, for the treatment of an PGI2-associated disease or disorder in companionship animals (e.g., cats, dogs, etc.) and in livestock animals (e.g., cows, chickens, fish, etc.) Those of ordinary skill in the art are readily credited with understanding the utility of such compounds in such settings.

Hydrates and Solvates

It is understood that when the phrase pharmaceutically acceptable salts, solvates and hydrates is used in referring to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: *Polymorphism in Pharmaceutical Solids*, ed. Harry G. Brittan, Vol. 95, Marcel Dekker, Inc., New York, 1999, incorporated herein by reference in its entirety. Accordingly, one aspect of the present invention pertains to hydrates and solvates of compounds of Formula Ia and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Pro-Drugs of the Present Invention

The compounds of Formula Ia may be administered in the form of a pro-drug which is broken down in the human or animal body to give a compound of the Formula Ia. Pro-drugs of the present invention may employ any pro-drug strategy known in the art. A pro-drug may be used to alter or improve the physical and/or pharmacokinetic profile of the parent compound and can be formed when the parent compound contains a suitable group or substituent which can be derivatized to form a pro-drug. Examples of pro-drugs include in-vivo hydrolyzable amides of a compound of the Formula Ia or pharmaceutically-acceptable salts thereof.

One aspect of the present invention pertains to compounds of Formula II useful as pro-drugs for the delivery of compounds of Formula Ia:

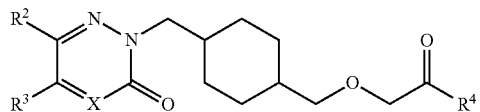

II wherein:

$R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen;

X is selected from: N and CH; and $R^4$ is a radical derived from any natural or unnatural amino acid, upon the loss of a hydrogen atom from the α-amino group of said natural or unnatural amino acid; or $R^4$ is —NHCH$_2$CH$_2$SO$_3$H.

One aspect of the present invention pertains to compounds of Formula IIa useful as pro-drugs for the delivery of compounds of Formula Ia:

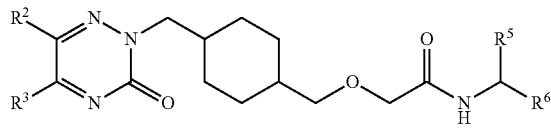

IIa wherein:

$R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen;

$R^5$ is selected from: H and carboxyl; and $R^6$ is selected from: H and $C_1$-$C_6$ alkyl; wherein $C_1$-$C_6$ alkyl is optionally substituted with 4-hydroxyphenyl, amino, carboxamide, carboxyl, guanidino, hydroxyl, imidazolyl, indolyl, methylthio, phenyl, pyrrolidinyl, sulfo and thiol.

In some embodiments, $R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

In some embodiments, $R^2$ is aryl optionally substituted with one or more $C_1$-$C_8$ alkyl substituents.

In some embodiments, $R^2$ is p-tolyl.

In some embodiments, $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy and halogen.

In some embodiments, $R^3$ is phenyl.

In some embodiments, $R^5$ is H; and $R^6$ is —CH$_2$SO$_3$H.

In some embodiments, $R^5$ is carboxyl; and $R^6$ is H.

In some embodiments: $R^2$ is p-tolyl; $R^3$ is phenyl; $R^5$ is H; and $R^6$ is —CH$_2$SO$_3$H.

In some embodiments: $R^2$ is p-tolyl; $R^3$ is phenyl; $R^5$ is carboxyl; and $R^5$ is H.

Certain pro-drugs of compounds of the present invention are described in Examples 1.88 and 1.89.

Other Utilities

Another object of the present invention relates to radio-labeled compounds of the present invention that would be useful not only in radio-imaging but also in assays, both in vitro and in vivo, for localizing and quantitating the PGI2 receptor in tissue samples, including human and for identifying PGI2 receptor ligands by inhibition binding of a radio-labeled compound. It is a further object of this invention to develop novel PGI2 receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PGI2 receptor labeling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of Formula Ia, Ic, Ie, Ig, or Ii that has incorporated at least one radionuclide; in some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl (3H) products by treating appropriate precursors with high specific activity methyl iodide [$^3$H]: This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled PGI2 receptor compound of Formula Ia can be used in a screening assay to identify/evaluate compounds. In general terms, a newly synthesized or identified compound (i.e., test compound) can be evaluated for its ability to reduce binding of the "radio-labeled compound of Formula Ia" to the PGI2 receptor. Accordingly, the ability of a test compound to compete with the "radio-labeled compound of Formula Ia" for the binding to the PGI2 receptor directly correlates to its binding affinity.

The labeled compounds of the present invention bind to the PGI2 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM and in still yet another embodiment the labeled inhibitor has an IC$_{50}$ less than about 0.1 µM.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1

Syntheses of Compounds of the Present Invention

Illustrated syntheses for compounds of the present invention are shown in FIGS. 2 through 6 where the symbols have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Chemistry:

Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, m=multiplet, bs=broad singlet, bt=broad triplet. Microwave irradiations were carried out using a Smith Synthesizer or an Emrys Optimizer™ (Biotage). Thin-layer chromatography (TLC) was performed on silica gel 60 F$_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1

Preparation of 2-(((1s,4s)-4-((3-Oxo-5-phenyl-6-p-tolyl-1,2,4-triazin-2(3H)-yl)methyl)cyclohexyl)methoxy)acetic Acid (Compound 68) and Sodium Salt Thereof Step A: Preparation of 2-(Hydroxyimino)-2-phenyl-1-p-tolylethanone To a solution of 2-phenyl-1-p-tolylethanone (5.0 g, 23.78 mmol) in EtOH (475.0 mL) at room temperature was added dropwise tert-butyl nitrite (5.5 mL, 46.2 mmol) followed by sodium ethoxide (4.07 g, 59.8 mmol). The reaction was stirred at room temperature overnight and concentrated under reduced pressure. The residue was dissolved in EtOAc, washed with $H_2O$, brine, dried over $MgSO_4$ and concentrated. The residue was purified by silica gel column chromatography to give the title compound as an orange oil (5.31 g). LCMS m/z=239.9 $[M+H]^+$.

Step B: Preparation of 3-(Methylthio)-5-phenyl-6-p-tolyl-1,2,4-triazine

To a suspension of 2-(hydroxyimino)-2-phenyl-1-p-tolylethanone (1.99 g, 8.32 mmol) in a 1:1 mixture of $MeOH/H_2O$ (40.0 mL) was added hydrazinecarbothioamide (1.134 g, 12.44 mmol) followed by concentrated HCl (0.75 mL, 24.68 mmol). The reaction was stirred at room temperature for 1 h then at 60° C. overnight. Additional hydrazinecarbothioamide (~3×100 mg) was added portionwise and the reaction was stirred at 60° C. until the starting material was consumed. The reaction was neutralized with saturated $NaHCO_3$. The solid was removed by filtration and rinsed with $H_2O$. To the solid was added a solution of potassium carbonate (5.78 g, 41.8 mmol) in $H_2O$ (85 mL) and the mixture was heated at 90° C. overnight. The reaction mixture was cooled to room temperature then placed in an ice bath. Iodomethane (0.52 mL, 8.35 mmol) was added and the reaction was stirred at 0° C. and then slowly warmed to room temperature. After stirring overnight, the solution was decanted. The solid was dissolved in $CH_2Cl_2$, and the solution was washed with $H_2O$ and brine, dried over $MgSO_4$, and concentrated. The residue was purified by silica gel column chromatography to give the title compound as a yellow solid (1.302 g). LCMS m/z=294.2 $[M+H]^+$.

Step C: Preparation of 3-(Methylsulfonyl)-5-phenyl-6-p-tolyl-1,2,4-triazine

To a solution of 3-(methylthio)-5-phenyl-6-p-tolyl-1,2,4-triazine (1.302 g, 4.44 mmol) in $CH_2Cl_2$ (25.0 mL) at 0° C. was added MCPBA (2.06 g, 9.19 mmol). The reaction mixture was stirred at 0° C. and then warmed to room temperature. After 18 h, the reaction was quenched with saturated $NaHCO_3$ solution and extracted with $CH_2Cl_2$. The combined organic phases were washed with $H_2O$ and brine, dried over $MgSO_4$, and concentrated. The residue was purified by silica gel column chromatography to give the title compound as an off-white solid (1.69 g). LCMS m/z=326.2 $[M+H]^+$.

Step D: Preparation of 5-Phenyl-6-p-tolyl-1,2,4-triazin-3(2H)-one

To a solution of 3-(methylsulfonyl)-5-phenyl-6-p-tolyl-1,2,4-triazine (98.9 mg, 0.304 mmol) in a 1:1 mixture of $H_2O/$ THF (6.0 mL) was added potassium hydroxide (109.1 mg, 1.945 mmol). The mixture was heated at reflux for 1 h. The reaction mixture was cooled to room temperature and neutralized with 1 M HCl, then extracted with $CH_2Cl_2$. The combined organic phases were washed with $H_2O$ and brine, dried over $MgSO_4$, and concentrated to give the title compound as a yellow solid (73.7 mg). LCMS m/z=264.1 $[M+H]^+$.

Step E: Preparation of 2-(((1s,4s)-4-((3-Oxo-5-phenyl-6-p-tolyl-1,2,4-triazin-2(3H)-yl)methyl)cyclohexyl)methoxy)acetic Acid and Sodium Salt Thereof In a reaction vial was placed a mixture of 5-phenyl-6-p-tolyl-1,2,4-triazin-3(2H)-one (352.7 mg, 1.340 mmol) and sodium hydride (58.3 mg, 1.458 mmol) in DMF (3.0 mL). The reaction was stirred at room temperature for 15 min then added a solution of tert-butyl 2-(((1s,4s)-4-(tosyloxymethyl)cyclohexyl)methoxy)acetate (549.0 mg, 1.331 mmol) in DMF (6.0 mL). The mixture was heated at 45° C. Upon completion of the reaction, the mixture was quenched with $H_2O$ and extracted with EtOAc. The combined organics were washed with brine, dried over $MgSO_4$, and concentrated. The residue was purified by silica gel column chromatography. To the above purified material was added 4 M HCl (1.0 mL) in 1,4-dioxane and the mixture was stirred at room temperature overnight. Five drops of 10% NaOH solution was added and the mixture was extracted with MTBE. The combined organic phases were washed with brine, dried over $MgSO_4$, and concentrated. The residue was purified by HPLC to give the title compound free acid as a yellowish solid (289.1 mg). The free acid was dissolved in acetonitrile, 1 N aqueous sodium hydroxide (0.646 mL, 0.646 mmol) was added and the mixture was lyophilized to afford the sodium salt of the title compound as an off-white solid (304.8 mg). LCMS m/z=448.5 $[M+H]^+$; $^1$H NMR (400 M Hz, DMSO-$d_6$) δ ppm 1.34-1.54 (m, 7H), 1.67-1.79 (m, 2H), 2.12-2.22 (m, 1H), 2.29 (s, 3H), 3.36 (d, J=7.0 Hz, 2H), 3.74 (s, 2H), 4.09 (d, J=7.5 Hz, 2H), 7.14 (s, 4H), 7.25-7.34 (m, 4H), 7.36-7.42 (m, 1H).

Example 1.2

Preparation of 2-(((1s,4s)-4-((3-Oxo-5,6-di-p-tolyl-1,2,4-triazin-2(3H)-yl)methyl)cyclohexyl)methoxy)acetic Acid (Compound 43)

In a reaction vial was placed a mixture of 5,6-di-p-tolyl-1,2,4-triazin-3(2H)-one (73.3 mg, 0.264 mmol) and sodium hydride (13.8 mg, 0.345 mmol) in THF (1.0 mL). The reaction was stirred at room temperature for 30 min then added a solution of tert-butyl 2-(((1s,4s)-4-(tosyloxymethyl)cyclohexyl)methoxy)acetate (101.3 mg, 0.246 mmol) in THF (1.5 mL). DMF (1.0 mL) was added to the reaction mixture and it was heated at 50° C. for 45 h. Upon completion, the reaction was quenched with $H_2O$ and extracted with EtOAc. The combined organic layers were washed with brine, dried over $MgSO_4$, and concentrated. The residue was purified by silica gel column chromatography to give a yellow oil. To this oil was added 4 M HCl (0.50 mL, 2.0 mmol) in 1,4-dioxane and the mixture was stirred at room temperature overnight. Upon completion of the reaction, 10% NaOH solution (6 drops) was added and the reaction mixture was diluted with acetonitrile. The reaction mixture was filtered and purified by HPLC to give the title compound as a yellow solid (35.0 mg). LCMS m/z=462.3 $[M+H]^+$; $^1$H NMR (400 M Hz, DMSO-$d_6$) δ ppm 1.36-1.54 (m, 7H), 1.68-1.79 (m, 2H), 2.12-2.21 (m, 1H), 2.29-2.32 (m, 6H), 3.39 (d, J=6.9 Hz, 2H), 3.98 (s, 2H), 4.08 (d, J=7.5 Hz, 2H), 7.14-7.18 (m, 6H), 7.28-7.31 (m, 2H).

Example 1.3

Preparation of 2-(((1s,4s)-4-((3-Oxo-5,6-diphenyl-1,2,4-triazin-2(3H)-yl)methyl)cyclohexyl)methoxy) acetic Acid (Compound 48)

From 5,6-diphenyl-1,2,4-triazin-3(2H)-one, the title compound was prepared using a similar method to the one described in Example 1.1, Step E. LCMS m/z=434.4 [M+H]$^+$; $^1$H NMR (400 M Hz, DMSO-d$_6$) δ ppm 1.39-1.54 (m, 7H), 1.69-1.80 (m, 2H), 2.14-2.23 (m, 1H), 3.40 (d, J=6.9 Hz, 2H), 3.99 (s, 2H), 4.10 (d, J=7.5 Hz, 2H), 7.24-7.49 (m, 10H).

Example 1.4

Preparation of 2-(((1s,4s)-4-((5,6-Bis(4-fluorophenyl)-3-oxo-1,2,4-triazin-2(3H)-yl)methyl)cyclohexyl)methoxy)acetic Acid (Compound 49)

From 5,6-bis(4-fluorophenyl)-1,2,4-triazin-3(2H)-one, the title compound was prepared using a similar method to the one described Example 1.1, Step E to give a yellow solid. $^1$H NMR (400 M Hz, DMSO-d$_6$) δ ppm 1.39-1.55 (m, 7H), 1.69-1.80 (m, 2H), 2.13-2.21 (m, 1H), 3.38 (d, J=6.8 Hz, 2H), 3.95 (s, 2H), 4.09 (d, J=7.5 Hz, 2H), 7.17-7.25 (m, 4H), 7.29-7.35 (m, 2H), 7.41-7.47 (m, 2H).

Example 1.5

Preparation of 2-(((1s,4s)-4-((6-(4-Fluorophenyl)-3-oxo-5-phenyl-1,2,4-triazin-2(3H)-yl)methyl)cyclohexyl)methoxy)acetic Acid (Compound 64)

From 1-(4-fluorophenyl)-2-phenylethanone, the title compound was prepared using a similar method to the one described in Example 1.1 to give a yellow solid. LCMS m/z=452.3 [M+H]$^+$. LCMS m/z=452.3 [M+H]$^+$; $^1$H NMR (400 M Hz, DMSO-d$_6$) δ ppm 1.38-1.55 (m, 7H), 1.70-1.80 (m, 2H), 2.14-2.22 (m, 1H), 3.40 (d, J=6.9 Hz, 2H), 3.99 (s, 2H), 4.10 (d, J=7.5 Hz, 2H), 7.15-7.50 (m, 9H).

Example 1.6

Preparation of 2-(((1s,4s)-4-((5-(3-Chlorophenyl)-3-oxo-6-phenyl-1,2,4-triazin-2(3H)-yl)methyl)cyclohexyl)methoxy)acetic Acid (Compound 67)

From 2-(3-chlorophenyl)-1-phenylethanone, the title compound was prepared using a similar method to the one described in Example 1.1 to give a yellow solid. LCMS m/z=468.4 [M+H]$^+$; $^1$H NMR (400 M Hz, DMSO-d$_6$) δ ppm 1.38-1.55 (m, 7H), 1.70-1.80 (m, 2H), 2.14-2.22 (m, 1H), 3.40 (d, J=6.9 Hz, 2H), 3.99 (s, 2H), 4.11 (d, J=7.5 Hz, 2H), 7.25-7.54 (m, 9H).

Example 1.7

Preparation of 2-(((1s,4s)-4-((6-(4-Methoxyphenyl)-3-oxo-5-phenyl-1,2,4-triazin-2(3H)-yl)methyl)cyclohexyl)methoxy)acetic Acid (Compound 69)

From 1-(4-methoxyphenyl)-2-phenylethanone, the title compound was prepared using a similar method to the one described in Example 1.1 to give a yellow solid. LCMS m/z=464.5 [M+H]$^+$; $^1$H NMR (400 M Hz, DMSO-d$_6$) δ ppm 1.40-1.54 (m, 7H), 1.68-1.80 (m, 2H), 2.14-2.22 (m, 1H), 3.39 (d, J=6.9 Hz, 2H), 3.75 (s, 3H), 3.99 (s, 2H), 4.09 (d, J=7.5 Hz, 2H), 6.86-7.81 (m, 9H).

Example 1.8

Preparation of 2-(((1s,4s)-4-((5-(3-Methoxyphenyl)-3-oxo-6-phenyl-1,2,4-triazin-2(3H)-yl)methyl)cyclohexyl)methoxy)acetic Acid (Compound 70)

From 2-(3-methoxyphenyl)-1-phenylethanone, the title compound was prepared using a similar method to the one described in Example 1.1 to give a yellow solid. LCMS m/z=464.3 [M+H]$^+$; $^1$H NMR (400 M Hz, DMSO-d$_6$) δ ppm 1.39-1.54 (m, 7H), 1.70-1.80 (m, 2H), 2.15-2.22 (m, 1H), 3.39 (d, J=6.9 Hz, 2H), 3.60 (s, 3H), 3.99 (s, 2H), 4.10 (d, J=7.5 Hz, 2H), 6.91-7.03 (m, 3H), 7.22-7.41 (m, 6H).

Example 1.9

Preparation of 2-(((1s,4s)-4-((6-(2-Fluoro-4-methylphenyl)-3-oxo-5-phenyl-1,2,4-triazin-2(3H)-yl) methyl)cyclohexyl)methoxy)acetic Acid (Compound 71)

From 1-(2-fluoro-4-methylphenyl)-2-phenylethanone, the title compound was prepared using a similar method to the one described in Example 1.1 to give a yellow solid. LCMS m/z=466.3 [M+H]$^+$; $^1$H NMR (400 M Hz, DMSO-d$_6$) δ ppm 1.36-1.54 (m, 7H), 1.69-1.80 (m, 2H), 2.12-2.21 (m, 1H), 2.33 (s, 3H), 3.39 (d, J=6.9 Hz, 2H), 3.98 (s, 2H), 4.10 (d, J=7.5 Hz, 2H), 6.94-6.98 (m, 1H), 7.11-7.15 (m, 1H), 7.32-7.49 (m, 6H).

Example 1.10

Preparation of 2-(((1s,4s)-4-((6-(4-Chlorophenyl)-3-oxo-5-phenyl-1,2,4-triazin-2(3H)-yl)methyl)cyclohexyl)methoxy)acetic Acid (Compound 72)

From 1-(4-chlorophenyl)-2-phenylethanone, the title compound was prepared using a similar method to the one described in Example 1.1 to give a yellow solid. LCMS m/z=468.5 [M+H]$^+$; $^1$H NMR (400 M Hz, DMSO-d$_6$) δ ppm 1.38-1.54 (m, 7H), 1.70-1.80 (m, 2H), 2.13-2.22 (m, 1H), 3.40 (d, J=6.9 Hz, 2H), 3.99 (s, 2H), 4.10 (d, J=7.5 Hz, 2H), 7.25-7.30 (m, 2H), 7.35-7.50 (m, 7H).

Example 1.11

Preparation of 2-(((1r,4r)-4-((6-(2-Fluoro-4-methylphenyl)-3-oxo-5-phenyl-1,2,4-triazin-2(3H)-yl) methyl)cyclohexyl)methoxy)acetic Acid (Compound 75)

A reaction vial was charged with 6-(2-fluoro-4-methylphenyl)-5-phenyl-1,2,4-triazin-3(2H)-one (from Example 1.9) (102.9 mg, 0.366 mmol), cesium carbonate (133.8 mg, 0.411 mmol) and tert-butyl 2-(((1r,4r)-4-(tosyloxymethyl)cyclohexyl)methoxy)acetate (152.3 mg, 0.369 mmol) in DMF (5.0 mL). The reaction mixture was stirred at 60° C. overnight. Upon completion, the reaction was quenched with H$_2$O and extracted with EtOAc. The combined organic layers were washed with brine, dried over MgSO$_4$, and concentrated. The residue was purified by silica gel column chromatography to give tert-butyl 2-(((1r,4r)-4-((6-(2-fluoro-4-methylphenyl)-3-oxo-5-phenyl-1,2,4-triazin-2(3H)-yl)methyl)cyclohexyl)methoxy)acetate as a colorless oil (108.5 mg). To this was added 4 M HCl (2.0 mL, 8.0 mmol) in 1,4-dioxane at room temperature. The reaction was stirred overnight and concentrated under reduced pressure. The residue was dissolved in acetonitrile, filtered and purified by HPLC to give the title compound as a yellow solid (66.7 mg). LCMS m/z=466.5 [M+H]+; $^1$H NMR (400 M Hz, DMSO-$d_6$) δ ppm 0.86-0.99 (m, 2H), 1.01-1.13 (m, 2H), 1.45-1.58 (m, 1H), 1.69-1.80 (m, 4H), 1.84-1.96 (m, 1H), 2.33 (s, 3H), 3.26 (d, J=6.4 Hz, 2H), 3.95 (s, 2H), 3.99 (d, J=7.1 Hz, 2H), 6.96 (d, J=11.1 Hz, 1H), 7.13 (d, J=7.8 Hz, 1H), 7.32-7.49 (m, 6H).

Example 1.12

Preparation of 2-(((1r,4r))-4-((3-Oxo-5-phenyl-6-p-tolyl-1,2,4-triazin-2(3H)-yl)methyl)cyclohexyl)methoxy)acetic Acid (Compound 76)

From 5-phenyl-6-p-tolyl-1,2,4-triazin-3(2H)-one, the title compound was prepared using a similar method to the one described in Example 1.11 to give a yellow solid. LCMS m/z=448.3 [M+H]+; $^1$H NMR (400 M Hz, DMSO-$d_6$) δ ppm 0.86-0.99 (m, 2H), 1.02-1.14 (m, 2H), 1.46-1.58 (m, 1H), 1.70-1.80 (m, 4H), 1.85-1.98 (m, 1H), 2.30 (s, 3H), 3.255 (d, J=6.4 Hz, 2H), 3.95 (s, 2H), 3.99 (d, J=7.1 Hz, 2H), 7.15 (s, 4H), 7.26-7.49 (m, 5H).

Example 1.13

Preparation of 2-(((1s,4s)-4-((5-(3-Fluorophenyl)-3-oxo-6-phenyl-1,2,4-triazin-2(3H)-yl)methyl)cyclohexyl)methoxy)acetic Acid (Compound 74)

Step A: Preparation of 2-(3-Fluorophenyl)-2-(hydroxyimino)-1-phenylethanone

From 2-(3-fluorophenyl)-1-phenylethanone, the title compound was prepared using a similar method to the one described in Example 1.1, Step A to give a yellow solid. LCMS m/z=244.2[M+H]+.

Step B: Preparation of 5-(3-Fluorophenyl)-3-(methylthio)-6-phenyl-1,2,4-triazine From 2-(3-fluorophenyl)-2-(hydroxyimino)-1-phenylethanone, the title compound was prepared using a similar method to the one described in Example 1.1, Step B to give a yellow solid. $^1$H NMR (400 M Hz, DMSO-$d_6$) δ ppm 2.72 (s, 3H), 7.45-7.50 (m, 3H), 7.38-7.45 (m, 3H), 7.24-7.36 (m, 3H).

Step C: Preparation of 5-(3-Fluorophenyl)-3-(methylsulfonyl)-6-phenyl-1,2,4-triazine From 5-(3-fluorophenyl)-3-(methylthio)-6-phenyl-1,2,4-triazine, the title compound was prepared using a similar method to the one described in Example 1.1, Step C to give a yellow solid. $^1$H NMR (400 M Hz, DMSO-$d_6$) δ ppm 3.61 (s, 3H), 7.55-7.60 (m, 2H), 7.52-7.55 (m, 1H), 7.44-7.51 (m, 3H), 7.33-7.43 (m, 3H).

Step D: Preparation of 5-(3-Fluorophenyl)-6-phenyl-1,2,4-triazin-3(2H)-one

From 5-(3-fluorophenyl)-3-(methylsulfonyl)-6-phenyl-1,2,4-triazine, the title compound was prepared using a similar method to the one described in Example 1.1, Step D to give a white solid. $^1$H NMR (400 M Hz, DMSO-$d_6$) δ ppm 7.11-7.24 (m, 3H), 7.31-7.43 (m, 4H), 7.25-7.31 (m, 2H), 13.60 (s, 1H).

Step E: Preparation of tert-Butyl 2-(((1s,4s)-4-((5-(3-Fluorophenyl)-3-oxo-6-phenyl-1,2,4-triazin-2(3H)-yl)methyl)cyclohexyl)methoxy)acetate To a solution of 5-(3-fluorophenyl)-6-phenyl-1,2,4-triazin-3(2H)-one (0.267 g, 1 mmol) in DMF (5 mL) was added $Cs_2CO_3$ (0.342 g, 1.05 mmol). The reaction was stirred for 15 min. A solution of tert-butyl 2-(((1s,4s)-4-(tosyloxymethyl)cyclohexyl)methoxy)acetate (0.413 g, 1.000 mmol) in DMF (5 mL) was added. The reaction was heated to 60° C. for 18 h. The reaction was cooled to room temperature and then diluted with water and extracted with EtOAc three times. The combined organic extracts were washed with brine, dried ($MgSO_4$) and concentrated. The residue was purified by silica gel column chromatography to give the title compound as a white solid (0.365 g). $^1$H NMR (400 M Hz, $CDCl_3$) δ ppm 1.48 (s, 9H), 1.52 (dd, J=6.32, 4.80 Hz, 1H), 1.55-1.66 (m, 6H), 1.83-1.93 (m, 2H), 2.35 (bs, 1H), 3.45 (d, J=7.07 Hz, 2H), 3.96 (s, 2H), 4.23 (d, J=7.58 Hz, 2H), 7.09-7.17 (m, 1H), 7.19-7.25 (m, 2H), 7.26-7.31 (m, 3H), 7.32-7.45 (m, 3H).

Step F: Preparation of 2-(((1s,4s)-4-((3-Oxo-6-phenyl-5-m-fluoro-1,2,4-triazin-2(3H)-yl)methyl)cyclohexyl)methoxy)acetic Acid To a solution of tert-butyl 2-(((1s,4s)-4-((5-(3-fluorophenyl)-3-oxo-6-phenyl-1,2,4-triazin-2(3H)-yl)methyl)cyclohexyl)methoxy)acetate (0.365 g, 0.719 mmol) in dioxane (3.60 mL) was added 4 N HCl (2.88 mL, 11.51 mmol). The reaction was stirred overnight and concentrated under reduced pressure to give the title compound (0.299 g) as a yellow oil. LCMS m/z=453.2 [M+H]+; $^1$H NMR (400 M Hz, DMSO-$d_6$) δ ppm 1.34-1.55 (m, 6H), 1.69-1.80 (m, 2H), 2.18 (bs, 1H), 3.23-3.28 (m, 1H), 3.40 (d, J=6.82 Hz, 2H), 3.98 (s, 2H), 4.11 (d, J=7.33 Hz, 2H), 7.13-7.22 (m, 2H), 7.25-7.32 (m, 3H), 7.32-7.35 (m, 1H), 7.35-7.44 (m, 3H), 12.52 (s, 1H).

Example 1.14

Preparation of 2-(((1s,4s)-4-((3-Oxo-5-m-tolyl-6-p-tolyl-1,2,4-triazin-2(3H)-yl)methyl)cyclohexyl)methoxy)acetic Acid (Compound 80)

Step A: Preparation of Ethyl 3-Oxo-2-m-tolyl-3-p-tolylpropanoate

To a cooled (−78° C.) solution of ethyl 2-m-tolylacetate (1.697 g, 9.52 mmol) in THF (10.58 mL) was added LiHMDS (9.52 mL, 9.52 mmol). The reaction was stirred for 15 minutes and 4-methylbenzoyl chloride (1.546 g, 10 mmol) in THF (21.16 mL) was slowly added. The reaction was allowed to warm to room temperature over 2 h. The reaction was quenched with AcOH, diluted with water and extracted with EtOAc three times. The combined extracts were washed with brine, dried ($MgSO_4$) and concentrated. The residue was purified by silica gel column chromatography to give the title compound as a yellow oil (2.213 g). $^1$H NMR (400 M Hz, $CDCl_3$) δ ppm 1.24 (t, J=7.07 Hz, 3H), 2.33 (s, 3H), 2.37 (s, 3H), 4.15-4.28 (m, 2H), 5.54 (s, 1H), 7.10 (d, J=7.07 Hz, 1H), 7.16-7.25 (m, 5H), 7.85 (d, J=8.08 Hz, 2H).

Step B: Preparation of 2-m-Tolyl-1-p-tolylethanone

To ethyl 3-oxo-2-m-tolyl-3-p-tolylpropanoate (2.213 g, 7.47 mmol) was added aqueous HCl solution (8.96 mL, 112 mmol). The reaction was heated to reflux overnight. The reaction was cooled to room temperature, the mixture was diluted with water and extracted with EtOAc three times. The combined extracts were washed with brine, dried (MgSO$_4$) and concentrated. The residue was purified by silica gel column chromatography to give the title compound as a white solid (1.174 g). $^1$H NMR (400 M Hz, CDCl$_3$) δ ppm 2.31-2.32 (m, 3H), 2.40 (s, 3H), 4.21 (s, 2H), 7.00-7.09 (m, 3H), 7.20 (t, J=7.45 Hz, 1H), 7.22-7.27 (m, 2H), 7.91 (d, J=8.34 Hz, 2H).

Step C: Preparation of 2-(Hydroxyimino)-2-m-tolyl-1-p-tolylethanone

From 2-m-tolyl-1-p-tolylethanone, the title compound was prepared using a similar method to the one described in Example 1.1, Step A to give a yellow oil. $^1$H NMR (400 M Hz, DMSO-d$_6$) δ ppm 2.32 (s, 3H), 2.39 (s, 3H), 7.20-7.26 (m, 1H), 7.26-7.31 (m, 3H), 7.33-7.37 (m, 2H), 7.84 (d, J=8.08 Hz, 2H), 12.28 (s, 1H).

Step D: Preparation of 3-(Methylthio)-5-m-tolyl-6-p-tolyl-1,2,4-triazine

From 2-(hydroxyimino)-2-m-tolyl-1-p-tolylethanone, the title compound was prepared using a similar method to the one described in Example 1.1, Step B to give a yellow solid. $^1$H NMR (400 M Hz, DMSO-d$_6$) δ ppm 2.27 (s, 3H), 2.33 (s, 3H), 2.71 (s, 3H), 7.15-7.23 (m, 4H), 7.23-7.31 (m, 1H), 7.33-7.37 (m, 2H), 7.38-7.44 (m, 1H).

Step E: Preparation of 3-(Methylsulfonyl)-5-m-tolyl-6-p-tolyl-1,2,4-triazine

From 3-(methylthio)-5-m-tolyl-6-p-tolyl-1,2,4-triazine, the title compound was prepared using a similar method to the one described in Example 1.1, Step C to give a yellow solid. $^1$H NMR (400 M Hz, DMSO-d$_6$) δ ppm 2.30 (s, 3H), 2.36 (s, 3H), 3.58 (s, 3H), 7.22-7.31 (m, 4H), 7.34 (t, J=7.45 Hz, 1H), 7.47 (d, J=8.08 Hz, 2H), 7.48-7.53 (m, 1H).

Step F: Preparation of 5-m-Tolyl-6-p-tolyl-1,2,4-triazin-3(2H)-one

From 3-(methylsulfonyl)-5-m-tolyl-6-p-tolyl-1,2,4-triazine, the title compound was prepared using a similar method to the one described in Example 1.1, Step D to give a yellow solid. $^1$H NMR (400 M Hz, DMSO-d$_6$) δ ppm 2.26 (s, 3H), 2.30 (s, 3H), 7.04 (d, J=7.83 Hz, 1H), 7.14 (s, 3H), 7.15-7.22 (m, 2H), 7.25-7.31 (m, 2H), 13.45 (s, 1H).

Step G: Preparation of tert-Butyl 2-(((1s,4s)-4-((3-Oxo-5-m-tolyl-6-p-tolyl-1,2,4-triazin-2(3H)-yl)methyl)cyclohexyl)methoxy)acetate From 5-m-tolyl-6-p-tolyl-1,2,4-triazin-3(2H)-one and tert-butyl 2-(((1s,4s)-4-(tosyloxymethyl)cyclohexyl)methoxy)acetate, the title compound was prepared using a similar method to the one described in Example 1.13, Step E to give a yellow solid. $^1$H NMR (400 M Hz, CDCl$_3$) δ ppm 1.44-1.52 (m, 2H), 1.48 (s, 9H), 1.52-1.65 (m, 6H), 1.76-1.92 (m, J=3.28 Hz, 2H), 2.30 (s, 3H), 2.36 (s, 3H), 3.45 (d, J=7.07 Hz, 2H), 3.95 (s, 2H), 4.21 (d, J=7.58 Hz, 2H), 7.04-7.20 (m, 6H), 7.23 (dd, J=6.82, 2.53 Hz, 1H), 7.47 (s, 1H).

Step H: Preparation of 2-(((1s,4s)-4-((3-Oxo-6-phenyl-5-m-fluoro-1,2,4-triazin-2(3H)-yl)methyl)cyclohexyl)methoxy)acetic Acid From tert-butyl 2-(((1s,4s)-4-((3-oxo-5-m-tolyl-6-p-tolyl-1,2,4-triazin-2(3H)-yl)methyl)cyclohexyl)methoxy)acetate, the title compound was prepared using a similar method to the one described in Example 1.13, Step F to give a yellow solid. LCMS m/z=462.5 [M+H]$^+$; $^1$H NMR (400 M Hz, DMSO-d$_6$) δ ppm 1.31-1.54 (m, 8H), 1.74 (bs, 1H), 2.17 (bs, 1H), 2.26 (s, 3H), 2.30 (s, 3H), 3.39 (d, J=6.82 Hz, 2H), 3.98 (s, 2H), 4.09 (d, J=7.58 Hz, 2H), 7.06 (d, J=7.58 Hz, 1H), 7.13-7.16 (m, 3H), 7.16-7.21 (m, 2H), 7.27 (d, J=7.33 Hz, 1H), 7.29-7.35 (m, 1H).

Example 1.15

Preparation of 2-(((1r,4r)-4-((3-Oxo-6-phenyl-5-m-tolyl-1,2,4-triazin-2(3H)-yl)methyl)cyclohexyl)methoxy)acetic Acid (Compound 81)

Step A: Preparation of tert-Butyl 2-(((1r,4r)-4-((3-Oxo-6-phenyl-5-m-tolyl-1,2,4-triazin-2(3H)-yl)methyl)cyclohexyl)methoxy)acetate From 6-phenyl-5-m-tolyl-1,2,4-triazin-3(2H)-one and tert-butyl 2-(((1r,4r)-4-(tosyloxymethyl)cyclohexyl)methoxy)acetate, the title compound was prepared using a similar method to the one described in Example 1.13, Step E to give a yellow oil. $^1$H NMR (400 M Hz, DMSO-d$_6$) δ ppm 0.86-1.01 (m, 2H), 1.01-1.13 (m, 2H), 1.41 (s, 9H), 1.46-1.59 (m, 1H), 1.75 (d, J=10.48 Hz, 4H), 1.87-1.96 (m, J=3.54 Hz, 1H), 2.24 (s, 3H), 3.25 (d, J=6.32 Hz, 2H), 3.91 (s, 2H), 3.99 (d, J=7.20 Hz, 2H), 7.08 (d, J=7.58 Hz, 1H), 7.19 (t, J=7.96 Hz, 1H), 7.24-7.30 (m, 4H), 7.31-7.42 (m, 3H).

Step B: Preparation of 2-(((1r,4r)-4-((3-Oxo-6-phenyl-5-m-tolyl-1,2,4-triazin-2(3H)-yl)methyl)cyclohexyl)methoxy)acetic Acid From tert-butyl 2-(((1r,4r)-4-((3-oxo-6-phenyl-5-m-tolyl-1,2,4-triazin-2(3H)-yl)methyl)cyclohexyl)methoxy)acetate, the title compound was prepared using a similar method to the one described in Example 1.13, Step F to give a yellow solid. LCMS m/z=448.5 [M+H]$^+$; $^1$H NMR (400 M Hz, DMSO-d$_6$) δ ppm 0.84-0.99 (m, 2H), 1.01-1.15 (m, 2H), 1.45-1.59 (m, J=8.34, 3.28 Hz, 1H), 1.71-1.80 (m, 4H), 1.85-2.00 (m, J=8.08, 4.55 Hz, 1H), 2.24 (s, 3H), 3.26 (d, J=6.32 Hz, 2H), 3.95 (s, 2H), 3.99 (d, J=7.07 Hz, 2H), 7.09 (d, J=7.83 Hz, 1H), 7.16-7.22 (m, 1H), 7.24-7.30 (m, 4H), 7.31-7.43 (m, 3H), 12.48 (bs, 1H).

Example 1.16

Preparation of 2-(((1r,4r)-4-((5-(3-Fluorophenyl)-3-oxo-6-phenyl-1,2,4-triazin-2(3H)-yl)methyl)cyclohexyl)methoxy)acetic Acid (Compound 82)

Step A: Preparation of tert-Butyl 2-(((1r,4r)-4-((5-(3-Fluorophenyl)-3-oxo-6-phenyl-1,2,4-triazin-2(3H)-yl)methyl)cyclohexyl)methoxy)acetate From 5-(3-fluorophenyl)-6-phenyl-1,2,4-triazin-3(2H)-one and tert-butyl 2-(((1r,4r)-4-(tosyloxymethyl)cyclohexyl)methoxy)acetate, the title compound was prepared using a similar method to the one described in Example 1.13, Step E to give an white solid. $^1$H NMR (400 M Hz, DMSO-d$_6$) δ ppm 0.93 (q, J=12.00 Hz, 2H), 1.02-1.14 (m, 2H), 1.41 (s, 9H), 1.46-1.59 (m, 1H), 1.76 (d, J=10.99 Hz, 4H), 1.86-1.98 (m, 1H), 3.25 (d, J=6.19 Hz, 2H), 3.91 (s, 2H), 4.00 (d, J=7.07 Hz, 2H), 7.14-7.22 (m, 2H), 7.27-7.30 (m, 2H), 7.30-7.35 (m, 1H), 7.34-7.43 (m, 4H).

Step B: Preparation of 2-(((1r,4r))-4-((3-Oxo-6-phenyl-5-m-tolyl-1,2,4-triazin-2(3H)-yl)methyl)cyclohexyl)methoxy)acetic acid From tert-butyl 2-(((1r,4r)-4-((5-(3-fluorophenyl)-3-oxo-6-phenyl-1,2,4-triazin-2(3H)-yl)methyl)cyclohexyl)methoxy)acetate, the title compound was prepared using a similar method to the one described in Example 1.13, Step F to give a yellow solid. LCMS m/z=452.4 [M+H]$^+$; $^1$H NMR (400 M Hz, DMSO-d$_6$) δ ppm 0.84-1.00 (m, 2H), 1.02-1.15 (m, 2H), 1.41-1.59 (m, 1H), 1.71-1.82 (m, 4H), 1.86-2.00 (m, J=6.32 Hz, 1H), 3.26 (d, J=6.32 Hz, 2H), 3.95 (s, 2H), 4.00 (d, J=7.07 Hz, 2H), 7.14-7.23 (m, 2H), 7.25-7.31 (m, 3H), 7.32-7.44 (m, 4H), 12.50 (bs, 1H).

Example 1.17

Preparation of 2-(((1r,4r)-4-((3-Oxo-5-m-tolyl-6-p-tolyl-1,2,4-triazin-2(3H)-yl)methyl)cyclohexyl)methoxy)acetic Acid (Compound 83)

Step A: Preparation of tert-Butyl 2-(((1r,4r)-4-((3-Oxo-5-m-tolyl-6-p-tolyl-1,2,4-triazin-2(3H)-yl)methyl)cyclohexyl)methoxy)acetate From 5-m-tolyl-6-p-tolyl-1,2,4-triazin-3(2H)-one and tert-butyl 2-(((1r,4r)-4-(tosyloxymethyl)cyclohexyl)methoxy)acetate, the title compound was prepared using a similar method to the one described in Example 1.13, Step E to give a yellow solid. $^1$H NMR (400 M Hz, CDCl$_3$) δ ppm 0.93-1.06 (m, 2H), 1.09-1.22 (m, 2H), 1.47 (s, 9H), 1.56-1.69 (m, 1H), 1.74-1.92 (m, J=28.04, 10.61 Hz, 4H), 2.03-2.12 (m, 1H), 2.30 (s, 3H), 2.36 (s, 3H), 3.32 (d, J=6.32 Hz, 2H), 3.92 (s, 2H), 4.10 (d, J=7.07 Hz, 2H), 7.06-7.12 (m, 1H), 7.11-7.17 (m, 3H), 7.17-7.24 (m, 2H), 7.40 (d, J=8.34 Hz, 1H), 7.48 (s, 1H).

Step B: Preparation of 2-(((1r,4r)-4-((3-Oxo-6-phenyl-5-m-tolyl-1,2,4-triazin-2(3H)-yl)methyl)cyclohexyl)methoxy)acetic Acid From tert-butyl 2-(((1r,4r)-4-((3-oxo-5-m-tolyl-6-p-tolyl-1,2,4-triazin-2(3H)-yl)methyl)cyclohexyl)methoxy)acetate, the title compound was prepared using a similar method to the one described in Example 1.13, Step F to give a yellow solid. LCMS m/z=462.4 [M+H]$^+$; NMR (400 M Hz, DMSO-d$_6$) δ ppm 0.84-1.00 (m, 2H), 1.01-1.14 (m, 2H), 1.46-1.58 (m, 1H), 1.70-1.80 (m, 4H), 1.85-1.98 (m, 1H), 2.26 (s, 3H), 2.30 (s, 3H), 3.25 (d, J=6.32 Hz, 2H), 3.95 (s, 2H), 3.98 (d, J=7.07 Hz, 2H), 7.07 (d, J=7.83 Hz, 1H), 7.12-7.18 (m, 4H), 7.18-7.22 (m, 1H), 7.24-7.29 (m, 1H), 7.30-7.33 (m, 1H).

Example 1.18

Preparation of 2-(((1s,4s)-4-((3-Oxo-6-phenyl-5-(thiophen-2-yl)-1,2,4-triazin-2(3H)-yl)methyl)cyclohexyl)methoxy)acetic Acid (Compound 84)

Step A: Preparation of Ethyl 3-Oxo-3-phenyl-2-(thiophen-2-yl)propanoate

From benzoyl chloride and ethyl 2-(thiophene-2-yl)acetate, the title compound was prepared using a similar method to the one described in Example 1.14, Step A to give a clear oil. $^1$H NMR (400 M Hz, CDCl$_3$) δ ppm 1.22 (t, J=7.07 Hz, 3H), 4.16-4.26 (m, 2H), 5.88 (s, 1H), 6.96-7.02 (m, 1H), 7.07 (d, J=3.03 Hz, 1H), 7.31 (dd, J=5.18, 1.14 Hz, 1H), 7.46 (t, J=7.71 Hz, 2H), 7.57 (t, J=7.33 Hz, 1H), 7.98-8.02 (m, 2H).

Step B: Preparation of 1-Phenyl-2-(thiophen-2-yl)ethanone

From ethyl 3-oxo-3-phenyl-2-(thiophen-2-yl)propanoate, the title compound was prepared using a similar method to the one described in Example 1.14, Step B to give a yellow solid. $^1$H NMR (400 M Hz, CDCl$_3$) δ ppm 4.48 (s, 2H), 6.91-6.95 (m, 1H), 6.95-6.99 (m, 1H), 7.22 (d, J=5.05 Hz, 1H), 7.47 (t, J=7.71 Hz, 2H), 7.52-7.60 (m, 1H), 8.02 (d, J=8.34 Hz, 2H).

Step C: Preparation of 2-(Hydroxyimino)-1-phenyl-2-(thiophen-2-yl)ethanone

From 1-phenyl-2-(thiophen-2-yl)ethanone, the title compound was prepared using a similar method to the one described in Example 1.1, Step A to give a yellow solid. $^1$H NMR (400 M Hz, DMSO-d$_6$) δ ppm 7.17 (dd, J=5.18, 3.92 Hz, 1H), 7.51-7.58 (m, 3H), 7.64-7.71 (m, 1H), 7.86 (dd, J=5.18, 1.14 Hz, 1H), 7.88-7.92 (m, 2H), 13.00 (s, 1H).

Step D: Preparation of 2-(Hydroxyimino)-1-phenyl-2-(thiophen-2-yl)ethanone

From 2-(hydroxyimino)-1-phenyl-2-(thiophen-2-yl)ethanone, the title compound was prepared using a similar method to the one described in Example 1.1, Step B to give a yellow solid. $^1$H NMR (400 M Hz, DMSO-d$_6$) δ ppm 2.70 (s, 3H), 6.91 (dd, J=3.92, 1.14 Hz, 1H), 7.04 (dd, J=5.05, 3.79 Hz, 1H), 7.52-7.64 (m, 5H), 7.90 (dd, J=4.93, 1.14 Hz, 1H).

Step E: Preparation of 3-(Methylsulfonyl)-6-phenyl-5-(thiophen-2-yl)-1,2,4-triazine From 2-(hydroxyimino)-1-phenyl-2-(thiophen-2-yl)ethanone, the title compound was prepared using a similar method to the one described in Example 1.1, Step C to give a yellow solid. $^1$H NMR (400 M Hz, DMSO-d$_6$) δ ppm 3.58 (s, 3H), 7.07-7.15 (m, 2H), 7.56-7.77 (m, 5H), 8.02 (dd, J=4.74, 1.33 Hz, 1H).

Step F: Preparation of 6-Phenyl-5-(thiophen-2-yl)-1,2,4-triazin-3(2H)-one

From 3-(methylsulfonyl)-6-phenyl-5-(thiophen-2-yl)-1,2,4-triazine, the title compound was prepared using a similar method to the one described in Example 1.1, Step D to give a yellow solid. $^1$H NMR (400 M Hz, DMSO-d$_6$) δ ppm 6.67 (dd, J=4.04, 1.01 Hz, 1H), 7.00 (dd, J=5.05, 4.04 Hz, 1H), 7.47-7.59 (m, 5H), 7.91 (dd, J=5.05, 1.01 Hz, 1H), 13.32 (s, 1H).

Step G: Preparation of tert-Butyl 2-(((1s,4s)-4-((3-Oxo-6-phenyl-5-(thiophen-2-yl)-1,2,4-triazin-2(3H)-yl)methyl)cyclohexyl)methoxy)acetate From 6-phenyl-5-(thiophen-2-yl)-1,2,4-triazin-3(2H)-one and tert-butyl 2-(((1s,4s)-4-(tosyloxymethyl)cyclohexyl)methoxy)acetate, the title compound was prepared using a similar method to the one described in Example 1.13, Step E to give a yellow solid. $^1$H NMR (400 M Hz, CDCl$_3$) δ ppm 1.41-1.46 (m, 4H), 1.48 (s, 9H), 1.49-1.54 (m, 2H), 1.56-1.62 (m, 2H), 1.81-1.93 (m, J=6.57, 3.79 Hz, 1H), 2.25-2.33 (m, J=6.44, 3.41 Hz, 1H), 3.43 (d, J=6.82 Hz, 2H), 3.94 (s, 2H), 4.17 (d, J=7.58 Hz, 2H), 6.87-6.90 (m, 1H), 6.91-6.94 (m, 1H), 7.41-7.49 (m, 4H), 7.50-7.54 (m, 1H), 7.56 (dd, J=5.05, 1.01 Hz, 1H).

Step H: Preparation of tert-Butyl 2-(((1s,4s)-4-((3-Oxo-6-phenyl-5-(thiophen-2-yl)-1,2,4-triazin-2(3H)-yl)methyl)cyclohexyl)methoxy)acetic Acid From tert-butyl 2-(((1s,4s)-4-((3-oxo-6-phenyl-5-(thiophen-2-yl)-1,2,4-triazin-2(3H)-yl)methyl)cyclohexyl)methoxy)acetate, the title compound was prepared using a similar method to the one described in Example 1.13, Step F to give a yellow solid. LCMS m/z=440.5 [M+H]$^+$; $^1$H NMR (400 M Hz, DMSO-d$_6$) δ ppm 1.33-1.52 (m, 8H), 1.67-1.78 (m, J=10.11, 10.11 Hz, 1H), 2.07-2.18 (m, J=3.03 Hz, 1H), 3.37 (d, J=7.07 Hz, 2H), 3.97 (s, 2H), 4.04 (d, J=7.58 Hz, 2H), 6.69 (dd, J=3.79, 1.01 Hz, 1H), 7.00 (dd, J=5.05, 3.79 Hz, 1H), 7.50-7.60 (m, 5H), 7.91 (dd, J=5.05, 1.01 Hz, 1H).

Example 1.19

Preparation of 2-(((1s,4s)-4-((4-(3-Chloro-2-fluorophenyl)-6-oxo-3-phenylpyridazin-1(6H)-yl)methyl)cyclohexyl)methoxy)acetic Acid (Compound 31)

Step A: Preparation of tert-Butyl 2-(((1s,4s)-4-((4-Bromo-6-oxo-3-phenylpyridazin-1(6H)-yl)methyl)cyclohexyl)methoxy)acetate To a solution of 5-bromo-6-phenylpyridazin-3(2H)-one (1.522 g, 6.06 mmol) in DMF (90 mL) was added tert-butyl 2-(((1s,4s)-4-(tosyloxymethyl)cyclohexyl)methoxy)acetate (2.50 g, 6.06 mmol), potassium 2-methylpropan-2-olate (1.360 g, 12.12 mmol) and 18-crown-6 (0.320 g, 1.212 mmol). The reaction was stirred at 40° C. for 16 h, quenched with water (40 mL), extracted with EtOAc (4×50 mL), and washed with brine. The combined organic phases were dried over MgSO$_4$, filtered, and concentrated to give a brown oil. The brown oil was purified by silica gel column chromatography to give the title compound as a yellow oil (1.346 g). LCMS m/z=491.3 [M+H]$^+$; $^1$H NMR (400 M Hz, CDCl$_3$) δ ppm, 1.37-1.64 (m, 17H), 1.80-1.90 (m, 1H), 2.23 (bs, 1H), 3.42 (d, J=7.07 Hz, 2H), 3.94 (s, 2H), 4.17 (d, J=7.71 Hz, 2H), 7.44-7.49 (m, 4H), 7.50-7.55 (m, 2H).

Step B: Preparation of tert-Butyl 2-(((1s,4s)-4-((4-(3-Chloro-2-fluorophenyl)-6-oxo-3-phenylpyridazin-1(6H)-yl)methyl)cyclohexyl)methoxy)acetate A vial was charged with 3-chloro-2-fluorophenylboronic acid (10.64 mg, 0.061 mmol), tert-butyl 2-(((1s,4s)-4-((4-bromo-6-oxo-3-phenylpyridazin-1(6H)-yl)methyl)cyclohexyl)methoxy)acetate (30.0 mg, 0.061 mmol), aqueous Na$_2$CO$_3$ (2 M, 0.061 mL, 0.122 mmol), and Pd(PPh$_3$)$_4$ (2.12 mg, 0.002 mmol) in a mixture of EtOH (1 mL) and benzene (3 mL). The reaction was heated under microwave irradiation at 130° C. for 1 h. The reaction mixture was diluted with water and the organic phase was removed. The aqueous layer was extracted with EtOAc three times. The combined organic phases were dried over MgSO$_4$, filtered and concentrated to give a white solid. This white solid was purified by silica gel column chromatography to give the title compound as a clear oil (0.033 g). LCMS m/z=541.3 [M+H]$^+$.

Step C: Preparation of 2-(((1s,4s)-4-((4-(3-Chloro-2-fluorophenyl)-6-oxo-3-phenylpyridazin-1(6H)-yl)methyl)cyclohexyl)methoxy)acetic Acid To a solution of tert-butyl 2-(((1s,4s)-4-((4-(3-chloro-2-fluorophenyl)-6-oxo-3-phenylpyridazin-1(6H)-yl)methyl)cyclohexyl)methoxy)acetate (0.033 g, 0.061 mmol) in DCM (2 mL) was added 4 M HCl in dioxane (0.152 mL, 0.610 mmol). The reaction was stirred at 25° C. for 16 h and concentrated to give a yellow oil. The yellow oil was purified by HPLC to give the title compound as a clear oil (0.012 g). LCMS m/z=485.5 [M+H]$^+$; $^1$H NMR (400 M Hz, CDCl$_3$) δ ppm 1.43-1.65 (m, 8H), 1.78-1.94 (m, 1H), 2.34 (bs, 1H), 3.52 (d, J=7.07 Hz, 2H), 4.11 (s, 2H), 4.28 (d, J=7.71 Hz, 2H), 7.03-7.12 (m, 3H), 7.14-7.19 (m, 2H), 7.23-7.29 (m, 2H), 7.29-7.35 (m, 1H), 7.37-7.45 (m, 1H).

Example 1.20

Preparation of 2-(((1s,4s)-4-((4-(5-Methylthiophen-2-yl)-6-oxo-3-phenylpyridazin-1(6H)-yl)methyl)cyclohexyl)methoxy)acetic Acid (Compound 45)

Step A: Preparation of tert-Butyl 2-(((1s,4s)-4-((4-(5-Methylthiophen-2-yl)-6-oxo-3-phenylpyridazin-1(6H)-yl)methyl)cyclohexyl)methoxy)acetate From 5-methylthiophen-2-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=509.5 [M+H]$^+$.

Step B: Preparation of 2-(((1s,4s)-4-((4-(5-Methylthiophen-2-yl)-6-oxo-3-phenylpyridazin-1(6H)-yl)methyl)cyclohexyl)methoxy)acetic Acid From tert-butyl 2-(((1s,4s)-4-((4-(5-methylthiophen-2-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=453.3 [M+H]$^+$; $^1$H NMR (400 M Hz, CDCl$_3$) δ ppm 1.39-1.62 (m, 8H), 1.73-1.91 (m, 1H), 2.28 (bs, 1H), 2.43 (s, 3H), 3.50 (d, J=6.95 Hz, 2H), 4.11 (s, 2H), 4.22 (d, J=7.71 Hz, 2H), 6.54-6.59 (m, 2H), 7.16-7.21 (m, 1H), 7.29-7.48 (m, 5H).

Example 1.21

Preparation of 2-(((1s,4s)-4-((4-(4-Methylthiophen-2-yl)-6-oxo-3-phenylpyridazin-1(6H)-yl)methyl)cyclohexyl)methoxy)acetic Acid (Compound 50)

Step A: Preparation of tert-Butyl 2-(((1s,4s)-4-((4-(4-Methylthiophen-2-yl)-6-oxo-3-phenylpyridazin-1(6H)-yl)methyl)cyclohexyl)methoxy)acetate From 4-methylthiophen-2-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=509.4 [M+H]$^+$.

Step B: Preparation of 2-(((1s,4s)-4-((4-(4-Methylthiophen-2-yl)-6-oxo-3-phenylpyridazin-1(6H)-yl)methyl)cyclohexyl)methoxy)acetic Acid From tert-butyl 2-(((1s,4s)-4-((4-(4-methylthiophen-2-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=453.2 [M+H]$^+$.

Example 1.22

Preparation of 2-(((1s,4s)-4-((4-(2-Methylpyridin-4-yl)-6-oxo-3-phenylpyridazin-1(6H)-yl)methyl)cyclohexyl)methoxy)acetic Acid (Compound 51)

Step A: Preparation of tert-Butyl 2-(((1s,4s)-4-((4-(2-Methylpyridin-4-yl)-6-oxo-3-phenylpyridazin-1(6H)-yl)methyl)cyclohexyl)methoxy)acetate From 2-methylpyridin-4-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=504.4 [M+H]$^+$.

Step B: Preparation of 2-(((1s,4s)-4-((4-(2-Methylpyridin-4-yl)-6-oxo-3-phenylpyridazin-1(6H)-yl)methyl)cyclohexyl)methoxy)acetic Acid From tert-butyl 2-(((1s,4s)-4-((4-(2-methylpyridin-4-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=448.4 [M+H]$^+$.

Example 1.23

Preparation of 2-(((1s,4s)-4-((4-(2,3-Difluorophenyl)-6-oxo-3-phenylpyridazin-1(6H)-yl)methyl)cyclohexyl)methoxy)acetic Acid (Compound 8)

Step A: Preparation of tert-Butyl 2-(((1s,4s)-4-((4-(2,3-Difluorophenyl)-6-oxo-3-phenylpyridazin-1(6H)-yl)methyl)cyclohexyl)methoxy)acetate From 2,3-difluorophenylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=525.7 [M+H]$^+$.

Step B: Preparation of 2-(((1s,4s)-4-((4-(2,3-Difluorophenyl)-6-oxo-3-phenylpyridazin-1(6H)-yl)methyl)cyclohexyl)methoxy)acetic Acid From tert-butyl 2-(((1s,4s)-4-((4-(2,3-difluorophenyl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=469.5 [M+H]$^+$; $^1$H NMR (400 MHz, CDCl$_3$) δ ppm 1.42-1.67 (m, 8H), 1.77-1.93 (m, 1H), 2.34 (bs, 1H), 3.52 (d, J=6.95 Hz, 2H), 4.13 (s, 2H), 4.31 (d, J=7.58 Hz, 2H), 6.92-7.01 (m, 1H), 7.07-7.14 (m, 1H), 7.14-7.30 (m, 6H), 7.30-7.37 (m, 1H).

Example 1.24

Preparation of 2-(((1s,4s)-4-((4-(2-Fluoropyridin-3-yl)-6-oxo-3-phenylpyridazin-1(6H)-yl)methyl)cyclohexyl)methoxy)acetic Acid (Compound 54)

Step A: Preparation of tert-Butyl 2-(((1s,4s)-4-((4-(2-Fluoropyridin-3-yl)-6-oxo-3-phenylpyridazin-1(6H)-yl)methyl)cyclohexyl)methoxy)acetate From 2-fluoropyridin-3-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=508.3 [M+H]$^+$.

Step B: Preparation of 2-(((1s,4s)-4-((4-(2-Fluoropyridin-3-yl)-6-oxo-3-phenylpyridazin-1(6H)-yl)methyl)cyclohexyl)methoxy)acetic Acid From tert-butyl 2-(((1s,4s)-4-((4-(2-fluoropyridin-3-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=452.3 [M+H]$^+$

Example 1.25

Preparation of 2-(((1s,4s)-4-((4-(6-Fluoropyridin-3-yl)-6-oxo-3-phenylpyridazin-1(6H)-yl)methyl)cyclohexyl)methoxy)acetic Acid (Compound 55)

Step A: Preparation of tert-Butyl 2-(((1s,4s)-4-((4-(6-Fluoropyridin-3-yl)-6-oxo-3-phenylpyridazin-1(6H)-yl)methyl)cyclohexyl)methoxy)acetate From 6-fluoropyridin-3-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=508.2 [M+H]$^+$.

Step B: Preparation of 2-(((1s,4s)-4-((4-(6-Fluoropyridin-3-yl)-6-oxo-3-phenylpyridazin-1(6H)-yl)methyl)cyclohexyl)methoxy)acetic Acid From tert-butyl 2-(((1s,4s)-4-((4-(6-fluoropyridin-3-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=452.3 [M+H]$^+$; $^1$H NMR (400 MHz, CDCl$_3$) δ ppm 1.42-1.67 (m, 8H), 1.77-1.93 (m, 1H), 2.33 (bs, 1H), 3.52 (d, J=6.95 Hz, 2H), 4.13 (s, 2H), 4.30 (d, J=7.58 Hz, 2H), 6.88 (dd, J=8.46, 2.78 Hz, 1H), 7.12-7.23 (m, 3H), 7.28-7.41 (m, 3H), 7.46-7.54 (m, 1H), 8.08 (d, J=2.40 Hz, 1H).

Example 1.26

Preparation of 2-(((1s,4s)-4-((4-(2-Chloropyridin-4-yl)-6-oxo-3-phenylpyridazin-1(6H)-yl)methyl)cyclohexyl)methoxy)acetic Acid (Compound 56)

Step A: Preparation of tert-Butyl 2-(((1s,4s)-4-((4-(2-Chloropyridin-4-yl)-6-oxo-3-phenylpyridazin-1(6H)-yl)methyl)cyclohexyl)methoxy)acetate From 2-chloropyridin-4-ylboronic acid and tert-butyl 2-(((1s,4s)-4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=524.7, 526.6 [M+H]⁺.

Step B: Preparation of 2-(((1s,4s)-4-((4-(2-Chloropyridin-4-yl)-6-oxo-3-phenylpyridazin-1(6H)-yl)methyl)cyclohexyl)methoxy)acetic Acid From tert-butyl 2-(((1s,4s)-4-((4-(2-chloropyridin-4-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=468.4, 470.5 [M+H]⁺.

Example 1.27

Preparation of 2-(((1s,4s)-4-((4-(2-Fluoropyridin-4-yl)-6-oxo-3-phenylpyridazin-1(6H)-yl)methyl)cyclohexyl)methoxy)acetic Acid (Compound 59)

Step A: Preparation of tert-Butyl 2-(((1s,4s)-4-((4-(2-Fluoropyridin-4-yl)-6-oxo-3-phenylpyridazin-1(6H)-yl)methyl)cyclohexyl)methoxy)acetate From 2-fluoropyridin-4-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=508.4 [M+H]⁺.

Step B: Preparation of 2-(((1s,4s)-4-((4-(2-Fluoropyridin-4-yl)-6-oxo-3-phenylpyridazin-1(6H)-yl)methyl)cyclohexyl)methoxy)acetic Acid From tert-butyl 2-(((1s,4s)-4-((4-(2-fluoropyridin-4-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=452.3 [M+H]⁺; ¹H NMR (400 M Hz, CDCl₃) δ ppm 1.42-1.65 (m, 8H), 1.76-1.94 (m, 1H), 2.32 (bs, 1H), 3.51 (d, J=6.95 Hz, 2H), 4.11 (s, 2H), 4.26 (d, J=7.58 Hz, 2H), 6.73 (s, 1H), 6.89-6.93 (m, 1H), 7.04 (s, 1H), 7.13-7.18 (m, 2H), 7.25-7.40 (m, 3H), 8.16 (d, J=5.05 Hz, 1H).

Example 1.28

Preparation of 2-(((1s,4s)-4-((4-(5-Methylpyridin-3-yl)-6-oxo-3-phenylpyridazin-1(6H)-yl)methyl)cyclohexyl)methoxy)acetic Acid (Compound 60)

Step A: Preparation of tert-Butyl 2-(((1s,4s)-4-((4-(5-Methylpyridin-3-yl)-6-oxo-3-phenylpyridazin-1(6H)-yl)methyl)cyclohexyl)methoxy)acetate From 5-methylpyridin-3-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=504.5 [M+H]⁺.

Step B: Preparation of 2-(((1s,4s)-4-((4-(5-Methylpyridin-3-yl)-6-oxo-3-phenylpyridazin-1(6H)-yl)methyl)cyclohexyl)methoxy)acetic Acid From tert-butyl 2-(((1s,4s)-4-((4-(5-methylpyridin-3-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=448.3 [M+H]⁺; ¹H NMR (400 M Hz, CDCl₃) δ ppm 1.42-1.65 (m, 8H), 1.78-1.94 (m, 1H), 2.29 (bs, 1H), 2.44 (bs, 3H), 3.51 (d, J=7.07 Hz, 2H), 4.10 (s, 2H), 4.30 (d, J=7.07 Hz, 2H), 7.10-7.17 (m, 3H), 7.29-7.42 (m, 3H), 7.73 (s, 1H), 8.43 (s, 1H), 8.60 (s, 1H).

Example 1.29

Preparation of 2-(((1s,4s)-4-((4-(5-Chloropyridin-3-yl)-6-oxo-3-phenylpyridazin-1(6H)-yl)methyl)cyclohexyl)methoxy)acetic Acid (Compound 66)

Step A: Preparation of tert-Butyl 2-(((1s,4s)-4-((4-(5-Chloropyridin-3-yl)-6-oxo-3-phenylpyridazin-1(6H)-yl)methyl)cyclohexyl)methoxy)acetate From 5-chloropyridin-3-ylboronic acid and tert-butyl 2-(((1s,4s)-4-((4-bromo-6-oxo-3-phenylpyridazin-1(6H)-yl)methyl)cyclohexyl)methoxy)acetate, the title compound was prepared using a similar method to the one described in Example 1.19, Step B, to give a white solid. LCMS m/z=524.7 [M+H]⁺.

Step B: Preparation of 2-(((1s,4s)-4-((4-(5-Chloropyridin-3-yl)-6-oxo-3-phenylpyridazin-1(6H)-yl)methyl)cyclohexyl)methoxy)acetic Acid From tert-butyl 2-(((1s,4s)-4-((4-(5-chloropyridin-3-yl)-6-oxo-3-phenylpyridazin-1(6H)-yl)methyl)cyclohexyl)methoxy)acetate, the title compound was prepared using a similar method to the one described in Example 1.19, Step C, to give a white solid. LCMS m/z=468.4 [M+H]⁺.

Example 1.30

Preparation of 2-(((1s,4s)-4-((3-oxo-6-phenyl-5-m-tolyl-1,2,4-triazin-2(3H)-yl)methyl)cyclohexyl)methoxy)acetic Acid (Compound 73)

Step A: Preparation of 2-(Hydroxyimino)-1-phenyl-2-m-tolylethanone

From 1-phenyl-2-m-tolylethanone, the title compound was prepared using a similar method to the one described in Example 1.1, Step A to give a yellow oil. ¹H NMR (400 M Hz, CDCl₃) ppm 2.28-2.40 (m, 3H), 3.49 (d, J=5.05 Hz, 1H), 7.19-7.27 (m, 1H), 7.30-7.36 (m, 1H), 7.37-7.42 (m, 1H), 7.44-7.53 (m, 2H), 7.55-7.65 (m, 1H), 7.94-7.99 (m, 1H), 8.00-8.03 (m, 1H), 8.06 (s, 1H).

Step B: Preparation of 3-(Methylthio)-6-phenyl-5-m-tolyl-1,2,4-triazine

From 2-(hydroxyimino)-1-phenyl-2-m-tolylethanone, the title compound was prepared using a similar method to the one described in Example 1.1, Step B to give a yellow solid. ¹H NMR (400 M Hz, DMSO-d₆) δ ppm 2.25 (s, 3H), 2.72 (s, 3H), 7.15-7.31 (m, 3H), 7.35-7.52 (m, 6H).

Step C: Preparation of 3-(Methylsulfonyl)-6-phenyl-5-m-tolyl-1,2,4-triazine

From 3-(methylthio)-6-phenyl-5-m-tolyl-1,2,4-triazine, the title compound was prepared using a similar method to the one described in Example 1.1, Step C as a yellow solid. ¹H NMR (400 MHz, DMSO-d$_6$) δ ppm 2.28 (s, 3H), 3.60 (s, 3H), 7.24-7.28 (m, 2H), 7.32-7.38 (m, 1H), 7.44-7.49 (m, 2H), 7.50-7.61 (m, 3H), 7.86-7.91 (m, 1H).

Step D: Preparation of
6-Phenyl-5-m-tolyl-1,2,4-triazin-3(2H)-one

From 3-(methylsulfonyl)-6-phenyl-5-m-tolyl-1,2,4-triazine, the title compound was prepared using a similar method to the one described in Example 1.1, Step D as a yellow solid. $^1$H NMR (400 M Hz, DMSO-d$_6$) δ ppm 2.24 (s, 3H), 7.06 (d, J=7.83 Hz, 1H), 7.18 (t, J=7.83 Hz, 1H), 7.23-7.30 (m, 4H), 7.30-7.41 (m, 3H), 13.52 (s, 1H).

Step E: Preparation of 2-(((1s,4s)-4-((3-oxo-6-phenyl-5-m-tolyl-1,2,4-triazin-2(3H)-yl)methyl)cyclohexyl)methoxy)acetic Acid From tert-butyl 2-(((1s,4s)-4-(tosyloxymethyl)cyclohexyl)methoxy)acetate and 6-phenyl-5-m-tolyl-1,2,4-triazin-3(2H)-one, the title compound was prepared using a similar method to the one described in Example 1.1, Step E to give a yellow oil. LCMS m/z=448.5 [M+H]$^+$; $^1$H NMR (400 M Hz, DMSO-d$_6$) δ ppm 1.37-1.53 (m, 6H), 1.68-1.80 (m, 2H), 2.13-2.21 (m, J=3.79 Hz, 1H), 2.24 (s, 3H), 3.23-3.27 (m, 1H), 3.40 (d, J=7.07 Hz, 2H), 3.99 (s, 2H), 4.10 (d, J=7.58 Hz, 2H), 7.08 (d, J=7.58 Hz, 1H), 7.19 (t, J=7.83 Hz, 1H), 7.23-7.30 (m, 4H), 7.31-7.41 (m, 3H), 12.50 (s, 1H).

Example 1.31

Preparation of t-Butyl 2-(((1s,4s)-4-(Tosyloxymethyl)cyclohexyl)methoxy)acetate

Step A: Preparation of (1s,4s)-Diethyl Cyclohexane-1,4-dicarboxylate

To a solution of (1s,4s)-cyclohexane-1,4-dicarboxylic acid (25 g, 145 mmol) in ethanol (150 mL) was added concentrated H$_2$SO$_4$ (1 mL). The reaction was refluxed for 16 h, cooled to room temperature and concentrated. The residue was extracted with EtOAc and saturated NaHCO$_3$, washed with brine, dried over MgSO$_4$, and filtered. The filtrate was concentrated to provide the title compound as a colorless oil (30.5 g). $^1$H NMR (400 MHz, CDCl$_3$) δ ppm 1.25 (t, J=7.14 Hz, 6H), 1.64-1.70 (m, 4H), 1.87-1.92 (m, 4H), 2.44-2.46 (m, 2H), 4.11-1.46 (quartet, J=7.12 Hz, 4H).

Step B: Preparation of (1s,4s)-Cyclohexane-1,4-diyldimethanol

To a solution of (1s,4s)-diethyl cyclohexane-1,4-dicarboxylate (13.0 g, 56.9 mmol) in THF (500 mL) was added lithium aluminum hydride (4.54 g, 120 mmol) in portions at 0° C. The mixture was stirred at that temperature for 2 h and quenched with cold water, filtered and concentrated to give the title compound as a colorless oil (8.2 g). $^1$H NMR (400 MHz, DMSO-d$_6$) δ ppm 1.27-1.42 (m, 8H), 1.46-1.54 (m, 2H), 3.26-3.31 (m, 4H), 4.27-4.30 (t, J=5.31 Hz, 2H).

Step C: Preparation of tert-Butyl 2-(((1s,4s)-4-(Hydroxymethyl)cyclohexyl)methoxy)acetate To a solution of (1s,4s)-cyclohexane-1,4-diyldimethanol (18.2 g, 126 mmol) in toluene (200 mL) was added NaOH (50% aqueous, 60 mL) and tetrabutylammonium iodide (2.331 g, 6.31 mmol), followed by tert-butyl-2-bromoacetate (20.50 mL, 139 mmol) at room temperature. The reaction mixture was stirred vigorously at room temperature for 2 h and diluted with ethyl acetate and water. After separation, the aqueous layer was extracted with EtOAc (3×30 mL). The combined organic layers were dried over MgSO$_4$, concentrated, and purified by silica gel column chromatography to give the title compound as a colorless oil (13.5 g). $^1$H NMR (400 MHz, CDCl$_3$) δ ppm 1.35-1.47 (m, 4H), 1.48 (s, 9H), 1.50-1.60 (m, 4H), 1.63-1.74 (m, 1H), 1.79-1.92 (m, 1H), 3.42 (d, J=6.95 Hz, 2H), 3.55 (d, J=6.82 Hz, 2H), 3.93 (s, 1H), 3.94 (s, 2H).

Step D: Preparation of tert-Butyl 2-(((1s,4s)-4-(Tosyloxymethyl)cyclohexyl)methoxy)acetate To a solution of tert-butyl 2-(((1s,4s)-4-(hydroxymethyl)cyclohexyl)methoxy)acetate (12.0 g, 46.4 mmol) in dichloromethane (150 mL) were added triethylamine (4.70 g, 46.4 mmol) and 4-(dimethylamino)pyridine (0.567 g, 4.64 mmol), followed by 4-methylbenzene-1-sulfonyl chloride (8.86 g, 46.4 mmol). The reaction was stirred at room temperature for 16 h. The solvent was removed and the residue was extracted with EtOAc/H$_2$O. The organic extracts were dried over MgSO$_4$, and concentrated. The residue was purified by silica gel column chromatography to give the title compound as a pale liquid (9.5 g). LCMS m/z=413.1 [M+H]$^+$; $^1$H NMR (400 MHz, CDCl$_3$) δ ppm 1.28-1.43 (m, 4H), 1.46-1.48 (m, 9H), 1.49-1.56 (m, 4H), 1.76-1.91 (m, 2H), 2.45 (s, 3H), 3.36 (d, J=6.95 Hz, 2H), 3.92 (d, J=7.05 Hz, 2H), 3.92 (s, 2H), 7.35 (d, J=8.46 Hz, 2H), 7.78 (d, J=8.34 Hz, 2H).

Example 1.32

Preparation of tert-Butyl 2-(((1s,4s)-4-(Tosyloxymethyl)cyclohexyl)methoxy)acetate Step A: Preparation of (1s,4s)-Cyclohexane-1,4-diyldimethanol To a solution of (1s,4s)-cyclohexane-1,4-dicarboxylic acid (8.617 g, 50.0 mmol) in THF (50.0 mL) at 0° C. was added LAH (100 mL, 200 mmol) via cannula. The reaction mixture was stirred at 0° C. and allowed to warm to room temperature overnight. After 24 h, the reaction was quenched with H$_2$O (7.6 mL), 10% NaOH (15.2 mL), and followed by additional H$_2$O (22.8 mL). The precipitate formed was filtered and rinsed with EtOAc. The filtrate was washed with brine, dried over MgSO$_4$, and concentrated to give the title compound as a colorless oil (5.91 g).

Step B: Preparation of ((1s,4s)-4-(Hydroxymethyl)cyclohexyl)methyl 4-methylbenzenesulfonate To a solution of (1s,4s)-cyclohexane-1,4-diyldimethanol (5.91 g, 41.0 mmol) in CH$_2$Cl$_2$ (300 mL) was added 4-methylbenzene-1-sulfonyl chloride (7.80 g, 40.9 mmol) and triethylamine (7.75 mL, 55.6 mmol) followed by DMAP (0.246 g, 2.014 mmol). The resulting reaction mixture was stirred at room temperature overnight. Upon completion, the solvent was removed under reduced pressure and the residue was washed with H$_2$O and brine, dried over MgSO$_4$ and concentrated. The residue was purified by silica gel column chromatography to give the title compound as a colorless oil (5.30 g). LCMS m/z=299.4.

Step C: Preparation of tert-Butyl 2-(((1s,4s)-4-(Tosyloxymethyl)cyclohexyl)methoxy)acetate To a solution of ((1s,4s)-4-(hydroxymethyl)cyclohexyl) methyl 4-methylbenzenesulfonate (5.30 g, 17.76 mmol) in $CH_2Cl_2$ (100 mL) was added diacetoxyrhodium (472.4 mg, 1.069 mmol). The resulting reaction mixture was stirred at room temperature for 30 min then placed in an ice bath. To the reaction mixture at 0° C. was added dropwise a solution of tert-butyl 2-diazoacetate (4.0 g, 28.1 mmol) in $CH_2Cl_2$ (10.0 mL) over 1 h. The reaction mixture was stirred at 0° C. and slowly warmed to room temperature. After 48 h, the reaction mixture was filtered through Celite® which was rinsed with $CH_2Cl_2$ and the combined filtrate and rinsings were concentrated. The residue was purified by silica gel column chromatography to give the title compound as a colorless oil (5.659 g).

Example 1.33

Preparation of 2-(((1s,4s)-4-((6-Oxo-4-phenyl-3-(thiophen-3-yl)pyridazin-1(6H)-yl)methyl)cyclohexyl)methoxy)acetic Acid (Compound 61)

Step A: Preparation of tert-Butyl 2-(((1s,4s)-4-((3-Chloro-6-oxo-4-phenylpyridazin-1(6H)-yl)methyl)cyclohexyl)methoxy)acetate To a solution of 6-chloro-5-phenylpyridazin-3(2H)-one (0.480 g, 2.323 mmol), in DMF (34 mL) was added tert-butyl 2-(((1s,4s)-4-(tosyloxymethyl)cyclohexyl)methoxy)acetate (0.958 g, 2.323 mmol), potassium 2-methylpropan-2-olate (0.521 g, 4.650 mmol) and 18-crown-6 (0.123 g, 0.465 mmol). The resulting mixture was stirred at 40° C. for 16 h. The reaction mixture was quenched with water (20 mL), extracted with EtOAc (4×20 mL) and washed with brine. The combined organics were dried over $MgSO_4$, filtered, and concentrated to give a brown oil. This brown oil was purified by silica gel column chromatography to give the title compound as a yellow oil (1.346 g). LCMS m/z=447.5 [M+H]$^+$; $^1$H NMR (400 MHz, $CDCl_3$) δ ppm 1.38-1.66 (m, 17H), 1.82-1.93 (m, 1H), 2.24 (bs, 1H), 3.45 (d, J=7.07 Hz, 2H), 3.96 (s, 2H), 4.13 (d, J=7.71 Hz, 2H), 6.89 (s, 1H), 7.40-7.53 (m, 5H).

Step B: Preparation of tert-Butyl 2-(((1s,4s)-4-((6-oxo-4-phenyl-3-(thiophen-3-yl)pyridazin-1(6H)-yl)methyl)cyclohexyl)methoxy)acetate A vial was charged with thiophen-3-ylboronic acid (31.0 mg, 0.246 mmol), tert-butyl 2-(((1s,4s)-4-((3-chloro-6-oxo-4-phenylpyridazin-1(6H)-yl)methyl)cyclohexyl)methoxy) acetate (100 mg, 0.224 mmol), aqueous $Na_2CO_3$ (2 M solution, 0.224 mL, 0.447 mmol), and $Pd(PPh_3)_4$ (7.76 mg, 0.007 mmol) in a mixture of EtOH (1 mL) and benzene (3 mL). The reaction was heated in the under microwave irradiation at 130° C. for 1 h. The reaction mixture was diluted with water and the organic layer was removed. The aqueous layer was extracted three times with EtOAc. The combined organics were dried over $MgSO_4$, filtered and concentrated. The residue was purified by HPLC to give the title compound as a clear oil (0.037 g). LCMS m/z=495.4 [M+H]$^+$.

Step C: Preparation of 2-(((1s,4s)-4-((6-Oxo-4-phenyl-3-(thiophen-3-yl)pyridazin-1(6H)-yl)methyl)cyclohexyl)methoxy)acetic Acid To a solution of tert-butyl 2-(((1s,4s)-4-((6-oxo-4-phenyl-3-(thiophen-3-yl)pyridazin-1(6H)-yl)methyl)cyclohexyl) methoxy)acetate (0.037 g, 0.074 mmol) in DCM (2 mL) was added 4 M HCl in dioxane (0.186 mL, 0.744 mmol). The reaction mixture was stirred at 25° C. for 16H and evaporated down to give a yellow oil. This yellow oil was purified by HPLC to give the title compound as a white solid (0.025 g). LCMS m/z=439.2 [M+H]$^+$; $^1$H NMR (400 MHz, $CDCl_3$) δ ppm 1.42-1.67 (m, 8H), 1.76-1.93 (m, 1H), 2.32 (bs, 1H), 3.52 (d, J=6.95 Hz, 2H), 4.12 (s, 2H), 4.25 (d, J=7.58 Hz, 2H), 6.91-7.01 (m, 3H), 7.14-7.23 (m, 3H), 7.31-7.46 (m, 3H).

Example 1.34

Preparation of 2-(((1s,4s)-4-((6-Oxo-4-phenyl-3-(pyridin-4-yl)pyridazin-1(6H)-yl)methyl)cyclohexyl)methoxy)acetic Acid (Compound 57)

Step A: Preparation of tert-Butyl 2-(((1s,4s)-4-((6-oxo-4-phenyl-3-(pyridin-4-yl)pyridazin-1(6H)-yl)methyl)cyclohexyl)methoxy)acetate From pyridin-4-ylboronic acid and tert-butyl 2-(((1s,4s)-4-((3-chloro-6-oxo-4-phenylpyridazin-1(6H)-yl)methyl)cyclohexyl)methoxy)acetate, the title compound was prepared using a similar method to the one described in Example 1.33, Step B, to give a white solid. LCMS m/z=490.5 [M+H]$^+$.

Step B: Preparation of 2-(((1s,4s)-4-((6-Oxo-4-phenyl-3-(pyridin-4-yl)pyridazin-1(6H)-yl)methyl)cyclohexyl)methoxy)acetic Acid From tert-butyl 2-(((1s,4s)-4-((6-oxo-4-phenyl-3-(pyridin-4-yl)pyridazin-1(6H)-yl)methyl)cyclohexyl)methoxy) acetate, the title compound was prepared using a similar method to the one described in Example 1.33, Step C, to give a white solid. LCMS m/z=434.4 [M+H]$^+$.

Example 1.35

Preparation of 2-(((1s,4s)-4-((6-Oxo-4-phenyl-3-(pyridin-3-yl)pyridazin-1(6H)-yl)methyl)cyclohexyl)methoxy)acetic Acid (Compound 42)

Step A: Preparation of tert-Butyl 2-(((1s,4s)-4-((6-Oxo-4-phenyl-3-(pyridin-3-yl)pyridazin-1(6H)-yl)methyl)cyclohexyl)methoxy)acetate From pyridin-3-ylboronic acid and tert-butyl 2-(((1s,4s)-4-((3-chloro-6-oxo-4-phenylpyridazin-1(6H)-yl)methyl)cyclohexyl)methoxy)acetate, the title compound was prepared using a similar method to the one described in Example 1.33, Step B, to give a white solid. LCMS m/z=490.5 [M+H]$^+$.

Step B: Preparation of 2-(((1s,4s)-4-((6-Oxo-4-phenyl-3-(pyridin-3-yl)pyridazin-1(6H)-yl)methyl)cyclohexyl)methoxy)acetic Acid From tert-butyl 2-(((1s,4s)-4-((6-oxo-4-phenyl-3-(pyridin-3-yl)pyridazin-1(6H)-yl)methyl)cyclohexyl)methoxy) acetate, the title compound was prepared using a similar method to the one described in Example 1.33, Step C, to give a white solid. LCMS m/z=434.3 [M+H]⁺.

Example 1.36

Preparation of 2-(((1s,4s)-4-((6-Oxo-4-phenyl-3-(thiophen-2-yl)pyridazin-1(6H)-yl)methyl)cyclohexyl)methoxy)acetic Acid (Compound 58)

Step A: Preparation of tert-Butyl 2-(((1s,4s)-4-((6-Oxo-4-phenyl-3-(thiophen-2-yl)pyridazin-1(6H)-yl)methyl)cyclohexyl)methoxy)acetate From thiophen-2-ylboronic acid and tert-butyl 2-(((1s,4s)-4-((3-chloro-6-oxo-4-phenylpyridazin-1(6H)-yl)methyl)cyclohexyl)methoxy)acetate, the title compound was prepared using a similar method to the one described in Example 1.33, Step B, to give a white solid. LCMS m/z=495.5 [M+H]⁺.

Step B: Preparation of 2-(((1s,4s)-4-((6-Oxo-4-phenyl-3-(thiophen-2-yl)pyridazin-1(6H)-yl)methyl)cyclohexyl)methoxy)acetic Acid From tert-butyl 2-(((1s,4s)-4-((6-oxo-4-phenyl-3-(thiophen-2-yl)pyridazin-1(6H)-yl)methyl)cyclohexyl)methoxy)acetate, the title compound was prepared using a similar method to the one described in Example 1.33, Step B, to give a white solid. LCMS m/z=439.3 [M+H]⁺.

Example 1.37

Preparation of 2-(((1s,4s)-4-((3-(5-Methylpyridin-3-yl)-6-oxo-4-phenylpyridazin-1(6H)-yl)methyl)cyclohexyl)methoxy)acetic Acid (Compound 62)

Step A: Preparation of tert-Butyl 2-(((1s,4s)-4-((3-(5-Methylpyridin-3-yl)-6-oxo-4-phenylpyridazin-1(6H)-yl)methyl)cyclohexyl)methoxy)acetate From 5-methylpyridin-3-ylboronic acid and tert-butyl 2-(((1s,4s)-4-((3-chloro-6-oxo-4-phenylpyridazin-1(6H)-yl)methyl)cyclohexyl)methoxy)acetate, the title compound was prepared using a similar method to the one described in Example 1.33, Step B, to give a white solid. LCMS m/z=504.4 [M+H]⁺.

Step B: Preparation of 2-(((1s,4s)-4-((3-(5-Methylpyridin-3-yl)-6-oxo-4-phenylpyridazin-1(6H)-yl)methyl)cyclohexyl)methoxy)acetic Acid From tert-butyl 2-(((1s,4s)-4-((3-(5-methylpyridin-3-yl)-6-oxo-4-phenylpyridazin-1(6H)-yl)methyl)cyclohexyl)methoxy)acetate, the title compound was prepared using a similar method to the one described in Example 1.33, Step C, to give a white solid. LCMS m/z=448.5 [M+H]⁺.

Example 1.38

Preparation of 2-(((1s,4s)-4-((3-(6-Methylpyridin-3-yl)-6-oxo-4-phenylpyridazin-1(6H)-yl)methyl)cyclohexyl)methoxy)acetic Acid (Compound 63)

Step A: Preparation of tert-Butyl 2-(((1s,4s)-4-((3-(6-Methylpyridin-3-yl)-6-oxo-4-phenylpyridazin-1(6H)-yl)methyl)cyclohexyl)methoxy)acetate From 6-methylpyridin-3-ylboronic acid hydrate and tert-butyl 2-(((1s,4s)-4-((3-chloro-6-oxo-4-phenylpyridazin-1(6H)-yl)methyl)cyclohexyl)methoxy)acetate, the title compound was prepared using a similar method to the one described in Example 1.33, Step B, to give a white solid. LCMS m/z=504.4 [M+H]⁺.

Step B: Preparation of 2-(((1s,4s)-4-((3-(6-Methylpyridin-3-yl)-6-oxo-4-phenylpyridazin-1(6H)-yl)methyl)cyclohexyl)methoxy)acetic Acid From tert-butyl 2-(((1s,4s)-4-((3-(6-methylpyridin-3-yl)-6-oxo-4-phenylpyridazin-1(6H)-yl)methyl)cyclohexyl)methoxy)acetate, the title compound was prepared using a similar method to the one described in Example 1.33, Step C, to give a white solid. LCMS m/z=448.5 [M+H]⁺; NMR (400 MHz, CDCl₃) δ ppm 1.40-1.70 (m, 8H), 1.80-1.93 (m, 1H), 2.32 (bs, 1H), 2.82 (s, 3H), 3.51 (d, J=6.95 Hz, 2H), 4.10 (s, 2H), 4.29 (d, J=7.71 Hz, 2H), 7.07 (s, 1H), 7.16 (d, 2H), 7.35 (d, J=8.46 Hz, 1H), 7.37-7.50 (m, 3H), 7.63 (dd, J=8.40, 1.71 Hz, 1H), 8.94 (s, 1H).

Example 1.39

Preparation of 2-(((1s,4s)-4-((3-(6-Chloropyridin-3-yl)-6-oxo-4-phenylpyridazin-1(6H)-yl)methyl)cyclohexyl)methoxy)acetic Acid (Compound 65)

Step A: Preparation of tert-Butyl 2-(((1s,4s)-4-((3-(6-Chloropyridin-3-yl)-6-oxo-4-phenylpyridazin-1(6H)-yl)methyl)cyclohexyl)methoxy)acetate From 6-chloropyridin-3-ylboronic acid and tert-butyl 2-(((1s,4s)-4-((3-chloro-6-oxo-4-phenylpyridazin-1(6H)-yl)methyl)cyclohexyl)methoxy)acetate, the title compound was prepared using a similar method to the one described in Example 1.33, Step B, to give a white solid. LCMS m/z=524.7 [M+H]⁺.

Step B: Preparation of 2-(((1s,4s)-4-((3-(6-Chloropyridin-3-yl)-6-oxo-4-phenylpyridazin-1(6H)-yl)methyl)cyclohexyl)methoxy)acetic Acid From tert-butyl 2-(((1s,4s)-4-((3-(6-methylpyridin-3-yl)-6-oxo-4-phenylpyridazin-1(6H)-yl)methyl)cyclohexyl)methoxy)acetate, the title compound was prepared using a similar method to the one described in Example 1.33, Step C, to give a white solid. LCMS m/z=468.5 [M+H]⁺.

Example 1.40

Preparation of 2-(((1s,4s)-4-((3-oxo-6-phenyl-5-(pyridin-3-yl)-1,2,4-triazin-2(3H)-yl)methyl)cyclohexyl)methoxy)acetic Acid (Compound 77)

Step A: Preparation of Ethyl 3-Oxo-3-phenyl-2-(pyridin-3-yl)propanoate

To a cooled solution (−78° C.) of ethyl 2-(pyridin-3-yl)acetate (1.842 mL, 12.11 mmol) in THF (12.2 mL) was added LiHMDS (12.11 mL, 12.11 mmol) and the mixture was stirred 15 min. A solution of benzoyl chloride (1.474 mL, 12.71 mmol) in THF (24.4 mL) was added slowly and the mixture was warmed to room temperature and stirred for 12 h. The reaction was quenched with AcOH (1.386 mL, 24.21 mmol), diluted with H₂O (50 mL), and extracted with EtOAc (3×75 mL). The combined extracts were washed with brine, dried over MgSO₄ and concentrated. The residue was purified by silica gel column chromatography to give the title compound as a clear oil (1.82 g). LCMS m/z=270.2 [M+H]+.

Step B: Preparation of 1-Phenyl-2-(pyridine-3-yl)ethanone

Ethyl 3-oxo-3-phenyl-2-(pyridin-3-yl)propanoate (1.82 g, 6.76 mmol) was dissolved in hydrogen chloride (8.11 mL, 101.0 mmol) and heated to 100° C. overnight. The reaction was then diluted with $H_2O$ (25 mL), extracted with EtOAc (3×50 mL), dried over $MgSO_4$, filtered and concentrated. The residue was purified by silica gel column chromatography to give the title compound as a clear oil (0.894 g). LCMS m/z=198.3 [M+H]+; $^1$H NMR (400 MHz, $CDCl_3$) δ ppm 4.29 (s, 2H), 7.27 (dd, J=7.07, 5.56 Hz, 1H), 7.49 (t, J=7.58 Hz, 2H), 7.55-7.64 (m, 2H), 7.99-8.05 (m, 2H), 8.49-8.56 (m, 2H).

Step C: Preparation of 2-(Hydroxyimino)-1-phenyl-2-(pyridin-3-yl)ethanone

To a solution of 1-phenyl-2-(pyridine-3-yl)ethanone (0.494 g, 2.505 mmol) in EtOH (36.8 mL) at room temperature was added tert-butyl nitrite (0.586 mL, 4.93 mmol) dropwise followed by sodium ethoxide (0.435 g, 2.55 mmol). The reaction was stirred at room temperature overnight. Upon completion, the solvent was evaporated to give a yellow oil. This oil was then diluted with $H_2O$ (25 mL), extracted with EtOAc (3×50 mL), dried over $MgSO_4$, filtered and concentrated. The residue was purified by silica gel column chromatography to give the title compound as a yellow solid (0.214 g). LCMS m/z=227.4 [M+H]+.

Step D: Preparation of 3-(Methylthio)-6-phenyl-5-(pyridin-3-yl)-1,2,4-triazine

To a suspension of 2-(hydroxyimino)-1-phenyl-2-(pyridin-3-yl)ethanone (0.434 g, 1.918 mmol) in a 1:1 mixture of $EtOH/H_2O$ (8.0 mL) was added hydrazinecarbothioamide (0.262 g, 2.88 mmol) followed by concentrated HCl (0.307 mL, 3.84 mmol). The reaction was stirred at room temperature for 1 h then heated to 90° C. overnight. Upon completion, the reaction mixture was neutralized with saturated $NaHCO_3$. The solid formed was filtered and rinsed with $H_2O$. The solid was added to a solution of potassium carbonate (1.326 g, 9.59 mmol) in $H_2O$ (50 mL) and heated to 90° C. overnight. Upon completion, the reaction mixture was cooled to room temperature then placed in an ice bath. To the ice cooled mixture was added iodomethane (0.119 mL, 1.918 mmol). The reaction was stirred at 0° C. and slowly warmed to room temperature. After stirring overnight, the solution was extracted with $CH_2Cl_2$ (3×75 mL), washed with $H_2O$, brine, dried over $MgSO_4$ and concentrated. The residue was purified by silica gel column chromatography to give the title compound as a yellow solid (0.152 g). LCMS m/z=281.1 [M+H]+.

Step E: Preparation of 3-(Methylsulfonyl)-6-phenyl-5-(pyridin-3-yl)-1,2,4-triazine To a solution of 3-(methylthio)-6-phenyl-5-(pyridin-3-yl)-1,2,4-triazine (0.152 g, 0.542 mmol) in $CH_2Cl_2$ (3.0 mL) at 0° C. was added MCPBA (0.255 g, 1.139 mmol). The reaction mixture was stirred at 0° C. and then allowed to warm to room temperature overnight. The reaction was quenched with saturated $NaHCO_3$ solution and extracted with $CH_2Cl_2$. The organic extracts were washed with $H_2O$, brine, dried over $MgSO_4$ and concentrated. The residue was purified by silica gel column chromatography to give the title compound as a yellow solid (0.169 g). LCMS m/z=313.3 [M+H]+.

Step F: Preparation of 6-Phenyl-5-(pyridine-3-yl)-1,2,4-triazin-3(2H)-one

To a solution of 3-(methylsulfonyl)-6-phenyl-5-(pyridin-3-yl)-1,2,4-triazine (0.035 g, 0.112 mmol) in a 1:1 mixture of $H_2O/THF$ (1.5 mL) was added potassium hydroxide (0.037 g, 0.560 mmol). The reaction was heated at reflux for 2 h. Upon completion, the reaction mixture was cooled to room temperature and neutralized with 1 M HCl, then extracted with EtOAc. The combined organic layers were washed with $H_2O$, brine, dried over $MgSO_4$ and concentrated to give the title compound as a yellow solid (0.026 g) without further purification. LCMS m/z=251.1 [M+H]+.

Step G: Preparation of tert-Butyl 2-(((1s,4s)-4-((3-Oxo-6-phenyl-5-(pyridin-3-yl)-1,2,4-triazin-2(3H)-yl)methyl)cyclohexyl)methoxy)acetate To a solution 6-phenyl-5-(pyridin-3-yl)-1,2,4-triazin-3(2H)-one (0.034 g, 0.136 mmol) in dry DMF (1.5 mL) was added cesium carbonate (0.044 g, 0.136 mmol) and tert-butyl 2-(((1s,4s)-4-(tosyloxymethyl)cyclohexyl)methoxy)acetate (0.056 g, 0.136 mmol). The reaction mixture was heated to 80° C. and stirred for 1 h. Upon completion, the reaction mixture was quenched with $H_2O$ and extracted with EtOAc (twice). The combined organics layers were washed with brine, dried over $MgSO_4$, filtered and concentrated down to give the title compound as a yellow solid (0.067 g) without further purification. LCMS m/z=491.4 [M+H]+.

Step H: Preparation of 2-(((1s,4s)-4-((3-Oxo-6-phenyl-5-(pyridin-3-yl)-1,2,4-triazin-2(3H)-yl)methyl)cyclohexyl)methoxy)acetic Acid To tert-butyl 2-(((1s,4s)-4-((3-oxo-6-phenyl-5-(pyridin-3-yl)-1,2,4-triazin-2(3H)-yl)methyl)cyclohexyl)methoxy)acetate obtained above was added 4 M HCl (0.512 mL, 2.049 mmol) in 1,4-dioxane. The reaction was stirred at 25° C. for 16 h. The reaction was evaporated down to give a yellow oil. This yellow oil was purified by HPLC to give the TFA salt of the title compound (0.042 g) as a white solid. LCMS m/z=435.4 [M+H]+; $^1$H NMR (400 MHz, $CDCl_3$) δ ppm 1.43-1.68 (m, 8H), 1.83-1.96 (m, 1H), 2.32 (bs, 1H), 3.52 (d, J=7.07 Hz, 2H), 4.11 (s, 2H), 4.30 (d, J=7.07 Hz, 2H), 7.28 (s, 2H), 7.41 (t, J=7.45 Hz, 2H), 7.46 (d, J=7.33 Hz, 1H), 7.63 (d, 1H), 8.26 (d, J=8.08 Hz, 1H), 8.79 (s, 2H).

Example 1.41

Preparation of 2-(((1s,4s)-4-((3-Oxo-6-(pyridin-3-yl)-5-p-tolyl-1,2,4-triazin-2(3H)-yl)methyl)cyclohexyl)methoxy)acetic Acid (Compound 78)

Step A: Preparation of 2-(Hydroxyimino)-1-(pyridin-3-yl)-2-p-tolylethanone

From 1-(pyridin-3-yl)-2-p-tolylethanone, the title compound was prepared using a similar method to the one described in Example 1.40, Step C, to give a yellow oil. LCMS m/z=241.1[M+H]+.

Step B: Preparation of 3-(Methylthio)-6-(pyridin-3-yl)-5-p-tolyl-1,2,4-triazine

From 2-(hydroxyimino)-1-(pyridin-3-yl)-2-p-tolylethanone, the title compound was prepared using a similar method to the one described in Example 1.40, Step D, to give a yellow solid. LCMS m/z=295.2 [M+H]+.

Step C: Preparation of 3-(Methylsulfonyl)-6-(pyridin-3-yl)-5-p-tolyl-1,2,4-triazine From 3-(methylthio)-6-(pyridin-3-yl)-5-p-tolyl-1,2,4-triazine, the title compound was prepared using a similar method to the one described in Example 1.40, Step E, to give a yellow solid. LCMS m/z=327.2 [M+H]+.

Step D: Preparation of 6-(Pyridin-3-yl)-5-p-tolyl-1,2,4-triazin-3(2H)-one

From 3-(methylsulfonyl)-6-(pyridin-3-yl)-5-p-tolyl-1,2,4-triazine, the title compound was prepared using a similar method to the one described in Example 1.40, Step F, to give a yellow solid. LCMS m/z=265.1 [M+H]+.

Step E: Preparation of tert-Butyl 2-(((1s,4s)-4-((3-oxo-6-(pyridin-3-yl)-5-p-tolyl-1,2,4-triazin-2(3H)-yl)methyl)cyclohexyl)methoxy)acetate From 6-(pyridin-3-yl)-5-p-tolyl-1,2,4-triazin-3(2H)-one, the title compound was prepared using a similar method to the one described in Example 1.40, Step G, to give a yellow solid. LCMS m/z=505.4 [M+H]+.

Step F: Preparation of 2-(((1s,4s)-4-((3-Oxo-6-(pyridin-3-yl)-5-p-tolyl-1,2,4-triazin-2(3H)-yl)methyl)cyclohexyl)methoxy)acetic Acid From tert-butyl 2-(((1s,4s)-4-((3-oxo-6-phenyl-5-(pyridin-3-yl)-1,2,4-triazin-2(3H)-yl)methyl)cyclohexyl)methoxy)acetate, the TFA salt of the title compound was prepared using a similar method to the one described in Example 1.40, Step H, to give a white solid. LCMS m/z=449.2 [M+H]+; 1H NMR (400 MHz, CDCl3) δ ppm 1.43-1.75 (m, 8H), 1.82-1.94 (m, 2H), 2.41 (s, 3H), 3.54 (d, J=7.07 Hz, 2H), 4.14 (s, 2H), 4.32 (d, J=8.34 Hz, 2H), 7.17-7.24 (m, 2H), 7.39 (d, J=8.08 Hz, 2H), 7.66 (bs, 1H), 7.85 (d, J=8.08 Hz, 1H), 9.20 (bs, 1H), 9.45 (bs, 1H).

Example 1.42

Preparation of 2-(((1s,4s)-4-((3-Oxo-5-(pyridin-4-yl)-6-p-tolyl-1,2,4-triazin-2(3H)-yl)methyl)cyclohexyl)methoxy)acetic Acid (Compound 79)

From 2-(pyridin-4-yl)-1-p-tolylethanone, the TFA salt of the title compound was prepared using a similar method to the one described in Example 1.41 to give a white solid. LCMS m/z=449.3 [M+H]+; 1H NMR (400 MHz, CDCl3) δ ppm 1.43-1.69 (m, 8H), 1.78-1.94 (m, 2H), 2.40 (s, 3H), 3.52 (d, J=7.07 Hz, 2H), 4.11 (s, 2H), 4.26 (d, J=7.58 Hz, 2H), 7.12 (d, J=8.00 Hz, 2H), 7.20 (d, J=8.00 Hz, 2H), 7.69 (bs, 2H), 8.75 (bs, 2H).

Example 1.43

Preparation of 2-(((1r,4r)-4-((4-(3-Methoxyphenyl)-6-oxo-3-phenylpyridazin-1(6H)-yl)methyl)cyclohexyl)methoxy)acetic Acid (Compound 1)

A mixture of tert-butyl 2-(((1r,4r)-4-((methylsulfonyloxy)methyl)cyclohexyl)methoxy)acetate (30.0 mg, 0.089 mmol), 5-(3-methoxyphenyl)-6-phenylpyridazin-3(2H)-one (27.3 mg, 0.098 mmol), potassium tert-butoxide (25.01 mg, 0.223 mmol) and 18-crown-6 (4.71 mg, 0.018 mmol) in DMF (2 mL) was stirred overnight at room temperature. The reaction was quenched with water, extracted with EtOAc and dried over anhydrous MgSO4 and concentrated. The residue was purified by preparative HPLC to give the title compound as a pale yellow solid (4.90 mg). LCMS m/z=463.3 [M+H]+; 1H NMR (400 MHz, CDCl3) δ ppm 0.96-1.06 (m, 2H), 1.13-1.23 (m, 2H), 1.63-1.69 (m, 1H), 1.81-1.88 (m, 4H), 2.03-2.08 (m, 1H), 3.39 (d, J=6.5 Hz, 2H), 3.63 (s, 3H), 4.09 (s, 2H), 4.18 (d, J=7.3 Hz, 2H), 6.60 (t, J=2 Hz, 1H), 6.71 (d, J=7.6 Hz, 1H), 6.88 (dd, J=8.3 Hz, 2.5 Hz, 1H), 7.12 (s, 1H), 7.18-7.23 (m, 3H), 7.25-7.35 (m, 3H).

Example 1.44

Preparation of 2-(((1r,4r)-4-((3-Benzhydryl-6-oxopyridazin-1(6H)-yl)methyl)cyclohexyl)methoxy)acetic Acid (Compound 7)

To a solution of 6-benzhydrylpyridazin-3(2H)-one (30 mg, 0.114 mmol) and K2CO3 (39.5 mg, 0.286 mmol) in DMF (1 mL) at room temperature was added tert-butyl 2-(((1r,4r)-4-(tosyloxymethyl)cyclohexyl)methoxy)acetate (47.2 mg, 0.114 mmol). The reaction was stirred at 40° C. overnight, quenched with water and extracted with EtOAc. The EtOAc extracts were dried over MgSO4 and concentrated. The residue was treated with 4 M HCl in dioxane (0.029 mL, 0.114 mmol) and purified by preparative LCMS to give the title compound as a white solid (20 mg). LCMS m/z=447.2 [M+H]+; 1H NMR (400 MHz, CDCl3) δ ppm 1.08-0.88 (m, 4H), 1.55-1.64 (m, 1H), 1.65 (d, J=12.8 Hz, 2H), 1.80 (d, J=11.6 Hz, 2H), 1.85-1.95 (m, 1H), 3.36 (d, J=6.3 Hz, 2H), 4.0 (d, J=7.08 Hz, 2H), 4.08 (s, 2H), 5.46 (s, 1H), 6.99 (d, J=9.3 Hz, 2H), 7.12-7.16 (m, 5H), 7.24-7.34 (m, 5H).

Example 1.45

Preparation of 2-(((1r,4r)-4-((6-Oxo-3,4-diphenylpyridazin-1(6H)-yl)methyl)cyclohexyl)methoxy)acetic Acid (Compound 19)

To a solution of 5,6-diphenylpyridazin-3(2H)-one (30 mg, 0.121 mmol) and potassium carbonate (50.1 mg, 0.362 mmol) in DMF (1 mL) at room temperature was added tert-butyl 2-(((1r,4r)-4-(tosyloxymethyl)cyclohexyl)methoxy)acetate (49.8 mg, 0.121 mmol). The reaction was stirred at 40° C. overnight. NaOH (0.201 mL, 0.604 mmol) was added and the reaction was again stirred overnight before quenched with water and extracted with EtOAc. The EtOAc extracts were concentrated and purified by preparative LCMS to give a white solid (17.1 mg). LCMS m/z=433.2 [M+H]+; NMR (400 MHz, CDCl3) δ ppm 0.96-1.06 (m, 2H), 1.13-1.23 (m, 2H), 1.61-1.71 (m, 1H), 1.80-1.88 (t, J=16 Hz, 4H), 2.03-2.07 (m, 1H), 3.38 (d, J=6.3 Hz, 2H), 4.09 (s, 2H), 4.18 (d, J=7.3 Hz, 2H), 7.10-7.13 (m, 3H), 7.16-7.19 (m, 2H), 7.36-7.24 (m, 5H).

Example 1.46

Preparation of 2-(((1s,4s)-4-((4-(3-Chlorophenyl)-6-oxo-3-p-tolylpyridazin-Acid (Compound 47)

Step A: Preparation of 3,4-Dibromo-5-p-tolylfuran-2(5H)-one

To a mixture of 3,4-dibromo-5-hydroxyfuran-2(5H)-one (0.5 g, 1.939 mmol) in toluene (5 mL, 1.939 mmol) was added AlCl₃ (0.310 g, 2.327 mmol) at room temperature. The mixture was stirred at room temperature overnight. The reaction was quenched with water, extracted with EtOAc (3×20 mL), dried over anhydrous MgSO₄, and filtered. The filtrate was concentrated under reduced pressure to give the title compound without further purification. LCMS m/z=332.8 [M+H]⁺.

Step B: Preparation of 5-Bromo-6-p-tolylpyridazin-3(2H)-one

To a mixture of 3,4-dibromo-5-p-tolylfuran-2(5H)-one (0.5 g, 1.506 mmol) in ethanol (5 mL) was added NH₂NH₂ (0.047 mL, 1.506 mmol) at 0° C. The mixture was stirred at room temperature overnight. The precipitate was filtered and dried under reduced pressure to give the title compound as a beige solid (0.22 g). LCMS m/z=264.9 [M+H]⁺.

Step C: Preparation of 5-(3-Chlorophenyl)-6-p-tolylpyridazin-3(2H)-one

In a 10 mL heavy-walled sealed tube, a mixture of 5-bromo-6-p-tolylpyridazin-3(2H)-one (0.05 g, 0.189 mmol), 3-chlorophenylboronic acid (0.029 g, 0.189 mmol), Pd(Ph₃P)₄ (10.90 mg, 9.43 µmol) and K₂CO₃ (0.283 mL, 0.566 mmol) in dioxane (2 mL) was heated under microwave irradiation at 130° C. for 2 h. The reaction was purified by preparative HPLC to give the title compound (0.032 g). LCMS m/z=297.1 [M+H]⁺.

Step D: Preparation of 2-(((1s,4s)-4-((4-(3-Chlorophenyl)-6-oxo-3-p-tolylpyridazin-1(6H)-yl)methyl)cyclohexyl)methoxy)acetic Acid A mixture of 5-(3-chlorophenyl)-6-p-tolylpyridazin-3(2H)-one (30 mg, 0.101 mmol), tert-butyl 2-(((1s,4s)-4-((methylsulfonyloxy)methyl)cyclohexyl)methoxy)acetate (34.0 mg, 0.101 mmol), potassium tert-butoxide (22.69 mg, 0.202 mmol) and 18-crown-6 (5.34 mg, 0.020 mmol) in DMF (2 mL) was stirred at room temperature overnight. The reaction was purified by preparative LCMS to give the title compound as white solid (1 mg). LCMS m/z=481.1 [M+H]⁺; ¹H NMR (400 MHz, CDCl₃) δ ppm 1.63-1.44 (m, 8H), 2.04-1.78 (m, 2H), 2.33 (s, 3H), 3.52 (d, J=6.8 Hz, 2H), 4.10 (s, 2H), 4.23 (d, J=7.6 Hz, 2H), 6.92 (s, 1H), 6.95 (d, J=8 Hz, 1H), 7.03-7.09 (m, 4H), 7.16 (t, J=1.8 Hz, 1H), 7.32 (d, 1H, J=8 Hz), 7.20 (t, J=8 Hz, 1H).

Example 1.47

Preparation of 2(((1s,4s)-4-((6-Oxo-3,4-diphenylpyridazin-1(6H)-yl)methyl)cyclohexyl)methoxy)acetic Acid (Compound 3)

The title compound was prepared using a similar method to the one described in Example 1.43 to give a white solid. LCMS m/z=433.2 [M+H]⁺.

Example 1.48

Preparation of 2-(((1s,4s)-4-((3-Benzhydryl-6-oxopyridazin-1(6H)-yl)methyl)cyclohexyl)methoxy)acetic Acid (Compound 4)

The title compound was prepared using a similar method to the one described in Example 1.43 to give a white solid. LCMS m/z=446.9 [M+H]⁺.

Example 1.49

Preparation of 2-(((1s,4s)-4-((3-(4-Methoxyphenyl)-6-oxo-4-phenylpyridazin-1(6H)-yl)methyl)cyclohexyl)methoxy)acetic Acid (Compound 5)

The title compound was prepared using a similar method to the one described in Example 1.43 to give a white solid. LCMS m/z=463.1 [M+H]⁺.

Example 1.50

Preparation of 2-(((1s,4s)-4-((3-(3-Fluorophenyl)-6-oxo-4-phenylpyridazin-1(6H)-yl)methyl)cyclohexyl)methoxy)acetic Acid (Compound 21)

Step A: Preparation of 2-Benzyl-6-hydroxy-5-phenylpyridazin-3(2H)-one

3-Phenylfuran-2,5-dione (2.00 g, 11.5 mmol), benzylhydrazine (3.36 g, 17.2 mmol) and acetic acid (2 mL) were heated to 140° C. for 3 h in a 20 mL heavy-walled sealed tube under microwave irradiation. Upon cooling, a white precipitate formed which was filtered and washed three times with hexane and DCM. The white solid was dried under reduced pressure to give the title compound (11.01 g). LCMS m/z=279.2 [M+H]⁺; ¹H NMR (400 MHz, DMSO-d₆) δ ppm 5.13 (s, 2H), 7.00 (s, 1H), 7.42-7.26 (m, 5H), 7.49-7.43 (m, 3H), 7.66-7.60 (m, 2H).

Step B: Preparation of 2-Benzyl-6-hydroxy-5-phenylpyridazin-3(2H)-one

2-Benzyl-6-hydroxy-5-phenylpyridazin-3(2H)-one (3.33 g, 12.0 mmol) and phosphorus oxychloride (11.2 mL, 119.6 mmol) were heated to 120° C. for 0.5 h in a 20 mL heavy-walled sealed tube under microwave irradiation. The mixture was concentrated under reduced pressure and purified by column chromatography to give the title compound as an orange solid (1.466 g). LCMS m/z=297.2 [M+H]⁺; ¹H NMR (400 MHz, CDCl₃) δ ppm 5.32 (s, 2H), 6.91 (s, 1H), 7.43-7.31 (m, 5H), 7.55-7.44 (m, 5H).

Step C: Preparation of 6-Chloro-5-phenylpyridazin-3(2H)-one

To a solution of 2-benzyl-6-chloro-5-phenylpyridazin-3(2H)-one (1.45 g, 4.89 mmol) in toluene (15 mL) under argon at 90° C. was added aluminum chloride (1.629 g, 12.22 mmol) and the reaction was stirred for 20 min. It was then allowed to cool to room temperature and quenched with water, extracted with EtOAc, dried over MgSO₄ and concentrated. The residue was purified by preparative HPLC to give the title compound as a white solid (847.6 mg). LCMS m/z=207 [M+H]⁺; ¹H NMR (400 MHz, CDCl₃) δ ppm 6.97 (s, 1H), 7.41-7.54 (m, 5H).

Step D: Preparation of tert-Butyl 2-(41s,4s)-4-((3-Chloro-6-oxo-4-phenylpyridazin-1(6H)-yl)methyl)cyclohexyl)methoxy)acetate To a solution of 6-chloro-5-phenylpyridazin-3(2H)-one (407 mg, 1.970 mmol) and potassium carbonate (544 mg, 3.94 mmol) in DMF (2 mL) at room temperature was added tert-butyl 2-(((1s,4s)-4-(tosyloxymethyl)cyclohexyl)methoxy)acetate (813 mg, 1.970 mmol). The reaction was stirred at 40° C. overnight, quenched with water and extracted with EtOAc. The organic extracts were concentrated and purified by silica gel column chromatography to give the title compound as a clear oil (678 mg). LCMS m/z=447.3 [M+H]$^+$; $^1$H NMR (400 MHz, CDCl$_3$) δ ppm 1.49 (s, 9H), 1.58-1.51 (m, 4H), 1.62 (bs, 4H), 1.84-1.90 (m, 1H), 2.20-2.27 (m, 1H), 3.45 (d, J=7.07 Hz, 2H), 3.96 (s, 2H), 4.13 (d, J=7.58 Hz, 2H), 6.89 (s, 1H), 7.42-7.44 (m, 2H), 7.45-7.50 (m, 3H).

Step E: Preparation of 2-(((1s,4s)-4-((3-(3-Fluorophenyl)-6-oxo-4-phenylpyridazin-1(6H)-yl)methyl)cyclohexyl)methoxy)acetic Acid To a solution of tert-butyl 2-(((1s,4s)-4-((3-chloro-6-oxo-4-phenylpyridazin-1(6H)-yl)methyl)cyclohexyl)methoxy)acetate (30.0 mg, 0.067 mmol) in dioxane (1 mL) was added the 3-fluorophenylboronic acid (10.3 mg, 0.074 mmol), 2 M K$_2$CO$_3$ (0.084 mL, 0.168 mmol) and Pd(PPh$_3$)$_4$ (7.76 mg, 0.007 mmol). The reaction was heated under microwave irradiation at 130° C. for 2 h. The reaction was filtered through a celite column with EtOAc and concentrated. The residue was added 4 M HCl in dioxane (0.168 mL, 0.671 mmol) and the reaction was stirred overnight. The reaction was concentrated and purified by preparative LCMS to give the title compound as a white solid (11.6 mg). LCMS m/z=451.1 [M+H]$^+$; $^1$H NMR (400 MHz, CDCl$_3$) δ ppm 1.65-1.42 (m, 8H), 1.83-1.93 (m, 1H), 2.27-2.36 (m, 1H), 3.53 (d, J=6.82 Hz, 2H), 4.14-4.09 (m, 2H), 4.29 (d, J=7.83 Hz, 2H), 6.87-6.97 (m, 2H), 7.02 (td, J=8.34 Hz, 2.53 Hz, 1H), 7.16-7.09 (m, 3H), 7.21 (td, J=8.02, 5.94 Hz, 1H), 7.40-7.29 (m, 3H).

Example 1.51

Preparation of 2-(((1s,4s)-4-((3-(2-Fluoro-4-methylphenyl)-6-oxo-4-phenylpyridazin-1(6H)-yl)methyl)cyclohexyl)methoxy)acetic Acid (Compound 40)

The title compound was prepared using a similar method to the one described in Example 1.50 to give a white solid. LCMS m/z=465.1 [M+H]$^+$; $^1$H NMR (400 MHz, CDCl$_3$) ppm 1.36-1.51 (m, 8H), 1.72-1.84 (m, 1H), 2.17-2.24 (m, 1H), 2.28 (s, 3H), 3.39-3.46 (m, 2H), 3.94 (s, 2H), 4.12-4.19 (m, 2H), 6.65 (d, J=10 Hz, 1H), 6.91 (s, 1H), 6.92 (d, J=7 Hz, 1H), 7.06 (d, J=7.6 Hz, 2H), 7.28-7.14 (m, 4H).

Example 1.52

Preparation of 2-(((1s,4s)-4-((3-(4-Chloro-2-fluorophenyl)-6-oxo-4-phenylpyridazin-1(6H)-yl)methyl)cyclohexyl)methoxy)acetic Acid (Compound 52)

The title compound was prepared using a similar method to the one described in Example 1.50 to give a white solid. LCMS m/z=484.9 [M+H]$^+$; $^1$H NMR (400 MHz, CDCl$_3$) δ ppm 1.61-1.47 (m, 8H), 1.81-1.90 (m, 1H), 2.31 (s, 1H), 3.52 (d, J=6.5 Hz, 2H), 4.10 (s, 2H), 4.25 (d, J=7.6 Hz, 2H), 6.94 (dd, J=8 Hz, 2 Hz, 1H), 7.04 (s, 1H), 7.09 (d, J=7.3 Hz, 2H), 7.16 (dd, J=8 Hz, 2 Hz, 1H), 7.22 (d, J=8 Hz, 1H), 7.29 (d, J=8 Hz, 2H), 7.34 (d, J=8 Hz, 1H).

Example 1.53

Preparation of 2-(((1s,4s)-4-((3-(4-Chloro-3-fluorophenyl)-6-oxo-4-phenylpyridazin-1(6H)-yl)methyl)cyclohexyl)methoxy)acetic Acid (Compound 53)

The title compound was prepared using a similar method to the one described in Example 1.50 to give a white solid. LCMS m/z=485.4 [M+H]$^+$; $^1$H NMR (400 MHz, CDCl$_3$) δ ppm 1.62-1.48 (m, 8H), 1.82-1.91 (m, 1H), 2.28-2.35 (m, 1H), 3.53 (d, J=7 Hz, 2H), 4.11 (s, 2H), 4.25 (d, J=7.5 Hz, 2H), 6.83 (dd, J=8 Hz, 2 Hz, 1H), 6.99 (s, 1H), 7.03 (dd, J=8 Hz, 2 Hz, 1H), 7.12 (d, J=8 Hz, 2H), 7.22 (d, J=7.6 Hz, 1H), 7.41-7.30 (m, 3H).

Example 1.54

Preparation of 2-(((1s,4s)-4-((3-(3-Fluoro-4-methylphenyl)-6-oxo-4-phenylpyridazin-1(6H)-yl)methyl)cyclohexyl)methoxy)acetic Acid (Compound 38)

The title compound was prepared using a similar method to the one described in Example 1.50 to give a white solid. LCMS m/z=487.5 [M+H]$^+$; $^1$H NMR (400 MHz, CDCl$_3$) δ ppm 1.57-1.49 (m, 8H), 1.84-1.91 (m, 1H), 2.24 (s, 3H), 3.52 (d, J=6 Hz, 2H), 2.28-2.34 (m, 1H), 4.23 (d, J=8 Hz, 2H), 4.09 (s, 2H), 6.76 (d, J=8 Hz, 1H), 6.87 (d, J=11 Hz, 1H), 6.93 (s, 1H), 7.01 (dd, J$_1$=J$_2$=8 Hz, 1H), 7.12 (d, J=8 Hz, 2H), 7.36-7.27 (m, 3H).

Example 1.55

Preparation of 2-(((1s,4s)-4-((6-oxo-4-phenyl-3-p-tolylpyridazin-1(6H)-yl)methyl)cyclohexyl)methoxy)acetic Acid (Compound 20)

The title compound was prepared using a similar method to the one described in Example 1.50 to give a white solid. LCMS m/z=469.1 [M+H]$^+$; $^1$H NMR (400 MHz, CDCl$_3$) δ ppm 1.52-1.44 (m, 8H), 1.83 (bs, 1H), 2.17 (bs, 1H), 2.30 (s, 3H), 3.48 (d, J=6 Hz, 2H), 4.02 (s, 2H), 4.20 (d, J=8 Hz, 2H), 6.91 (s, 1H), 7.03 (s, 4H), 7.09 (d, J=8 Hz, 2H), 7.31-7.24 (m, 3H).

Example 1.56

Preparation of 2-(((1s,4s)-4-((3-(4-Fluorophenyl)-6-oxo-4-phenylpyridazin-1(6H)-yl)methyl)cyclohexyl)methoxy)acetic Acid (Compound 22)

The title compound was prepared using a similar method to the one described in Example 1.50 to give a white solid. LCMS m/z=451.1 [M+H]$^+$.

Example 1.57

Preparation of 2-(((1s,4s)-4-((3-(2-Chlorophenyl)-6-oxo-4-phenylpyridazin-1(6H)-yl)methyl)cyclohexyl)methoxy)acetic Acid (Compound 23)

The title compound was prepared using a similar method to the one described in Example 1.50 to give a white solid. LCMS m/z=467.4 [M+H]$^+$.

Example 1.58

Preparation of 2-(((1s,4s)-4-((3-(4-Chlorophenyl)-6-oxo-4-phenylpyridazin-1(6H)-yl)methyl)cyclohexyl)methoxy)acetic Acid (Compound 24)

The title compound was prepared using a similar method to the one described in Example 1.50 to give a white solid. LCMS m/z=467.3 [M+H]$^+$.

Example 1.59

Preparation of 2-(((1s,4s)-4-((3-(2-Methoxyphenyl)-6-oxo-4-phenylpyridazin-1(6H)-yl)methyl)cyclohexyl)methoxy)acetic Acid (Compound 25)

The title compound was prepared using a similar method to the one described in Example 1.50 to give a white solid. LCMS m/z=463.2 [M+H]$^+$.

Example 1.60

Preparation of 2-(((1s,4s)-4-((3-(3-Methoxyphenyl)-6-oxo-4-phenylpyridazin-1(6H)-yl)methyl)cyclohexyl)methoxy)acetic Acid (Compound 26)

The title compound was prepared using a similar method to the one described in Example 1.50 to give a white solid. LCMS m/z=463.2 [M+H]$^+$.

Example 1.61

Preparation of 2-(((1s,4s)-4-((3-(3-Fluoro-5-methoxyphenyl)-6-oxo-4-phenylpyridazin-1(6H)-yl)methyl)cyclohexyl)methoxy)acetic Acid (Compound 27)

The title compound was prepared using a similar method to the one described in Example 1.50 to give a white solid. LCMS m/z=481.3 [M+H]$^+$.

Example 1.62

Preparation of 2-(((1s,4s)-4-((3-(2,3-Fifluorophenyl)-6-oxo-4-phenylpyridazin-1(6H)-yl)methyl)cyclohexyl)methoxy)acetic Acid (Compound 28)

The title compound was prepared using a similar method to the one described in Example 1.50 to give a white solid. LCMS m/z=469.4 [M+H]$^+$.

Example 1.63

Preparation of 2-(((1s,4s)-4-((3-(3-Chlorophenyl)-6-oxo-4-phenylpyridazin-1(6H)-yl)methyl)cyclohexyl)methoxy)acetic Acid (Compound 29)

The title compound was prepared using a similar method to the one described in Example 1.50 to give a white solid. LCMS m/z=467.6 [M+H]$^+$.

Example 1.64

Preparation of 2-(((1s,4s)-4-((3-(2-Fluorophenyl)-6-oxo-4-phenylpyridazin-1(6H)-yl)methyl)cyclohexyl)methoxy)acetic Acid (Compound 35)

The title compound was prepared using a similar method to the one described in Example 1.50 to give a white solid. LCMS m/z=451.1 [M+H]$^+$.

Example 1.65

Preparation of 2-(((1s,4s)-4-((3-(4-Ethylphenyl)-6-oxo-4-phenylpyridazin-1(6H)-yl)methyl)cyclohexyl)methoxy)acetic Acid (Compound 36)

The title compound was prepared using a similar method to the one described in Example 1.50 to give a white solid. LCMS m/z=461.3 [M+H]$^+$.

Example 1.66

Preparation of 2-(((1s,4s)-4-((6-Oxo-4-phenyl-3-(4-(trifluoromethyl)phenyl)pyridazin-1(6H)-yl)methyl)cyclohexyl)methoxy)acetic Acid (Compound 37)

The title compound was prepared using a similar method to the one described in Example 1.50 to give a white solid. LCMS m/z=501.2 [M+H]$^+$.

Example 1.67

Preparation of 2-(((1s,4s)-4-((3-(4-Isopropylphenyl)-6-oxo-4-phenylpyridazin-1(6H)-yl)methyl)cyclohexyl)methoxy)acetic Acid (Compound 39)

The title compound was prepared using a similar method to the one described in Example 1.50 to give a white solid. LCMS m/z=475.1 [M+H]$^+$.

Example 1.68

Preparation of 2-(((1s,4s)-4-((3-(4-(Methylthio)phenyl)-6-oxo-4-phenylpyridazin-1(6H)-yl)methyl)cyclohexyl)methoxy)acetic Acid (Compound 41)

The title compound was prepared using a similar method to the one described in Example 1.50 to give a white solid. LCMS m/z=479.3 [M+H]$^+$.

Example 1.69

Preparation of 2-(((1s,4s)-4-((6-Oxo-3-phenyl-4-(1H-pyrazol-4-yl)pyridazin-1(6H)-yl)methyl)cyclohexyl)methoxy)acetic Acid (Compound 46)

The title compound was prepared using a similar method to the one described in Example 1.50 to give a white solid. LCMS m/z=422.9 [M+H]$^+$.

Example 1.70

Preparation of 2-(((1s,4s)-4-((6-Oxo-3-phenyl-4-(pyridin-3-yl)pyridazin-1(6H)-yl)methyl)cyclohexyl)methoxy)acetic Acid (Compound 44)

The title compound was prepared using a similar method to the one described in Example 1.50 to give a white solid. LCMS m/z=434.2 [M+H]$^+$.

Example 1.71

Preparation of 2-(((1s,4s)-4-((4-(3-Fluoro-5-methoxyphenyl)-6-oxo-3-phenylpyridazin-1(6H)-yl)methyl)cyclohexyl)methoxy)acetic Acid (Compound 18)

Step A: Preparation of 5-Bromo-6-phenylpyridazin-3(2H)-one

To a solution of 3,4-dibromo-5-phenylfuran-2(5H)-one (4.951 g, 15.57 mmol) in EtOH (5 mL) at 0° C. was added hydrazine, H$_2$O (0.840 mL, 17.13 mmol). The reaction mixture was stirred at room temperature for 10 min before heating to reflux for 2 h. The reaction was cooled to room temperature. The precipitate formed was collected by filtration and washed with cold ethanol to yield the title compound as a pale yellow solid (2.530 g). LCMS m/z=351 [M+H]+; 1H NMR (400 MHz, DMSO-d6) δ ppm 7.47-7.49 (m, 3H), 7.51-7.54 (m, 3H).

Step B: Preparation of tert-Butyl 2-(((1s,4s)-4-((4-Bromo-6-oxo-3-phenylpyridazin-1(6H)-yl)methyl)cyclohexyl)methoxy)acetate To a solution of 5-bromo-6-phenylpyridazin-3(2H)-one (1.080 g, 4.30 mmol) and potassium carbonate (1.189 g, 8.60 mmol) in DMF (10 mL) at room temperature was added tert-butyl 2-(((1s,4s)-4-(tosyloxymethyl)cyclohexyl)methoxy)acetate (1.775 g, 4.30 mmol). The reaction was stirred overnight at 40° C., quenched with water and extracted with EtOAc. The organic extracts were concentrated and purified by silica gel column chromatography to give the title compound as a clear oil (431 mg). LCMS m/z=491.4 [M+H]+; 1H NMR (400 MHz, CDCl3) δ ppm 1.48 (s, 9H), 1.60-1.49 (m, 4H), 1.80-1.88 (m, 1H), 2.26 (bs, 4H), 2.73 (t, J=4.80 Hz, 1H), 3.42 (t, J=3.41 Hz, 2H), 3.94 (s, 2H), 4.15 (d, J=7.58 Hz, 2H), 7.38 (s, 1H), 7.48-7.44 (m, 3H), 7.55-7.50 (m, 2H).

Step C: Preparation of 2-(((1s,4s)-4-((4-(3-Fluoro-5-methoxyphenyl)-6-oxo-3-phenylpyridazin-1(6H)-yl)methyl)cyclohexyl)methoxy)acetic Acid To a solution of tert-butyl 2-(((1s,4s)-4-((4-bromo-6-oxo-3-phenylpyridazin-1(6H)-yl)methyl)cyclohexyl)methoxy)acetate (30 mg, 0.061 mmol) in dioxane (0.5 mL) was added 3-fluoro-5-methoxyphenylboronic acid (12.5 mg, 0.073 mmol), Pd(PPh3)4 (7.05 mg, 0.0061 mmol) and 2 M potassium carbonate (0.076 mL, 0.153 mmol). The reaction was heated under microwave irradiation at 130° C. for 1 h. It was filtered through a celite column with EtOAc and concentrated. The residue was added 4 M HCl in dioxane (10 eq.) and stirred overnight. The mixture was extracted with EtOAc. The EtOAc extracts were concentrated and the residue was purified by preparative LCMS to give the title compound as a white solid (3.4 mg). LCMS m/z=481.2 [M+H]+.

Example 1.72

Preparation of 2-(((1s,4s)-4-((4-(3-Methoxyphenyl)-6-oxo-3-phenylpyridazin-1(6H)-yl)methyl)cyclohexyl)methoxy)acetic Acid (Compound 2)

The title compound was prepared using a similar method to the one described in Example 1.71 to give a white solid. LCMS m/z=463.3 [M+H]+.

Example 1.73

Preparation of 2-(((1s,4s)-4-((6-Oxo-3-phenyl-4-m-tolylpyridazin-1(6H)-yl)methyl)cyclohexyl)methoxy)acetic Acid (Compound 9)

The title compound was prepared using a similar method to the one described in Example 1.71 to give a white solid. LCMS m/z=447.0 [M+H]+.

Example 1.74

Preparation of 2-(((1s,4s)-4-((6-Oxo-3-phenyl-4-p-tolylpyridazin-1(6H)-yl)methyl)cyclohexyl)methoxy)acetic Acid (Compound 10)

The title compound was prepared using a similar method to the one described in Example 1.71 to give a white solid. LCMS m/z=446.9 [M+H]+.

Example 1.75

Preparation of 2-(((1s,4s)-4-((4-(3-Fluorophenyl)-6-oxo-3-phenylpyridazin-1(6H)-yl)methyl)cyclohexyl)methoxy)acetic Acid (Compound 11)

The title compound was prepared using a similar method to the one described in Example 1.71 to give a white solid. LCMS m/z=451.1 [M+H]+.

Example 1.76

Preparation of 2-(((1s,4s)-4-((4-(4-Fluorophenyl)-6-oxo-3-phenylpyridazin-1(6H)-yl)methyl)cyclohexyl)methoxy)acetic Acid (Compound 12)

The title compound was prepared using a similar method to the one described in Example 1.71 to give a white solid. LCMS m/z=451.1 [M+H]+.

Example 1.77

Preparation of 2-(((1s,4s)-4-((4-(2-Chlorophenyl)-6-oxo-3-phenylpyridazin-1(6H)-yl)methyl)cyclohexyl)methoxy)acetic Acid (Compound 13)

The title compound was prepared using a similar method to the one described in Example 1.71 to give a white solid. LCMS m/z=467.3 [M+H]+.

Example 1.78

Preparation of 2-(((1s,4s)-4-((4-(4-Chlorophenyl)-6-oxo-3-phenylpyridazin-1(6H)-yl)methyl)cyclohexyl)methoxy)acetic Acid (Compound 14)

The title compound was prepared using a similar method to the one described in Example 1.71 to give a white solid. LCMS m/z=467.3 [M+H]+.

Example 1.79

Preparation of 2-(((1s,4s)-4-((4-(2-Methoxyphenyl)-6-oxo-3-phenylpyridazin-1(6H)-yl)methyl)cyclohexyl)methoxy)acetic Acid (Compound 15)

The title compound was prepared using a similar method to the one described in Example 1.71 to give a white solid. LCMS m/z=463.3 [M+H]+.

Example 1.80

Preparation of 2-(((1s,4s)-4-((4-(4-Methoxyphenyl)-6-oxo-3-phenylpyridazin-1(6H)-yl)methyl)cyclohexyl)methoxy)acetic Acid (Compound 16)

The title compound was prepared using a similar method to the one described in Example 1.71 to give a white solid. LCMS m/z=463.4 [M+H]+.

Example 1.81

Preparation of 2-(((1s,4s)-4-((4-(2-Fluoro-3-methoxyphenyl)-6-oxo-3-phenylpyridazin-1(6H)-yl)methyl)cyclohexyl)methoxy)acetic Acid (Compound 17)

The title compound was prepared using a similar method to the one described in Example 1.71 to give a white solid. LCMS m/z=481.2 [M+H]+.

Example 1.82

Preparation of 2-(((1s,4s)-4-((4-(5-Chloro-2-fluorophenyl)-6-oxo-3-phenylpyridazin-1(6H)-yl)methyl)cyclohexyl)methoxy)acetic Acid (Compound 30)

The title compound was prepared using a similar method to the one described in Example 1.71 to give a white solid. LCMS m/z=485.3 [M+H]+.

Example 1.83

Preparation of 2-(((1s,4s)-4-((4-(3-Chloro-4-fluorophenyl)-6-oxo-3-phenylpyridazin-1(6H)-yl)methyl)cyclohexyl)methoxy)acetic Acid (Compound 32)

The title compound was prepared using a similar method to the one described in Example 1.71 to give a white solid. LCMS m/z=485.3 [M+H]+.

Example 1.84

Preparation of 2-(((1s,4s)-4-((4-(3,5-Dichlorophenyl)-6-oxo-3-phenylpyridazin-1(6H)-yl)methyl)cyclohexyl)methoxy)acetic Acid (Compound 33)

The title compound was prepared using a similar method to the one described in Example 1.71 to give a white solid. LCMS m/z=501.3 [M+H]+.

Example 1.85

Preparation of 2-(((1s,4s)-4-((4-(3,4-Dichlorophenyl)-6-oxo-3-phenylpyridazin-1(6H)-yl)methyl)cyclohexyl)methoxy)acetic Acid (Compound 34)

The title compound was prepared using a similar method to the one described in Example 1.71 to give a white solid. LCMS m/z=501.4 [M+H]+.

Example 1.86

Preparation of 2-(((1s,4s)-4-((4-(3-Chlorophenyl)-6-oxo-3-phenylpyridazin-1(6H)-yl)methyl)cyclohexyl)methoxy)acetic Acid (Compound 6)

The title compound was prepared using a similar method to the one described in Example 1.71 to give a white solid. The title compound was converted to its sodium salt by treating it with one equivalent of sodium methoxide. LCMS m/z=467.5 [M+H]+.

Example 1.87

Preparation of 2-(((1s,4s)-4-((5-(3-Chlorophenyl)-3-oxo-6-p-tolyl-1,2,4-triazin-2(3H)-yl)methyl)cyclohexyl)methoxy)acetic Acid (Compound 85)

Step A: Preparation of tert-Butyl 2-(((1s,4s)-4-((5-(3-chlorophenyl)-3-oxo-6-p-tolyl-1,2,4-triazin-2(3H)-yl)methyl)cyclohexyl)methoxy)acetate From 5-(3-chlorophenyl)-6-p-tolyl-1,2,4-triazin-3(2H)-one and tert-butyl 2-(((1s,4s)-4-(tosyloxymethyl)cyclohexyl)methoxy)acetate, using a similar method to the one described in Example 1.13, step E, the title compound was obtained as an yellow solid. $^1$H NMR (400 MHz, CDCl$_3$) δ ppm 1.43-1.48 (m, 2H), 1.48 (s, 9H), 1.49-1.53 (m, 2H), 1.56-1.65 (m, 4H), 1.84-1.92 (m, 1H), 2.29-2.35 (m, 1H), 2.38 (s, 3H), 3.45 (d, J=6.82 Hz, 2H), 3.95 (s, 2H), 4.22 (d, J=7.58 Hz, 2H), 7.12-7.17 (m, 4H), 7.19 (t, J=7.83 Hz, 1H), 7.23-7.28 (m, 1H), 7.37-7.43 (m, 1H), 7.61 (t, J=1.77 Hz, 1H).

Step B: Preparation of 2-(((1s,4s)-4-((5-(3-Chlorophenyl)-3-oxo-6-p-tolyl-1,2,4-triazin-2(3H)-yl)methyl)cyclohexyl)methoxy)acetic Acid (Compound 85)

From tert-butyl 2-(((1s,4s)-4-((5-(3-chlorophenyl)-3-oxo-6-p-tolyl-1,2,4-triazin-2(3H)-yl)methyl)cyclohexyl)methoxy)acetate, using a similar method to the one described in Example 1.13, step F, the title compound was obtained as a yellow solid. LCMS m/z=482.2 [M+H]+; $^1$H NMR (400 MHz, DMSO-d$_6$) δ ppm 1.36-1.54 (m, 6H), 1.68-1.80 (m, 2H), 2.12-2.21 (m, 1H), 2.30 (s, 3H), 3.22-3.27 (m, 1H), 3.39 (d, J=7.07 Hz, 2H), 3.98 (s, 2H), 4.10 (d, J=7.58 Hz, 2H), 7.13-7.19 (m, 4H), 7.24-7.30 (m, 1H), 7.36 (t, J=7.96 Hz, 1H), 7.47 (t, J=1.77 Hz, 1H), 7.51-7.54 (m, 1H), 12.49 (s, 1H).

Example 1.88

Preparation of Sodium 2-(2-(((1s,4s)-4-((3-Oxo-5-phenyl-6-p-tolyl-1,2,4-triazin-2(3H)-yl)methyl)cyclohexyl)methoxy)acetamido)acetate (Compound 86 Sodium Salt)

Step A: Preparation of 2-(2-(((1s,4s)-4-((3-oxo-5-phenyl-6-p-tolyl-1,2,4-triazin-2(3H)-yl)methyl)cyclohexyl)methoxy)acetamido)acetic acid A mixture of 2-(((1s,4s)-4-((3-oxo-5-phenyl-6-p-tolyl-1,2,4-triazin-2(3H)-yl)methyl)cyclohexyl)methoxy)acetic acid (0.2 g, 0.447 mmol), tert-butyl 2-aminoacetate (0.059 g, 0.447 mmol), HATU (0.170 g, 0.447 mmol) and Et$_3$N (0.187 mL, 1.341 mmol) in DMF (2 ml) was stirred at room temperature overnight. The mixture was purified by preparative HPLC. To the above product was added HCl (2 mL, 8.00 mmol) in 1,4-dioxane. The mixture was stirred at room temperature for 4 h. Then the solvent was removed under reduced pressure to give the title compound. LCMS m/z=505.3 [M+H]+.

Step B: Preparation of sodium 2-(2-(((1s,4s)-4-((3-oxo-5-phenyl-6-p-tolyl-1,2,4-triazin-2(3H)-yl)methyl)cyclohexyl)methoxy)acetamido)acetate To a mixture of 2-(2-(((1s,4s)-4-((3-oxo-5-phenyl-6-p-tolyl-1,2,4-triazin-2(3H)-yl)methyl)cyclohexyl)methoxy)acetamido)acetic acid (0.1 g, 0.198 mmol) in DCM (5 ml) was added 0.5 M NaOH solution (0.396 ml, 0.198 mmol) at room temperature. The mixture was stirred at 25° C. for 2 h. The solvent was removed under reduced pressure to give the title compound as a yellow solid. $^1$H NMR (400 MHz, CDCl3) δ ppm 7.49 (d, J=7.6 Hz, 2H), 7.32 (d, J=7.2 Hz, 2H), 7.15 (m, 5H), 4.25 (d, J=7.7 Hz, 2H), 4.14 (d, J=5.4 Hz, 2H), 4.03 (s, 2H), 3.49 (d, J=6.4 Hz, 2H), 2.37 (s, 3H), 1.84 (m, 1H), 1.61-1.49 (m, 9H).

Example 1.89

Preparation of 2-(2-(((1s,4s)-4-((3-Oxo-5-phenyl-6-p-tolyl-1,2,4-triazin-2(3H)-yl)methyl)cyclohexyl)methoxy)acetamido)ethanesulfonic Acid (Compound 87)

In a 50 mL flask, 2-(((1s,4s)-4-((3-oxo-5-phenyl-6-p-tolyl-1,2,4-triazin-2(3H)-yl)methyl)cyclohexyl)methoxy)acetic acid (1.0 g, 2.235 mmol) was dissolved in thionyl chloride (7.6 g, 63.8 mmol) and heated at 80° C. for 6 hours. The mixture was cooled and solvent was removed. The residue was dissolved in 1,4-dioxane (5 mL) and cooled to 10° C. Taurine (0.839 g, 6.70 mmol) dissolved in aqueous sodium hydroxide solution (0.259 g in 5 mL $H_2O$) was added. The mixture was stirred at room temperature. The solvents were removed, and the residue was dissolved in a mixture of ethyl acetate and 1 N HCl (10 mL each). The aqueous layer was concentrated and the yellow solid residue was suspended in ethanol and filtered. The filtrate was concentrated and isopropanol was added. The brown solid was filtered and dried to give the title compound (100 mg). LCMS m/z=555.8 $[M+H]^+$; NMR (400 MHz, DMSO-$d_6$) δ ppm 1.34-1.59 (m, 6H), 1.77 (s, 1H), 2.30 (s, 3H), 2.55 (t, J=6.44 Hz, 1H), 2.71 (s, 1H), 3.05 (s, 3H), 3.16-3.46 (m, 4H), 3.73-3.87 (m, 2H), 4.11 (d, 1H), 7.15 (s, 3H), 7.27-7.50 (m, 4H), 7.65 (s, 3H), 7.95 (t, J=5.18 Hz, 1H), 9.61 (s, 1H).

Example 2

Homogeneous Time-Resolved Fluorescence (HTRF®) Assay for Direct cAMP Measurement Compounds were screened for agonists of the human prostacyclin (PGI2) receptor using the HTRF® assay for direct cAMP measurement (Gabriel et al., ASSAY and Drug Development Technologies, 1:291-303, 2003) and recombinant CHO-K1 cells stably transfected with human prostacyclin receptor. CHO-K1 cells were obtained from ATCC® (Manassas, Va.; Catalog #CCL-61). An agonist of the prostacyclin receptor was detected in HTRF® assay for direct cAMP measurement as a compound which increased cAMP concentration. HTRF® assay also was used to determine $EC_{50}$ values for prostacyclin receptor agonists.

Principle of the Assay:

The HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

Standard Curve:

The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

Setup of the Assay:

The HTRF® assay was carried out using a two-step protocol essentially according to the kit manufacturer's instructions, in 20 µL total volume per well in 384-well plate format (ProxiPlates; PerkinElmer, Fremont, Calif.; catalog #6008280). To each of the experimental wells was transferred 3000 recombinant CHO-K1 cells in 5 µL assay buffer (phosphate buffered saline containing calcium chloride and magnesium chloride (Invitrogen, Carlsbad, Calif.; catalog #14040) supplemented with IBMX (100 µM) and rolipram (10 µM) (phosphodiesterase inhibitors; Sigma-Aldrich, St. Louis, Mo.; catalog #15879 and catalog #R6520, respectively) and 0.1% bovine serum albumin (BSA) fraction V (Sigma-Aldrich; catalog # A3059)), followed by test compound in 5 µL assay buffer or 5 µL assay buffer. The plate was then incubated at room temperature for 1 h. To each well was then added 5 µL cAMP-$d_2$ conjugate in lysis buffer and 5 µL Cryptate conjugate in lysis buffer according to the kit manufacturer's instructions. The plate was then further incubated at room temperature for 1 h, after which the assay plate was read.

Assay Readout:

The HTRF® readout was accomplished using a PHERAstar (BMG LABTECH Inc., Durham, N.C.) or EnVision™ (PerkinElmer, Fremont Calif.) microplate reader.

Certain compounds of the present invention and their corresponding activity values are shown in TABLE B.

TABLE B

| Compound No. | human PGI2 receptor $EC_{50}$ (nM) (HTRF ®) |
|---|---|
| 69 | 8 nM |
| 31 | 31 nM |
| 43 | 36 nM |
| 67 | 73 nM |

Certain other compounds of the invention had activity values ranging from about 2.1 nM to about 4 µM in this assay.

Example 3

Human Platelet Aggregation Inhibition Test

Blood collected from healthy human volunteers in aqueous trisodium citrate solution was centrifuged at 150 g for 15 min and the upper layer was recovered to obtain platelet-rich plasma (PRP). The residual blood was centrifuged at 3000 g for 10 min and the supernatant was collected as platelet-poor plasma (PPP). Platelet concentration in the PRP was determined using the Z series Beckman Coulter particle counter (Beckman, Fullerton, Calif.) and adjusted to 250,000 platelets/µL using PPP. 480 µL of PRP was pre-incubated at 37° C. and stirred at 1200 rpm with 10 µL aqueous test compound solution for 1 min prior to induction of aggregation by the addition of 10 µL of aqueous adenosine diphosphate (ADP) solution to adjust the final ADP concentration in the PRP to $1 \times 10^{-5}$ M. The maximal amplitude of aggregation response within 3 min was determined and measured in triplicate using the Chronolog model 490 aggregometer (Chrono-log Corp., Havertown, Pa.). Percent inhibition of aggregation was calculated from the maximum decrease in optical density of the control (addition of water in place of the test compound solution) sample and of the samples containing test compound. The test compound was added to adjust the final concentration to the range $10^{-9}$ to $10^{-4}$ M, and $IC_{50}$ values were determined by inhibition percentage of aggregation at each concentration. The results are shown in Table C.

TABLE C

| Compound No. | human PRP IC$_{50}$ (nM) |
| --- | --- |
| 69 | 22 nM |
| 31 | 21 nM |
| 43 | 130 nM |
| 8 | 67 nM |

Certain other compounds of the invention had activity values ranging from about 12 nM to about 160 nM in this assay.

It is apparent that the compounds of the present invention markedly inhibit platelet aggregation in human PRP.

Example 4

Rat Model of Pulmonary Arterial Hypertension

Animals:

Male Wistar rats (100-150 g at start of study) (Charles River Laboratories, Wilmington, Mass.) were housed two per cage and maintained in a humidity-(40-60%) and temperature-(68-72° F.) controlled facility on a 12 hr:12 hr light/dark cycle (lights on at 6:30 am) with free access to food (Harlan Teklad, Orange Calif., Rodent Diet 8604) and water. Rats were allowed one week of habituation to the animal facility before testing.

Rat Monocrotaline Model:

The rat monocrotaline (MCT) model is a standard and well-accepted model of pulmonary arterial hypertension. MCT induces acute pulmonary endothelial damage associated with pulmonary vascular inflammation. Subsequently, pulmonary artery smooth muscle cells proliferate, occluding small pulmonary vessels and leading to severe pulmonary arterial hypertension including right ventricular hypertrophy. (See, e.g., Schermuly et al., Circ. Res., 2004, 94:1101-1108.)

Rats were randomly given a single subcutaneous injection of either 60 mg/kg MCT (Sigma, St. Louis, Mo.) or 0.9% saline (sham) and assigned to receive oral administration of 20% hydroxypropyl beta-cyclodextrin (vehicle) or test compound (30 mg/kg; FIG. 1). 10-11 rats were used per treatment group. 24 h following MCT administration, test compound or vehicle was administered by oral gavage twice a day for 21 consecutive days. Heart chamber weights were measured on Day 22. Rats were anesthetized with intraperitoneal pentobarbital (50 mg/kg), the chest cavity was opened and the heart was excised. The right ventricle was dissected free from the septum and left ventricle and both parts were weighed. The ratio of right ventricular (RV) weight to left ventricle plus septum (LV+S) weight (this ratio is indicated as "RV/(LV+S)" in FIG. 1) was calculated as an index of the hypertrophic response to the induced pulmonary arterial hypertension and, as such, as an index of a test compound's therapeutic efficacy for pulmonary arterial hypertension.

It is apparent from inspection of FIG. 1 that oral administration of Compound 68 inhibited the hypertrophic response to the induced pulmonary arterial hypertension and, as such, evidenced therapeutic efficacy for pulmonary arterial hypertension.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

What is claimed is:

1. A compound of Formula Ia or a pharmaceutically acceptable salt, solvate or hydrate thereof:

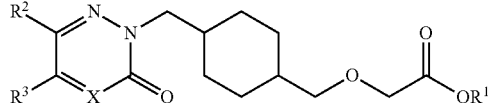

Ia wherein:

$R^1$ is selected from: H and $C_1$-$C_8$ alkyl;

$R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen; and X is N.

2. The compound according to claim 1, or a pharmaceutically acceptable salt, solvate or hydrate thereof, wherein $R^1$ is H.

3. The compound according to claim 1, or a pharmaceutically acceptable salt, solvate or hydrate thereof, wherein $R^1$ is $C_1$-$C_6$ alkyl.

4. The compound according to claim 1, or a pharmaceutically acceptable salt, solvate or hydrate thereof, wherein $R^2$ and $R^3$ are each independently selected from: H, $C_1$-$C_8$ alkyl, aryl and heteroaryl; wherein said $C_1$-$C_8$ alkyl, aryl and heteroaryl are each optionally substituted with one or more substituents each independently selected from: chloro, ethyl, fluoro, isopropyl, methoxy, methyl, methylthio, phenyl and trifluoromethyl.

5. The compound according to claim 1, or a pharmaceutically acceptable salt, solvate or hydrate thereof, wherein $R^2$ and $R^3$ are each independently selected from: H, 1H-pyrazol-4-yl, methyl, phenyl, pyridinyl, thiophen-2-yl and thiophen-3-yl; wherein said methyl, phenyl, pyridinyl, thiophen-2-yl and thiophen-3-yl are each optionally substituted with one or more substituents each independently selected from: chloro, ethyl, fluoro, isopropyl, methoxy, methyl, methylthio, phenyl and trifluoromethyl.

6. The compound according to claim 1, or a pharmaceutically acceptable salt, solvate or hydrate thereof, wherein $R^2$ and $R^3$ are each independently selected from: H, 1H-pyrazol-4-yl, 2,3-difluorophenyl, 2-chlorophenyl, 2-chloropyridin-4-yl, 2-fluoro-3-methoxyphenyl, 2-fluoro-4-methylphenyl, 2-fluorophenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-chloropyridin-3-yl, 6-fluoropyridin-3-yl, 6-methylpyridin-3-yl, benzhydryl, m-tolyl, phenyl, p-tolyl, pyridin-3-yl, pyridin-4-yl, thiophen-2-yl and thiophen-3-yl.

7. The compound according to claim 1, or a pharmaceutically acceptable salt, solvate or hydrate thereof, wherein $R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen.

8. The compound according to claim 1, or a pharmaceutically acceptable salt, solvate or hydrate thereof, wherein $R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: chloro, ethyl, fluoro, isopropyl, methoxy, methyl, methylthio, phenyl and trifluoromethyl.

9. The compound according to claim 1, or a pharmaceutically acceptable salt, solvate or hydrate thereof, wherein $R^2$ is selected from: methyl, phenyl, pyridinyl, thiophen-2-yl and thiophen-3-yl; wherein said methyl, phenyl, pyridinyl, thiophen-2-yl and thiophen-3-yl are each optionally substituted with one or more substituents each independently selected from: chloro, ethyl, fluoro, isopropyl, methoxy, methyl, methylthio, phenyl and trifluoromethyl.

10. The compound according to claim 1, or a pharmaceutically acceptable salt, solvate or hydrate thereof, wherein $R^2$ is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl.

11. The compound according to claim 1, or a pharmaceutically acceptable salt, solvate or hydrate thereof, wherein $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy and halogen.

12. The compound according to claim 1, or a pharmaceutically acceptable salt, solvate or hydrate thereof, wherein $R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: chloro, fluoro, methoxy and methyl.

13. The compound according to claim 1, or a pharmaceutically acceptable salt, solvate or hydrate thereof, wherein $R^3$ is selected from: H, 1H-pyrazol-4-yl, phenyl, pyridinyl and thiophen-2-yl; wherein said phenyl, pyridinyl and thiophen-2-yl are each optionally substituted with one or more substituents each independently selected from: chloro, fluoro, methoxy and methyl.

14. The compound according to claim 1, or a pharmaceutically acceptable salt, solvate or hydrate thereof, wherein $R^3$ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

15. The compound according to claim 1, of Formula Ic or a pharmaceutically acceptable salt, solvate or hydrate thereof:

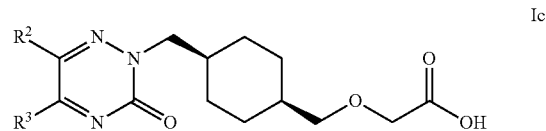

Ic wherein:
$R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen; and
$R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy and halogen.

16. The compound according to claim 1, of Formula Ic or a pharmaceutically acceptable salt, solvate or hydrate thereof:

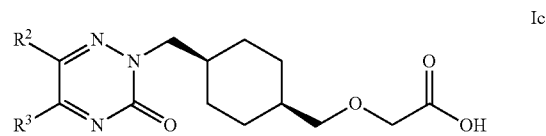

Ic wherein:
$R^2$ is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl; and
$R^3$ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

17. The compound according to claim 1, of Formula Ie or a pharmaceutically acceptable salt, solvate or hydrate thereof:

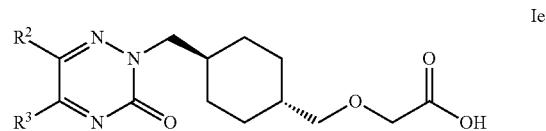

Ie wherein:
R² is selected from: C₁-C₈ alkyl, aryl and heteroaryl; wherein said C₁-C₈ alkyl, aryl and heteroaryl are each optionally substituted with one or more substituents each independently selected from: C₁-C₈ alkyl, C₁-C₈ alkoxy, C₁-C₈ alkylthio, aryl, C₁-C₈ haloalkyl and halogen; and
R³ is selected from: H, C₁-C₈ alkyl, aryl and heteroaryl; wherein said C₁-C₈ alkyl, aryl and heteroaryl are each optionally substituted with one or more substituents each independently selected from: C₁-C₈ alkyl, C₁-C₈ alkoxy and halogen.

18. The compound according to claim 1, of Formula Ie or a pharmaceutically acceptable salt, solvate or hydrate thereof:

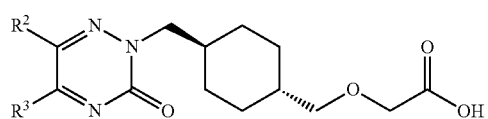

Ie wherein:
R² is selected from: 2,3-difluorophenyl, 2-chlorophenyl, 2-fluoro-4-methylphenyl, 2-fluorophenyl, 2-methoxyphenyl, 3-chlorophenyl, 3-fluoro-4-methylphenyl, 3-fluoro-5-methoxyphenyl, 3-fluorophenyl, 3-methoxyphenyl, 4-(methylthio)phenyl, 4-(trifluoromethyl)phenyl, 4-chloro-2-fluorophenyl, 4-chloro-3-fluorophenyl, 4-chlorophenyl, 4-ethylphenyl, 4-fluorophenyl, 4-isopropylphenyl, 4-methoxyphenyl, 5-methylpyridin-3-yl, 6-chloropyridin-3-yl, 6-methylpyridin-3-yl, benzhydryl, phenyl, p-tolyl, pyridin-3-yl, pyridin-4-yl, thiophen-2-yl and thiophen-3-yl; and
R³ is selected from: H, 1H-pyrazol-4-yl, 2,3-difluorophenyl, 2-chlorophenyl, 2-chloropyridin-4-yl, 2-fluoro-3-methoxyphenyl, 2-fluoropyridin-3-yl, 2-fluoropyridin-4-yl, 2-methoxyphenyl, 2-methylpyridin-4-yl, 3,4-dichlorophenyl, 3,5-dichlorophenyl, 3-chloro-2-fluorophenyl, 3-chloro-4-fluorophenyl, 3-chlorophenyl, 3-fluoro-5-methoxyphenyl, 3-fluorophenyl, 3-methoxyphenyl, 4-chlorophenyl, 4-fluorophenyl, 4-methoxyphenyl, 4-methylthiophen-2-yl, 5-chloro-2-fluorophenyl, 5-chloro-pyridin-3-yl, 5-methylpyridin-3-yl, 5-methylthiophen-2-yl, 6-fluoropyridin-3-yl, m-tolyl, phenyl, p-tolyl, pyridin-3-yl, pyridin-4-yl and thiophen-2-yl.

19. A compound according to claim 1 selected from
2-(((1s,4s)-4-((3-oxo-5,6-di-p-tolyl-1,2,4-triazin-2(3H)-ylmethyl)cyclohexyl)methoxy)acetic acid;
2-(((1s,4s)-4-((3-oxo-5,6-diphenyl-1,2,4-triazin-2(3H)-ylmethyl)cyclohexyl)methoxy)acetic acid;
2-(((1s,4s)-4-((5,6-bis(4-fluorophenyl)-3-oxo-1,2,4-triazin-2(3H)-yl)methyl)cyclohexyl)methoxy)acetic acid;
2-(((1s,4s)-4-((6-(4-fluorophenyl)-3-oxo-5-phenyl-1,2,4-triazin-2(3H)-yl)methyl)cyclohexyl)methoxy)acetic acid;
2-(((1s,4s)-4-((5-(3-chlorophenyl)-3-oxo-6-phenyl-1,2,4-triazin-2(3H)-yl)methyl)cyclohexyl)methoxy)acetic acid;
2-(((1s,4s)-4-((3-oxo-5-phenyl-6-p-tolyl-1,2,4-triazin-2(3H)-yl)methyl)cyclohexyl)methoxy)acetic acid;
2-(((1s,4s)-4-((6-(4-methoxyphenyl)-3-oxo-5-phenyl-1,2,4-triazin-2(3H)-yl)methyl)cyclohexyl)methoxy)acetic acid;
2-(((1s,4s)-4-((5-(3-methoxyphenyl)-3-oxo-6-phenyl-1,2,4-triazin-2(3H)-yl)methyl)cyclohexyl)methoxy)acetic acid;
2-(((1s,4s)-4-((6-(2-fluoro-4-methylphenyl)-3-oxo-5-phenyl-1,2,4-triazin-2(3H)-yl)methyl)cyclohexyl)methoxy)acetic acid;
2-(((1s,4s)-4-((6-(4-chlorophenyl)-3-oxo-5-phenyl-1,2,4-triazin-2(3H)-yl)methyl)cyclohexyl)methoxy)acetic acid;
2-(((1s,4s)-4-((3-oxo-6-phenyl-5-m-tolyl-1,2,4-triazin-2(3H)-yl)methyl)cyclohexyl)methoxy)acetic acid;
2-(((1s,4s)-4-((5-(3-fluorophenyl)-3-oxo-6-phenyl-1,2,4-triazin-2(3H)-yl)methyl)cyclohexyl)methoxy)acetic acid;
2-(((1r,4r)-4-((6-(2-fluoro-4-methylphenyl)-3-oxo-5-phenyl-1,2,4-triazin-2(3H)-yl)methyl)cyclohexyl)methoxy)acetic acid;
2-(((1r,4r)-4-((3-oxo-5-phenyl-6-p-tolyl-1,2,4-triazin-2(3H)-yl)methyl)cyclohexyl)methoxy)acetic acid;
2-(((1s,4s)-4-((3-oxo-6-phenyl-5-(pyridin-3-yl)-1,2,4-triazin-2(3H)-yl)methyl)cyclohexyl)methoxy)acetic acid;
2-(((1s,4s)-4-((3-oxo-6-(pyridin-3-yl)-5-p-tolyl-1,2,4-triazin-2(3H)-yl)methyl)cyclohexyl)methoxy)acetic acid;
2-(((1s,4s)-4-((3-oxo-5-(pyridin-4-yl)-6-p-tolyl-1,2,4-triazin-2(3H)-yl)methyl)cyclohexyl)methoxy)acetic acid;
2-(((1s,4s)-4-((3-oxo-5-m-tolyl-6-p-tolyl-1,2,4-triazin-2(3H)-yl)methyl)cyclohexyl)methoxy)acetic acid;
2-(((1r,4r)-4-((3-oxo-6-phenyl-5-m-tolyl-1,2,4-triazin-2(3H)-yl)methyl)cyclohexyl)methoxy)acetic acid;
2-(((1r,4r)-4-((5-(3-fluorophenyl)-3-oxo-6-phenyl-1,2,4-triazin-2(3H)-yl)methyl)cyclohexyl)methoxy)acetic acid;
2-(((1r,4r)-4-((3-oxo-5-m-tolyl-6-p-tolyl-1,2,4-triazin-2(3H)-yl)methyl)cyclohexyl)methoxy)acetic acid; and
2-(((1s,4s)-4-((3-oxo-6-phenyl-5-(thiophen-2-yl)-1,2,4-triazin-2(3H)-yl)methyl)cyclohexyl)methoxy)acetic acid;

or a pharmaceutically acceptable salt, solvate or hydrate thereof.

20. A compound of Formula IIa or a pharmaceutically acceptable salt, solvate or hydrate thereof:

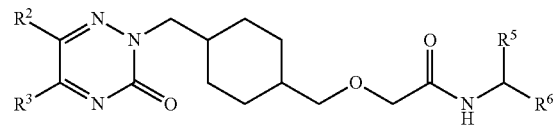

IIa wherein:
R² and R³ are each independently selected from: H, C₁-C₈ alkyl, aryl and heteroaryl; wherein said C₁-C₈ alkyl, aryl and heteroaryl are each optionally substituted with one or more substituents each independently selected from: C₁-C₈ alkyl, C₁-C₈ alkoxy, C₁-C₈ alkylthio, aryl, C₁-C₈ haloalkyl and halogen;
R⁵ is selected from: H and carboxyl; and
R⁶ is selected from: H and C₁-C₆ alkyl; wherein C₁-C₆ alkyl is optionally substituted with 4-hydroxyphenyl, amino, carboxamide, carboxyl, guanidino, hydroxyl, imidazolyl, indolyl, methylthio, phenyl, pyrrolidinyl, sulfo and thiol.

21. A compound according to claim 20 of Formula IIa or a pharmaceutically acceptable salt, solvate or hydrate thereof:

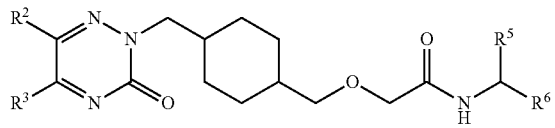

IIa wherein:
$R^2$ is selected from: $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy, $C_1$-$C_8$ alkylthio, aryl, $C_1$-$C_8$ haloalkyl and halogen;
$R^3$ is selected from: H, $C_1$-$C_8$ alkyl, aryl and heteroaryl; wherein said $C_1$-$C_8$ alkyl, aryl and heteroaryl are each optionally substituted with one or more substituents each independently selected from: $C_1$-$C_8$ alkyl, $C_1$-$C_8$ alkoxy and halogen;
$R^5$ is H or carboxyl; and
$R^6$ is H or —$CH_2SO_3H$.

22. A compound according to claim 20, which is 2-(2-(((1s,4s)-4-((3-oxo-5-phenyl-6-p-tolyl-1,2,4-triazin-2(3H)-yl)methyl)cyclohexyl)methoxy)acetamido)acetic acid, or a pharmaceutically acceptable salt, solvate or hydrate thereof.

23. A compound according to claim 20, which is 2-(2-(((1s,4s)-4-((3-oxo-5-phenyl-6-p-tolyl-1,2,4-triazin-2(3H)-yl)methyl)cyclohexyl)methoxy)acetamido)ethanesulfonic acid, or a pharmaceutically acceptable salt, solvate or hydrate thereof.

24. A pharmaceutical composition comprising a compound according to claim 1, or a pharmaceutically acceptable salt, solvate or hydrate thereof, and a pharmaceutically acceptable carrier.

25. A method for the treatment of PAH in an individual, comprising administering to said individual in need thereof, a therapeutically effective amount of a compound according to claim 1, or a pharmaceutically acceptable salt, solvate or hydrate thereof.

26. The method according to claim 25, wherein said PAH is selected from:
idiopathic PAH;
familial PAH;
PAH associated with a collagen vascular disease selected from: scleroderma, CREST syndrome, systemic lupus erythematosus (SLE), rheumatoid arthritis, Takayasu's arteritis, polymyositis, and dermatomyositis;
PAH associated with a congenital heart disease selected from: atrial septic defect (ASD), ventricular septic defect (VSD) and patent ductus arteriosus in an individual;
PAH associated with portal hypertension;
PAH associated with HIV infection;
PAH associated with ingestion of a drug or toxin;
PAH associated with hereditary hemorrhagic telangiectasia;
PAH associated with splenectomy;
PAH associated with significant venous or capillary involvement;
PAH associated with pulmonary veno-occlusive disease (PVOD); and
PAH associated with pulmonary capillary hemangiomatosis (PCH) in an individual.

27. A process for preparing a composition comprising admixing a compound according to claim 1, or a pharmaceutically acceptable salt, solvate or hydrate thereof, and a pharmaceutically acceptable carrier.

28. A compound according claim 1, which is 2-(((1s,4s)-4-((3-oxo-5-phenyl-6-p-tolyl-1,2,4-triazin-2(3H)-yl)methyl)cyclohexyl)methoxy)acetic acid, or a pharmaceutically acceptable salt, solvate or hydrate thereof.

29. A pharmaceutical composition comprising a compound according to claim 28, or a pharmaceutically acceptable salt, solvate or hydrate thereof, and a pharmaceutically acceptable carrier.

30. A method for the treatment of PAH in an individual, comprising administering to said individual in need thereof, a therapeutically effective amount of a compound according to claim 28, or a pharmaceutically acceptable salt, solvate or hydrate thereof.

31. The method according to claim 30, wherein said PAH is selected from:
idiopathic PAH;
familial PAH;
PAH associated with a collagen vascular disease selected from: scleroderma, CREST syndrome, systemic lupus erythematosus (SLE), rheumatoid arthritis, Takayasu's arteritis, polymyositis, and dermatomyositis;
PAH associated with a congenital heart disease selected from: atrial septic defect (ASD), ventricular septic defect (VSD) and patent ductus arteriosus in an individual;
PAH associated with portal hypertension;
PAH associated with HIV infection;
PAH associated with ingestion of a drug or toxin;
PAH associated with hereditary hemorrhagic telangiectasia;
PAH associated with splenectomy;
PAH associated with significant venous or capillary involvement;
PAH associated with pulmonary veno-occlusive disease (PVOD); and
PAH associated with pulmonary capillary hemangiomatosis (PCH) in an individual.

32. A process for preparing a composition comprising admixing a compound according to claim 28, or a pharmaceutically acceptable salt, solvate or hydrate thereof, and a pharmaceutically acceptable carrier.

33. A pharmaceutical composition comprising a compound according to claim 20, or a pharmaceutically acceptable salt, solvate or hydrate thereof, and a pharmaceutically acceptable carrier.

34. A method for the treatment of PAH in an individual, comprising administering to said individual in need thereof, a therapeutically effective amount of a compound according to claim 20, or a pharmaceutically acceptable salt, solvate or hydrate thereof.

35. The method according to claim 34, wherein said PAH is selected from:
idiopathic PAH;
familial PAH;
PAH associated with a collagen vascular disease selected from: scleroderma, CREST syndrome, systemic lupus erythematosus (SLE), rheumatoid arthritis, Takayasu's arteritis, polymyositis, and dermatomyositis;

PAH associated with a congenital heart disease selected from: atrial septic defect (ASD), ventricular septic defect (VSD) and patent ductus arteriosus in an individual;

PAH associated with portal hypertension;

PAH associated with HIV infection;

PAH associated with ingestion of a drug or toxin;

PAH associated with hereditary hemorrhagic telangiectasia;

PAH associated with splenectomy;

PAH associated with significant venous or capillary involvement;

PAH associated with pulmonary veno-occlusive disease (PVOD); and

PAH associated with pulmonary capillary hemangiomatosis (PCH) in an individual.

36. A process for preparing a composition comprising admixing a compound according to claim 20, or a pharmaceutically acceptable salt, solvate or hydrate thereof, and a pharmaceutically acceptable carrier.

37. A pharmaceutical composition comprising a compound according to claim 22, or a pharmaceutically acceptable salt, solvate or hydrate thereof, and a pharmaceutically acceptable carrier.

38. A method for the treatment of PAH in an individual, comprising administering to said individual in need thereof, a therapeutically effective amount of a compound according to claim 22, or a pharmaceutically acceptable salt, solvate or hydrate thereof.

39. The method according to claim 38, wherein said PAH is selected from:

idiopathic PAH;

familial PAH;

PAH associated with a collagen vascular disease selected from: scleroderma, CREST syndrome, systemic lupus erythematosus (SLE), rheumatoid arthritis, Takayasu's arteritis, polymyositis, and dermatomyositis;

PAH associated with a congenital heart disease selected from: atrial septic defect (ASD), ventricular septic defect (VSD) and patent ductus arteriosus in an individual;

PAH associated with portal hypertension;

PAH associated with HIV infection;

PAH associated with ingestion of a drug or toxin;

PAH associated with hereditary hemorrhagic telangiectasia;

PAH associated with splenectomy;

PAH associated with significant venous or capillary involvement;

PAH associated with pulmonary veno-occlusive disease (PVOD); and

PAH associated with pulmonary capillary hemangiomatosis (PCH) in an individual.

40. A process for preparing a composition comprising admixing a compound according to claim 22, or a pharmaceutically acceptable salt, solvate or hydrate thereof, and a pharmaceutically acceptable carrier.

41. A pharmaceutical composition comprising a compound according to claim 23, or a pharmaceutically acceptable salt, solvate or hydrate thereof, and a pharmaceutically acceptable carrier.

42. A method for the treatment of PAH in an individual, comprising administering to said individual in need thereof, a therapeutically effective amount of a compound according to claim 23, or a pharmaceutically acceptable salt, solvate or hydrate thereof.

43. The method according to claim 42, wherein said PAH is selected from:

idiopathic PAH;

familial PAH;

PAH associated with a collagen vascular disease selected from: scleroderma, CREST syndrome, systemic lupus erythematosus (SLE), rheumatoid arthritis, Takayasu's arteritis, polymyositis, and dermatomyositis;

PAH associated with a congenital heart disease selected from: atrial septic defect (ASD), ventricular septic defect (VSD) and patent ductus arteriosus in an individual;

PAH associated with portal hypertension;

PAH associated with HIV infection;

PAH associated with ingestion of a drug or toxin;

PAH associated with hereditary hemorrhagic telangiectasia;

PAH associated with splenectomy;

PAH associated with significant venous or capillary involvement;

PAH associated with pulmonary veno-occlusive disease (PVOD); and

PAH associated with pulmonary capillary hemangiomatosis (PCH) in an individual.

44. A process for preparing a composition comprising admixing a compound according to claim 23, or a pharmaceutically acceptable salt, solvate or hydrate thereof, and a pharmaceutically acceptable carrier.

* * * * *